(12) United States Patent
Cocks et al.

(10) Patent No.: US 6,607,879 B1
(45) Date of Patent: Aug. 19, 2003

(54) COMPOSITIONS FOR THE DETECTION OF BLOOD CELL AND IMMUNOLOGICAL RESPONSE GENE EXPRESSION

(75) Inventors: Benjamin G. Cocks, Sunnyvale, CA (US); Susan G. Stuart, Montara, CA (US); Jeffrey J. Seilhamer, Los Altos Hills, CA (US)

(73) Assignee: Incyte Corporation, Palo Alto, CA (US)

( * ) Notice: Subject to any disclaimer, the term of this patent is extended or adjusted under 35 U.S.C. 154(b) by 0 days.

(21) Appl. No.: 09/023,655

(22) Filed: Feb. 9, 1998

(51) Int. Cl.[7] .......................... C12Q 1/68; C07H 21/00
(52) U.S. Cl. .................. 435/6; 435/69.1; 536/23.1; 536/24.1; 536/24.3; 536/24.31; 536/24.32; 536/24.33
(58) Field of Search .................. 435/6, 69.1; 536/22.1, 536/23.1, 24.1, 24.3–24.33

(56) References Cited

PUBLICATIONS

Attwood, Science, vol. 290, No. 5491, pp. 471–473, 2000.*
Wells et al., Journal of Leukocyte Biology, vol. 61, No. 5, pp. 545–550, 1997.*
Russell et al., Journal of Molecular Biology, vol. 244, pp. 332–350, 1994.*
Gerhold et al., Bio–Essays, vol. 18., No. 12, pp. 973–981, 1996.*
Lashkari, D.A. et al., "Yeast microarrays for genome wide parallel genetic and gene expression analysis", *Proc. Natl. Acad. Sci. USA*, 94: 13057–13062 (1997).
Schena, M. et al., "Parallel human genome analysis: Microarray–based expression monitoring of 1000 genes", *Proc. Natl. Acad. Sci. USA*, 93: 10614–10619 (1996).
Heller, R.A. et al., "Discovery and analysis of inflammatory disease–related genes using cDNA microarrays", *Proc. Natl. Acad. Sci. USA*, 94: 2150–2155 (1997).
Schena, M. et al., "Quantitative Monitorin of Gene Expression Patterns with a Complementary DNA Microarray", *Science*, 270: 467–470 (1995).
Okubo, K. et al., "Large scale cDNA sequencing for analysis of quantitative and qualitative aspects of gene expression", *Nature Genetics*, 2: 173–179 (1992).
CLONTECH Catalog: Atlas Human cDNA Expression Array I, (obtained from CLONTECH Internet site), 36 pages (1998).
Lockhart, D.J. et al., "Expression monitoring by hybridization to high–density oligonucleotide arrays", *Nature Biotechnology*, 14: 1675–1680 (1996).

* cited by examiner

Primary Examiner—Ardin H. Marschel
(74) Attorney, Agent, or Firm—Incyte Corporation

(57) ABSTRACT

The present invention relates to a composition comprising a plurality of polynucleotide probes. The composition can be used as hybridizable array elements in a microarray. The present invention also relates to a method for selecting polynucleotide probes for the composition.

7 Claims, 2 Drawing Sheets

COMPOSITIONS FOR THE DETECTION OF BLOOD CELL AND IMMUNOLOGICAL RESPONSE GENE EXPRESSION

FIELD OF THE INVENTION

The present invention relates to a composition comprising a plurality of polynucleotide probes for use in research and diagnostic applications.

BACKGROUND OF THE INVENTION

DNA-based arrays can provide a simple way to explore the expression of a single polymorphic gene or a large number of genes. When the expression of a single gene is explored, DNA-based arrays are employed to detect the expression of specific gene variants. For example, a p53 tumor suppressor gene array is used to determine whether individuals are carrying mutations that predispose them to cancer. The array has over 50,000 DNA probes to analyze more than 400 distinct mutations of p53. A cytochrome p450 gene array is useful to determine whether individuals have one of a number of specific mutations that could result in increased drug metabolism, drug resistance or drug toxicity.

DNA-based array technology is especially relevant for the rapid screening of expression of a large number of genes. There is a growing awareness that gene expression is affected in a global fashion. A genetic predisposition, disease or therapeutic treatment may affect, directly or indirectly, the expression of a large number of genes. In some cases the interactions may be expected, such as where the genes are part of the same signaling pathway. In other cases, such as when the genes participate in separate signaling pathways, the interactions may be totally unexpected. Therefore, DNA-based arrays can be used to investigate how genetic predisposition, disease, or therapeutic treatment affects the expression of a large number of genes.

cDNA-based arrays have been used in discovery and analysis of inflammatory disease related genes (Heller et al. (1997) Proc. Natl. Acad. Sci USA 94: 2150–2155). A first type of array was employed to characterize the expression patterns of a class of 96 genes coding for polypeptides known to be involved in rheumatoid arthritis. This array contained preselected probes for the 96 genes. A second type of array was used to investigate gene expression patterns characteristic of blood cells. This array contained probes for 1,000 human genes randomly selected from a human blood cell cDNA library.

Current cDNA-based arrays suffer from a variety of limitations. One is the first type of array can only detect the expression patterns of a limited number of genes already associated with a disease. The expression of other, yet to be identified, relevant genes is not detected. Another is the second type of array contains probes for genes that have very little to do with the regulation of inflammation. Also, high abundance genes are likely to be over represented and low abundance genes are likely to be under represented. The present invention provides a way to overcome such limitations.

SUMMARY OF THE INVENTION

In one aspect, the present invention provides a composition comprising a plurality of polynucleotide probes, wherein each of said polynucleotide probes comprises at least a portion of a gene implicated in blood cell biology. The plurality of polynucleotide probes can be selected from I) first polynucleotide probes, wherein each of said first polynucleotide probes comprises at least a portion of a gene differentially expressed in an immunological response; II) second polynucleotide probes, wherein each of said second polynucleotide probes comprises at least a portion of a gene abundantly expressed in an immunological response; III) third polynucleotide probes, wherein each of said third polynucleotide probes comprises at least a portion of a gene coding for a polypeptide known to regulate blood cell biology; and IV) combinations of first, second or third polynucleotide probes.

Preferably, the plurality of polynucleotide probes comprises: I) first polynucleotide probes, wherein each of said first polynucleotide probes comprises at least a portion of a gene differentially expressed in an immunological response; II) second polynucleotide probes, wherein each of said second polynucleotide probes comprises at least a portion of a gene abundantly expressed in an immunological response; and III) third polynucleotide probes, wherein each of said third polynucleotide probes comprises at least a portion of a gene coding for a polypeptide known to regulate blood cell biology.

Generally, first polynucleotide probes are selected by a) preparing at least one first target transcript profile from a first biological sample selected from the group consisting of hematopoietic cells and inflamed tissue and at least one first subtraction transcript profile from a noninflamed, nonhematopoietic biological sample; b) subtracting said first subtraction transcript profile from said first target profile to detect a plurality of genes that are differentially expressed in an immunological response; and c) identifying one of said detected genes that are differentially expressed in an immunological response. Second polynucleotide probes are selected by a) preparing at least one second target transcript profile from a second biological sample selected from the group consisting of hematopoietic cells and inflamed tissue to detect genes that are abundantly expressed in said second biological sample; and b) identifying one of said detected genes that are abundantly expressed. Third polynucleotide probes are selected by a third method comprising identifying a gene coding for a polypeptide with a known function in immunological responses.

In one preferred embodiment, the composition comprises a plurality of polynucleotide probes, wherein each polynucleotide probe comprises at least a portion of a sequence selected from the group consisting of SEQ ID Nos: 1–1508. In a second preferred embodiment, the composition comprises a plurality of polynucleotide probes comprising at least a portion of at least about 1000 of the sequences of SEQ ID Nos: 1–1508. In yet another embodiment, the composition comprises a plurality of polynucleotide probes wherein said polynucleotide probes comprise at least a portion of substantially all the sequences of SEQ ID Nos: 1–1508. The polynucleotide probes can be cDNAs, clone DNAs and the like.

The composition is particularly useful as hybridizable array elements in a microarray for monitoring the expression of a plurality of target polynucleotides. The microarray comprises a substrate and the hybridizable array elements. The microarray can be used, for example, in the diagnosis and treatment of an immunopathology.

In another aspect, the present invention provides an expression profile that can reflect the levels of a plurality of target polynucleotides in a sample. The expression profile comprises a microarray and a plurality of detectable complexes. Each detectable complex is formed by hybridization of at least one of said target polynucletodies to at least one of said polynucleotide probes and further comprises a labeling moiety for detection.

In yet another aspect, the present invention provides a method for identifying a plurality of polynucleotide probes. The method comprises selecting I) first polynucleotide probes, wherein each of said first polynucleotide probes comprises at least a portion of a gene differentially expressed in an immunological response; II) second polynucleotide probes, wherein each of said second polynucleotide probes comprises at least a portion of a gene abundantly expressed in an immunological response; and III) third polynucleotide probes, wherein each of said third polynucleotide probes comprises at least a portion of a gene coding for a polypeptide known to regulate blood cell biology.

DESCRIPTION OF THE SEQUENCE LISTING AND TABLES

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

The Sequence Listing is a compilation of nucleotide sequences obtained by sequencing clone inserts (isolates) of different cDNA libraries. Each sequence is identified by a sequence identification number (SEQ ID No:), by the clone number from which it was obtained and by the cDNA library from which the sequence was obtained.

Table 1 is a list of the sequences according to the SEQ ID Nos:. For SEQ ID Nos: 1–854 (homologous to GenBank polypeptide or nucleotide sequences), the first column contains Incyte clone numbers. The second column contains relevant GenBank Identification numbers, if any. The last column contains an annotation associated with the referenced GenBank identification numbers. For SEQ ID Nos: 855–1508 (exact matches to GenBank) the first column contains the GenBank identification number and the second column contains an annotation associated with the referenced GenBank identification number.

Table 2 is a list of the cDNA libraries and a description of the preparation of the cDNA libraries.

DESCRIPTION OF THE INVENTION

Definitions

Figure 1:
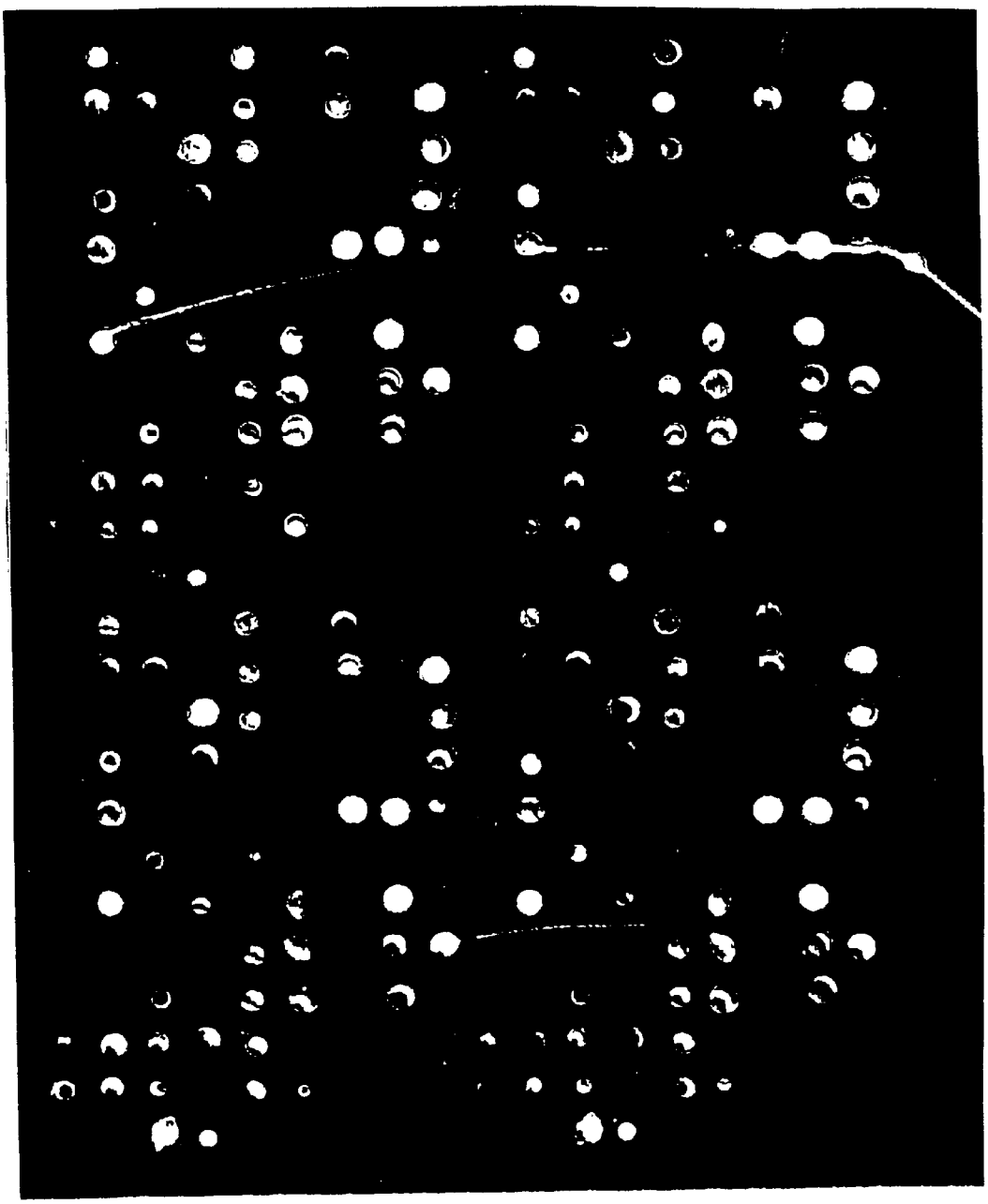
FIG. 1 is an image derived from an experiment where gene expression of untreated THP1 cells is investigated using a microarray comprising cDNA polynucleotide probes.

The term "microarray" refers to an ordered arrangement of hybridizable array elements. The array elements are arranged so that there are preferably at least one or more different array elements, more preferably at least 100 array elements, and most preferably at least 1,000 array elements, on a 1 cm² substrate surface. The maximum number of array elements is unlimited, but is at least 100,000 array elements. Furthermore, the hybridization signal from each of the array elements is individually distinguishable. In a preferred embodiment, the array elements comprise polynucleotide probes.

A "polynucleotide" refers to a chain of nucleotides. Preferably, the chain has from about 100 to 10,000 nucleotides, more preferably from about 150 to 3,500 nucleotides. The term "probe" refers to a polynucleotide sequence capable of hybridizing with a target sequence to form a polynucleotide probe/target complex. A "target polynucleotide" refers to a chain of nucleotides to which a polynucleotide probe can hybridize by base pairing. In some instances, the sequences will be complementary (no mismatches). In other instances, there may be a 10%, mismatch.

A "plurality" refers preferably to a group of at least one or more members, more preferably to a group of at least about 100, and even more preferably to a group of at least about 1,000, members. The maximum number of members is unlimited, but is at least about 100,000 members.

A "portion" means a stretch of at least about 100 consecutive nucleotides. A "portion" can also mean a stretch of at least 100 consecutive nucleotides that contains one or more deletions, insertions or substitutions. A "portion" can also mean the whole coding sequence of a gene. Preferred portions are those that lack secondary structure as identified by using computer software programs such as OLIGO 4.06 Primer Analysis is Software, (National Biosciences, Plymouth, Minn.) LASERGENE software (DNASTAR, Madison Wis., MACDASIS software (Hitachi Software Engineering Co., Ltd. South San Francisco, Calif.) and the like.

The term "gene" or "genes" refers to the partial or complete coding sequence of a gene. The phrase "genes implicated in blood cell biology" refers to genes that code for polypeptides that are known to regulate blood cell biology and genes of unknown function which are differentially or abundantly expressed in hematopoiesis or immunological responses and include those listed in the Sequence Listing and in Table 1.

The phrase "differentially expressed gene" refers to a gene whose abundance in a target transcript profile is preferably at least about 1.5×higher, more preferably about 2×higher, than that in a subtraction transcript profile. The phrase also refers to genes that are not detectable in the subtraction transcript profile but are preferably at levels of at least about 2 copies per cell, more preferably at least about 3 copies per cell, in the target transcript profile. "Abundantly expressed gene" refers to a gene which represents preferably at least about 0.01% of the transcripts in a transcript profile.

As used herein, the profile of transcripts which reflect gene expression in a particular tissue, at a particular time, is defined as a "transcript profile". Such profiles can be generated by naming, matching, and counting all copies of related clone inserts and arranging them in order of abundance. A "target transcript profile" refers to a profile derived from a biological sample that contains transcripts of interest along side transcripts which are not of interest. A "subtraction transcript profile" refers to a profile derived from a biological sample that contains predominantly transcripts that are not of interest.

The phrase "blood cell biology" encompasses hematopoeisis and all variety of immunological responses, including T cell and B cell activation, monocyte activation, and the like, and immunopathology.

"Hematopoeisis" refers to the process of blood cell growth and differentiation. "Immunological response" refers to responses elicited from blood cells including normal and immunopathological responses.

The phrase "genes coding for a polypeptide known to regulate blood cell biology" refers to genes whose known function is related to immunological responses, such as cytokines, chemokines, growth factors, transcription factors, leukotrienes, cell surface receptors, phosphatases and the like.

The term "hematopoietic cells" include erythrocytes, neutrophils, eosinophil, basophils, mast cells, megakaryocytes, platelets, monocytes, macrophages, dendritic cells, T lymphocytes, B lymphocytes, natural killer cells and the like. Furthermore, the term includes cells from tissues such as spleen, thymus, adenoid gland, fetal liver tissue and the like.

The Invention

The present invention provides a composition comprising a plurality of polynucleotide probes comprising at least a portion of genes implicated in blood cell biology. Preferably, the polynucleotide probes comprise at least a portion of one or more of the sequences (SEQ ID Nos: 1–1508) presented in the Sequence Listing. In one preferred embodiment, the composition comprises a plurality of polynucleotide probes, wherein each polynucleotide probe comprises at least a portion of a sequence selected from the group consisting of SEQ ID Nos: 1–1508. In a second preferred embodiment, the composition comprises a plurality of polynucleotide probes comprising at least a portion of at least about 1000 of the sequences of SEQ ID Nos: 1–1508. In yet another embodiment, the composition comprises a plurality of polynucleotide probes wherein said polynucleotide probes comprise at least a portion of substantially all the sequences of SEQ ID Nos: 1–1508.

The composition is particularly useful when it is used as hybridizable array elements in a microarray. Such a microarray can be employed to monitor the expression of genes of unknown function, but which are differentially or abundantly expressed in an immunological response or an immunopathology. In addition, the microarray can be used to monitor the expression of genes with a known function in blood cell biology.

The microarray can be used for large scale genetic or gene expression analysis of a large number of target polynucleotides. The microarray can be used in the diagnosis of diseases and in the monitoring of treatments where altered expression of genes implicated in blood cell biology cause disease, such as cancer, an immunopathology and the like. The microarray can also be used to investigate an individual's predisposition to a disease, such as cancer, an immunopathology and the like. Furthermore, the microarray can be employed to investigate cellular responses, such as stress responses, apoptosis, cell proliferation and the like.

When the composition of the invention is employed as hybridizable array elements in a microarray, the array elements are organized in an ordered fashion so that each element is present at a specified location on the substrate. Because the array elements are at specified locations on the substrate, the hybridization patterns and intensities (which together create a unique expression profile) can be interpreted in terms of expression levels of particular genes and can be correlated with a particular disease or condition or treatment.

The composition comprising a plurality of polynucleotide probes can also be used to purify a subpopulation of mRNAs, cDNAs, genomic fragments and the like, in a sample. Typically, samples will include the target polynucleotides of interest and other nucleic acids which may enhance the hybridization background in the sample. Therefore it may be advantageous to remove these nucleic acids. One method for removing the additional nucleic acids is by hybridizing the sample containing target polynucleotides with immobilized polynucleotide probes under hybridizing conditions. Those nucleic acids that do not hybridize to the polynucleotide probes are washed away. At a later point, the immobilized target polynucleotide probes can be released in the form of purified target polynucleotides.

Method for Selecting Polynucleotide Probes

This section describes the selection of probe sequences for the plurality of polynucleotide probes. The probe sequences are selected by identifying genes coding for polypeptides with a known function in immunological responses or genes which are abundantly or differentially expressed in specific biological samples. Since some of the probe sequences are identified solely based on expression levels, it is not essential to know a priori the function of a particular gene in blood cell biology.

The selection method is based, in part, on expression sequence tag (EST) analysis. EST analysis entails sequencing, in whole or in part, isolated clone inserts from a complementary DNA (cDNA) library, clustering overlapping sequences and determining the clustered sequences' frequency in the cDNA library.

ESTs are sequenced by methods well known in the art. The methods can employ such enzymes as the Klenow fragment of DNA polymerase I, Taq polymerase, thermostable T7 polymerase, or combinations of polymerases and proofreading exonucleases. Preferably, the process is automated. ESTs derived from the same transcript can be combined to form a cluster of ESTs. Clusters are formed by identifying overlapping EST sequences and assembling the ESTs. A nucleic acid fragment assembly tool, such as the PHRAP tool (WashU-Merck) and the GELVIEW Fragment Assembly system (Genetics Computer Group, Madison, Wis.), can be used for this purpose. Clones can be arranged in clusters in descending order of abundance. The minimum number of clones necessary to constitute a cluster is two.

After assembling EST clusters, a transcript profile for a particular biological sample is generated and the frequency or abundance of a given EST cluster can be determined. The frequency of an EST cluster in a clone population is correlated to the level of expression of a particular gene. By this process those genes that are abundantly expressed in a biological sample can be identified.

Furthermore, EST analysis can be employed to identify genes that are differentially expressed in one biological sample (from which a target cDNA library and a target transcript profile are derived) but not in another biological sample (from which a subtraction cDNA library and a subtraction transcript profile are derived). For this purpose, transcript profiles from both biological samples are generated compared. By comparing transcript profiles, those genes that are differentially expressed in a target biological sample can be identified.

With a large enough number of transcript profiles derived from different biological samples, a statistically significant correlation can emerge between cell and tissue source information, such as disease states, treatment outcomes, exposure to various environmental factors or genotypes, and the expression levels of particular genes or groups of genes. Comparisons between transcript profiles of different cells or tissues or of the same cells or tissues under different conditions can be used to discern differences in transcriptional activities. For example, a transcript profile can show differences occurring between two different tissues, such as liver and prostate; between normal and diseased tissue, such as normal and prostate tumor or between untreated and treated tissues, such as prostate tumor and irradiated prostate tumor.

The biological samples from which transcript profiles are derived can be from a variety of sources. For purposes of this invention, since the intent is to select polynucleotide probes useful for investigating gene expression as it relates to blood cell biology, biological samples include those derived from hematopoietic and inflamed samples and nonhematopoietic, noninflamed biological samples.

In particular, where probe sequences are derived from genes differentially expressed in an immunological response, the transcript profiles of hematopoietic cells or tissues associated with an immunological response (normal or inflamed) are compared to those of noninflamed nonhematopoietic samples. Examples of hematopoietic cells or tissues associated with an immunological response include inflamed adenoid, bone marrow, macrophages, lymphocytes, granulocytes, spleen, tonsil, eosinophil, asthmatic lung tissue, diabetic pancreas, colon tissue derived from an individual suffering from Crohn's disease and the like. Examples of noninflamed nonhematopoietic tissue include fibroblasts, keratinocytes, fetal lung, brain, melanocytes and the like. Only those genes that are differentially expressed, i.e., the transcript levels are preferably at least about 1.5×higher, more preferably at least about 2×higher, in hematopoietic sample than that in the nonhematopoietic sample, are selected. Additionally, genes that are not detectable in the nonhematopoietic sample but which have transcript levels of preferably at least about two (2) copies per cell, more preferably at least about three (3) copies per cell, in the hematopoietic sample are selected.

Where probe sequences are derived from genes that are abundantly expressed in an immunological response, the transcript profiles of hematopoietic cells or tissues associated with an inflammatory process are obtained. Only those genes whose transcripts represent preferably at least 0.01% of the transcripts in a biological sample are selected.

For purposes of this invention, transcript profile comparisions can be obtained by methods well known to those skilled in the art. Transcript levels and profiles can be obtained and compared, for example, by a differential gene expression assay based on a quantitative hybridization of arrayed cDNA clones (Nguyen, et al. (1995) *Genomics* 29: 207–216), based on the serial analysis of gene expression (SAGE) technology (Velculescu et al. (1995) *Science* 270: 484–487), based on the polymerase chain reaction (Peng et al. (1992) *Science* 257: 967–971, Prashar et al. (1996) *Proc. Natl. Acad. Sci. USA* 93: 659–663), by a differential amplification protocol (Van Gelder et al. 5,545,522), or based on electronic analysis, such as the Lifeseq® Transcript Imaging tool (Incyte Pharmaceuticals, Palo Alto, Calif. hereinafter Incyte) or the GeneCalling and Quantitative Expression Analysis technology (Curagen, New Haven, Conn.) Comparisons (subtractions) between two of more transcript profiles are preferably performed electronically using the Lifeseq® Multiple Transcript Subsetting tool (Incyte).

Selection Protocols The method of selecting polynucleotide probe sequences is based on three selection protocols. The polynucleotide probes of the composition can be selected by employing any one of these three selection protocols, the combination of any two of these protocols, or all the protocols.

A first selection protocol (I) can provide for first polynucleotide probes derived from genes differentially expressed in an immunological response. A number of target cDNA libraries are prepared from first biological samples. The first biological sample can be hematopoietic cells or tissues associated with an immunological response, such as inflamed tissues. Preferably at least one cDNA library, more preferably at least four cDNA libraries, are selected from hematopoietic cells or tissues associated with an immunological response. First target transcript profiles are generated from each of the libraries. Transcript profiles can be combined to obtain an averaged transcript profile. An averaged transcript profile entails adding up the transcript abundances for each transcript from each biological sample and then dividing summed up transcript abundances by the total number of biological samples.

A number of subtraction cDNA libraries are prepared from biological samples that are noninflamed and nonhematopoietic. Preferably at least one cDNA library, more preferably at least four cDNA libraries, are selected from noninflamed nonhematopoietic biological samples. First subtraction transcript profiles are generated from these cDNA libraries. Preferably, these transcript profiles are combined to obtain an averaged transcript profile.

In one embodiment, the averaged transcript image from the subtraction cDNA libraries is subtracted from each target cDNA library. In another embodiment, the averaged transcript image from the subtraction cDNA libraries is subtracted from an averaged transcript image of the target cDNA libraries.

In either case, a transcript profile is obtained showing the genes that are differentially expressed in biological samples consisting of hematopoietic cells or tissues associated with an immunological response rather than with noninflamed and nonhematopoietic biological samples. In one embodiment, the top 100 most abundant transcripts, more preferably the top 40 most abundant transcripts, are selected to generate first polynucleotide probes. In a second embodiment, all upregulated transcripts are selected. By upregulated is meant that the genes are not detectable in the subtraction transcript profile but are preferably at levels of at least about 2 copies per cell, more preferably at least about 3 copies per cell, in the target transcript profile.

A second selection protocol (II) can provide for second polynucleotide probes derived from genes abundantly expressed in an immunological-response. A number of target cDNA libraries are prepared from second biological samples. The second biological sample can be hematopoietic cells or tissues associated with an inflammatory process (normal or diseased). Preferably at least one cDNA library, more preferably at least four cDNA libraries, are selected from hematopoietic cells or tissues associated with an inflammatory process. Third transcript profiles are generated from such libraries. The transcripts are ranked according to abundance. Those transcripts that are most abundant are selected. Preferably the top 100 most abundant transcripts are selected from the remaining transcripts, more preferably the top 40 most abundant transcripts, including the top 20 novel sequences (i.e., not in a public database), can be selected to generate second polynucleotide probes.

In a third selection protocol (III) the literature is surveyed and sequences in GenBank and Lifeseq® database (Incyte) screened to identify genes coding for polypeptides whose function is related to immunological responses. These genes can be selected to generate third polynucleotide probes.

The resulting composition can comprise polynucleotide probes that are not redundant, i.e., there is no more than one polynucleotide probe to represent a particular gene. Alternatively, the composition can contain polynucleotide probes that are redundant, i.e., a gene is represented by more than one polynucleotide probe.

The selected polynucleotide probes may be manipulated further to optimize the performance of the polynucleotide probes as hybridization probes.

Some probes may not hybridize effectively under hybridization conditions due to secondary structure. To optimize probe hybridization, the probe sequences are examined using a computer algorithm to identify portions of genes without potential secondary structure. Such computer algorithms are well known in the art such as OLIGO 4.06 Primer Analysis Software (National Biosciences) or LASERGENE software (DNASTAR). These programs can search nucleotide sequences to identify stem loop structures and tandem repeats and to analyze G+C content of the sequence (those sequences with a G+C content greater than 60% are excluded). Alternatively, the probes can be optimized by trial and error. Experiments can be performed to determine whether probes and complementary target polynucleotides hybridize optimally under experimental conditions.

Where the number of different polynucleotide probes is desired to be greatest, the probe sequences are extended to assure that different polynucleotide probes are not derived from the same gene, i.e., the polynucleotide probes are not redundant. The probe sequences may be extended utilizing the partial nucleotide sequences derived from EST sequencing by employing various methods known in the art. For example, one method which may be employed, "restriction-site" PCR, uses universal primers to retrieve unknown sequence adjacent to a known locus (Sarkar, G. (1993) *PCR Methods Applic.* 2: 318–322).

Polynucleotide Probes

This section describes the polynucleotide probes. The polynucleotide probes can be DNA or RNA, or any RNA-like or DNA-like material, such as peptide nucleic acids, branched DNAs and the like. The polynucleotide probes can be sense or antisense polynucleotide probes. Where target polynucleotides are double stranded, the probes may be either sense or antisense strands. Where the target polynucleotides are single stranded, the nucleotide probes are complementary single strands.

In one embodiment, the polynucleotide probes are cDNAs. The size of the DNA sequence of interest may vary, and is preferably from about 100 to 10,000 nucleotides, more preferably about from 150 to 3,500 nucleotides.

In a second embodiment, the polynucleotide probes are clone DNAs. In this case, the size of the DNA sequence of interest, i.e., the insert sequence excluding the vector DNA, may vary from 100 to 10,000 nucleotides, more preferably from 150 to 3,500 nucleotides.

The polynucleotide probes can be prepared by a variety of synthetic or enzymatic schemes which are well known in the art. The probes can be synthesized, in whole or in part, using chemical methods well known in the art. (Caruthers et al. (1980) *Nucleic. Acids Symp. Ser.* (2) 215–233). Alternatively, the probes can be generated, in whole or in part, enzymatically.

Nucleotide analogues can be incorporated into the polynucleotide probes by methods well known in the art. The only requirement is that the incorporated nucleotide analogues must serve to base pair with target polynucleotide sequences. For example, certain guanine nucleotides can be substituted with hypoxanthine which base pairs with cytosine residues. However, these base pairs are less stable than those between guanine and cytosine. Alternatively, adenine nucleotides can be substituted with 2,6-diaminopurine which can form stronger base pairs than those between adenine and-thymidine.

Additionally, the polynucleotide probes can include nucleotides that have been derivatized chemically or enzymatically. Typical chemical modifications include derivatization with acyl, alkyl, aryl or amino groups.

The polynucleotide probes can be immobilized on a substrate. Preferred substrates are any suitable rigid or semirigid support including membranes, filters, chips, slides, wafers, fibers, magnetic or nonmagnetic beads, gels, tubing, plates, polymers, microparticles and capillaries. The substrate can have a variety of surface forms, such as wells, trenches, pins, channels and pores, to which the polynucleotide probes are bound. Preferably, the substrates are optically transparent.

Probes can be synthesized, in whole or in part, on the surface of a substrate by using a chemical coupling procedure and a piezoelectric printing apparatus, such as that described in PCT publication WO95/251116 (Baldeschweiler et al.). Alternatively, the probe can be synthesized using a self-addressable electronic device that controls when reagents are added (Heller et al. U.S. Pat. No. 5,605,662) or by photolysis using imaging fibers for light delivery (Healey et al. (1995) *Science* 269: 1078–80).

Complementary DNA (cDNA) can be arranged and then immobilized on a substrate. The probes can be immobilized by covalent means such as by chemical bonding procedures or UV. In one such method, a cDNA is bound to a glass surface which has been modified to contain epoxide or aldehyde groups. In another case, a cDNA probe is placed on a polylysine coated surface and then UV cross-linked (Shalon et al. PCT publication WO95/35505, herein incorporated by reference). In yet another method, a DNA is actively transported from a solution to a given position on a substrate by electrical means (Heller et al. U.S. Pat. No. 5,605,662). Alternatively, individual DNA clones can be gridded on a filter. Cells are lysed, proteins and cellular components degraded and the DNA coupled to the filter by UV cross-linking.

Furthermore, the probes do not have to be directly bound to the substrate, but rather can be bound to the substrate through a linker group. The linker groups are typically about 6 to 50 atoms long to provide exposure to the attached polynucleotide probe. Preferred linker groups include ethylene glycol oligomers, diamines, diacids and the like. Reactive groups on the substrate surface react with one of the terminal portions of the linker to bind the linker to the substrate. The other terminal portion of the linker is then functionalized for binding the polynucleotide probe.

The polynucleotide probes can be attached to a substrate by dispensing reagents for probe synthesis on the substrate surface or by dispensing preformed DNA fragments or clones on the substrate surface. Typical dispensers include a micropipette delivering solution to the substrate with a robotic system to control the position of the micropipette with respect to the substrate. There can be a multiplicity of dispensers so that reagents can be delivered to the reaction regions simultaneously.

Sample Preparation

In order to conduct sample analysis, a sample containing target polynucleotides is provided. The samples can be any sample containing target polynucleotides and obtained from any bodily fluid (blood, urine, saliva, phlegm, gastric juices, etc.), cultured cells, biopsies, or other tissue preparations.

DNA or RNA can be isolated from the sample according to any of a number of methods well known to those of skill in the art. For example, methods of purification of nucleic acids are described in *Laboratory Techniques in Biochemistry and Molecular Biology: Hybridization With Nucleic Acid Probes, Part I. Theory and Nucleic Acid Preparation*, P. Tijssen, ed. Elsevier, New York, N.Y. (1993). In one case, total RNA is isolated using the TRIZOL total RNA isolation reagent (Life Technologies, Gaithersburg, Md.) and mRNA is isolated using oligo d(T) column chromatography or glass beads. Alternatively, when target polynucleotides are derived from an mRNA, the target polynucleotides can be a cDNA reverse transcribed from an mRNA, an RNA transcribed from that cDNA, a DNA amplified from that cDNA, an RNA transcribed from the amplified DNA, and the like. When the target polynucleotide is derived from DNA, the target polynucleotide can be DNA amplified from DNA or RNA reverse transcribed from DNA. In yet another alternative, the targets are target polynucleotides prepared by more than one method.

When target polynucleotides are amplified it is desirable to amplify the nucleic acid sample and maintain the relative abundances of the original sample, including low abundance transcripts. Total mRNA can be amplified by reverse transcription using a reverse transcriptase and a primer consisting of oligo d(T) and a sequence encoding the phage T7 promoter to provide a single stranded DNA template. The second cDNA strand is polymerized using a DNA polymerase and a RNAse which assists in breaking up the DNA/RNA hybrid. After synthesis of the double stranded cDNA, T7 RNA polymerase can be added and RNA transcribed from the second cDNA strand template (Van Gelder et al. U.S. Pat. No. 5,545,522). RNA can be amplified in vitro, in situ or in vivo (See Eberwine, U.S. Pat. No. 5,514,545).

It is also advantageous to include quantitation controls within the sample to assure that amplification and labeling procedures do not change the true distribution of target polynucleotides in a sample. For this purpose, a sample is spiked with a known amount of a control target polynucleotide and the composition of polynucleotide probes includes reference polynucleotide probes which specifically hybridize with the control target polynucleotides. After hybridization and processing, the hybridization signals obtained should reflect accurately the amounts of control target polynucleotide added to the sample.

Prior to hybridization, it may be desirable to fragment the nucleic acid target polynucleotides. Fragmentation improves hybridization by minimizing secondary structure and cross-hybridization to other nucleic acid target polynucleotides in the sample or noncomplementary polynucleotide probes. Fragmentation can be performed by mechanical or chemical means.

The target polynucleotides may be labeled with one or more labeling moieties to allow for detection of hybridized probe/target polynucleotide complexes. The labeling moieties can include compositions that can be detected by spectroscopic, photochemical, biochemical, bioelectronic, immunochemical, electrical, optical or chemical means. The labeling moieties include radioisotopes, such as $^{32}$p, $^{33}$p or $^{35}$S, chemiluminescent compounds, labeled binding proteins, heavy metal atoms, spectroscopic markers, such as fluorescent markers and dyes, magnetic labels, linked enzymes, mass spectrometry tags, spin labels, electron transfer donors and acceptors, and the like.

Exemplary dyes include quinoline dyes, triarylmethane dyes, phthaleins, azo dyes, cyanine dyes and the like. Preferably, fluorescent markers absorb light above about 300 nm, preferably above 400 nm, and usually emit light at wavelengths at least greater than 10 nm above the wavelength of the light absorbed. Specific preferred fluorescent markers include fluorescein, phycoerythrin, rhodamine, lissamine, and Cy3 and Cy5 available from Amersham Pharmacia Biotech (Piscataway, N.J.).

Labeling can be carried out during an amplification reaction, such as polymerase chain and in vitro transcription reactions, or by nick translation or 5' or 3'-end-labeling reactions. In one case, labeled nucleotides are used in an in vitro transcription reaction. When the label is incorporated after or without an amplification step, the label is incorporated by using terminal transferase or by kinasing the 5' end of the target polynucleotide and then incubating overnight with a labeled oligonucleotide in the presence of T4 RNA ligase.

Alternatively, the labeling moiety can be incorporated after hybridization once a probe/target complex has formed. In one case, biotin is first incorporated during an amplification step as described above. After the hybridization reaction, unbound nucleic acids are rinsed away so that the only biotin remaining bound to the substrate is that attached to target polynucleotides that are hybridized to the polynucleotide probes. Then, an avidin-conjugated fluorophore, such as avidin-phycoerythrin, that binds with high affinity to biotin is added. In another case, the labeling moiety is incorporated by intercalation into preformed target/polynucleotide probe complexes. In this case, an intercalating dye such as a psoralen-linked dye can be employed.

Under some circumstances it may be advantageous to immobilize the target polynucleotides on a substrate and have the polynucleotide probes bind to the immobilized target polynucleotides. In such cases the target polynucleotides can be attached to a substrate as described above.

Hybridization and Detection

Hybridization causes a denatured polynucleotide probe and a denatured complementary target to form a stable duplex through base pairing. Hybridization methods are well known to those skilled in the art (See, for example, *Laboratory Techniques in Biochemistry and Molecular Biology, Vol. 24: Hybridization With Nucleic Acid Probes*, P. Tijssen, ed. Elsevier, New York, N.Y. (1993)). Conditions can be selected for hybridization where exactly complementary target and polynucleotide probe can hybridize, i.e., each base pair must interact with its complementary base pair. Alternatively, conditions can be selected where target and polynucleotide probes have mismatches but are still able to hybridize. Suitable conditions can be selected, for example, by varying the concentrations of salt or formamide in the prehybridization, hybridization and wash solutions, or by varying the hybridization and wash temperatures.

Hybridization can be performed at low stringency with buffers, such as 6×SSPE with 0.005% Triton X-100 at 37° C., which permits hybridization between target and polynucleotide probes that contain some mismatches to form target polynucleotide/probe complexes. Subsequent washes are performed at higher stringency with buffers, such as 0.5×SSPE with 0.005% Triton X-100 at 50° C., to retain hybridization of only those target/probe complexes that contain exactly complementary sequences. Alternatively, hybridization can be performed with buffers, such as 5×SSC/0.2% SDS at 60° C. and washes are performed in 2×SSC/0.2% SDS and then in 0.1×SSC. Stringency can also be increased by adding agents such as formamide. Background signals can be reduced by the use of detergent, such as sodium dodecyl sulfate, Sarcosyl or Triton X-100, or a blocking agent, such as sperm DNA.

Hybridization specificity can be evaluated by comparing the hybridization of specificity-control polynucleotide probes to specificity-control target polynucleotides that are added to a sample in a known amount. The specificity-control target polynucleotides may have one or more sequence mismatches compared with the corresponding polynucleotide probes. In this manner, whether only complementary target polynucleotides are hybridizing to the polynucleotide probes or whether mismatched hybrid duplexes are forming is determined.

Hybridization reactions can be performed in absolute or differential hybridization formats. In the absolute hybridization format, target polynucleotides from one sample are hybridized to the probes in a microarray format and signals detected after hybridization complex formation correlate to target polynucleotide levels in a sample. In the differential hybridization format, the differential expression of a set of genes in two biological samples is analyzed. For differential hybridization, target polynucleotides from both biological samples are prepared and labeled with different labeling moieties. A mixture of the two labeled target polynucleotides is added to a microarray. The microarray is then examined under conditions in which the emissions from the two different labels are individually detectable. Probes in the microarray that are hybridized to substantially equal numbers of target polynucleotides derived from both biological samples give a distinct combined fluorescence (Shalon et al. PCT publication WO95/35505). In a preferred embodiment, the labels are fluorescent labels with distinguish-able emission spectra, such as a lissamine conjugated nucleotide analog and a fluorescein conjugated nucleotide-analog. In another embodiment Cy3/Cy5 fluorophores (Amersham Pharmacia Biotech) are employed.

After hybridization, the microarray is washed to remove nonhybridized nucleic acids and complex formation between the hybridizable array elements and the target polynucleotides is detected.

Methods for detecting complex formation are well known to those skilled in the art. In a preferred embodiment, the target polynucleotides are labeled with a fluorescent label and measurement of levels and patterns of fluorescence indicative of complex formation is accomplished by fluorescence microscopy, preferably confocal fluorescence microscopy. An argon ion laser excites the fluorescent label, emissions are directed to a photomultiplier and the amount of emitted light detected and quantitated. The detected signal should be proportional to the amount of probe/target polynucleotide complex at each position of the microarray. The fluorescence microscope can be associated with a computer-driven scanner device to generate a quantitative two-dimensional image of hybridization intensity. The scanned image is examined to determine the abundance/expression level of each hybridized target polynucleotide.

In a differential hybridization experiment, target polynucleotides from two or more different biological samples are labeled with two or more different fluorescent labels with different emission wavelengths. Fluorescent signals are detected separately with different photomultipliers set to detect specific wavelengths. The relative abundances/expression levels of the target polynucleotides in two or more samples is obtained.

Typically, microarray fluorescence intensities can be normalized to take into account variations in hybridization intensities when more than one microarray is used under similar test conditions. In a preferred embodiment, individual polynucleotide probe/target complex hybridization intensities are normalized using the intensities derived from internal normalization controls contained on each microarray.

Expression Profiles

This section describes an expression profile using the composition of this invention. The expression profile can be used to detect changes in the expression of genes implicated in blood cell biology. These genes include genes whose altered expression is correlated with cancer, immunopathology, apoptosis and the like.

The expression profile comprises the polynucleotide probes of the invention. The expression profile also includes a plurality of detectable complexes. Each complex is formed by hybridization of one or more polynucleotide probes to one or more complementary target polynucleotides. At least one of the polynucleotide probes, preferably a plurality of polynucleotide probes, is hybridized to a complementary target polynucleotide forming, at least one, preferably a plurality of complexes. A complex is detected by incorporating at least one labeling moiety in the complex. The labeling moiety has been described above.

The expression profiles provide "snapshots" that can show unique expression patterns that are characteristic of a disease or condition.

Utility of the Invention

The composition comprising a plurality of polynucleotide probes can be used as hybridizable elements in a microarray. Such a microarray can be employed in several applications including diagnostics, prognostics and treatment regimens, drug discovery and development, toxicological and carcinogenicity studies, forensics, pharmacogenomics and the like.

In one situation, the microarray is used to monitor the progression of disease. Researchers can assess and catalog the differences in gene expression between healthy and diseased tissues or cells. By analyzing changes in patterns of gene expression, disease can be diagnosed at earlier stages before the patient is symptomatic.

Similarly, the invention can be used to monitor the progression of disease or the efficacy of treatment. For some treatments with known side effects, the microarray is employed to "fine tune" the treatment regimen. A dosage is established that causes a change in genetic expression patterns indicative of successful treatment. Expression patterns associated with undesirable side effects are avoided. This approach may be more sensitive and rapid than waiting for the patient to show inadequate improvement, or manifest symptoms, before altering the course of treatment.

Alternatively, animal models which mimic a disease, rather than patients, can be used to characterize expression profiles associated with a particular disease or condition. For example, a characteristic gene expression pattern for the graft versus host reaction can be generated using analogous reactions that occur when lymphocytes from one donor are mixed with lymphocytes from another donor. This gene expression data may be useful in diagnosing and monitoring the course of graft versus host reaction in a patient, in determining gene targets for intervention, and in testing novel immunosuppressants.

The composition is particularly useful for diagnosing and monitoring the progression of diseases that are associated with the altered expression of genes implicated in blood cell biology. The expression of these genes is associated with cellular processes such as hematopoiesis, immunological responses, immunopathology, cell proliferation, apoptosis, and the like. Thus, the microarray is particularly useful to diagnose immunopathologies including, but not limited to, AIDS, Addison's disease, adult respiratory distress syndrome, allergies, anemia, asthma, atherosclerosis, bronchitis, cholecystitus, Crohn's disease, ulcerative colitis, atopic dermatitis, dermatomyositis, diabetes mellitus, emphysema, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, and autoimmune thyroiditis;viral, bacterial, fungal, parasitic, and protozoal infections and trauma.

The invention also allows researchers to develop sophisticated profiles of the effects of currently available therapeutic drugs. Tissues or cells treated with these drugs can be analyzed and compared to untreated samples of the same tissues or cells. In this way, an expression profile of known therapeutic agents will be developed. Knowing the identity of sequences that are differentially regulated in the presence and absence of a drug will allow researchers to elucidate the molecular mechanisms of action of that drug.

Also, researchers can use the microarray to rapidly screen large numbers of candidate drugs, looking for ones that have an expression profile similar to those of known therapeutic drugs, with the expectation that molecules with the same expression profile will likely have similar therapeutic effects. Thus, the invention provides the means to determine the molecular mode of action of a drug.

It is understood that this invention is not limited to the particular methodology, protocols, and reagents described, as these may vary. It is also understood that the terminology used herein is for the purpose of describing particular embodiments only, and is not intended to limit the scope of the present invention which will be limited only by the appended claims. The examples below are provided to illustrate the subject invention and are not included for the purpose of limiting the invention.

EXAMPLES

I cDNA Library Construction

For purposes of example, the preparation and sequencing of the LNODNOT03 cDNA library, from which Incyte Clones 1573272, 1573553, 1574415, 1574617, 1574637, and 1576661 were isolated, is described in detail. Preparation and sequencing of cDNA libraries in the LifeSeq® database (Incyte) have varied over time, and the gradual changes involved use of kits, plasmids, and machinery available at the particular time the library was made and analyzed.

The LNODNOT03 cDNA library was constructed from microscopically normal lymph node tissue excised from a 67-year-old Caucasian male. This tissue was associated with tumorous lung tissue. The patient history included squamous cell carcinoma of the lower lobe, benign hypertension, arteriosclerotic vascular disease, and tobacco abuse. The patient was taking Doxycycline, a tetracycline, to treat an infection.

The frozen tissue was homogenized and lysed using a POLYTRON homogenizen PT-3000 (Brinkmann Instruments, Westbury, N.J.) in guanidinium isothiocyanate solution. The lysate was centrifuged over a 5.7 M CsCl cushion using an SW28 rotor in a L8-70M Ultracentrifuge (Beckman Coulter Fullerton, Calif.) for 18 hours at 25,000 rpm at ambient temperature. The RNA was extracted with acid phenol pH 4.7, precipitated using 0.3 M sodium acetate and 2.5 volumes of ethanol, resuspended in RNAse-free water, and DNase treated at 37° C. The RNA extraction was repeated with acid phenol pH 4.7 and precipitated with sodium-acetate and ethanol as before. The mRNA was then isolated using the OLIGO.TEX kit (QIAGEN, Inc., Chatsworth, Calif.) and used to construct the cDNA library.

The mRNA was handled according to the recommended protocols in the SUPERSCRIPT Plasmid, System for cDNA Synthesis and Plasmid Cloning (Life Technologies). cDNAs were fractionated on SEPHAROSE CL4B column (Amersham Pharmacia Biotech), and those cDNAs exceeding 400 BP were ligated into pSPORT I. The plamid PSORT I plasmid (Life Technologies) was subsequently transformed into DH5a competent cells (Life Technologies).

II cDNA Library Normalization

In some cases, cDNA libraries have been normalized in a single round according to the procedure of Soares et al. ((1994), Proc. Natl. Acad. Sci. USA 91: 9928–9932) with the following modifications. The primer to template ratio in the primer extension reaction was increased from 2:1 to 10:1. The dNTP concentration in the reaction was reduced to 150 $\mu$M each dNTP, allowing the generation of longer (400–1000 nt) primer extension products. The reannealing hybridization was extended from 13 to 19 hours. The single stranded DNA circles of the normalized library were purified by hydroxyapatite chromatography and converted to partially double-stranded by random priming, followed by electroporation into DH10B competent bacteria (Life Technologies).

The Soares normalization procedure is designed to reduce the initial variation in individual cDNA frequencies to achieve abundances within one order of magnitude while maintaining the overall sequence complexity of the library. In the normalization process, the prevalence of high-abundance cDNA clones decreases significantly, clones with mid-level abundance are relatively unaffected, and clones for rare transcripts are effectively increased in abundance. In the modified Soares normalization procedure, significantly longer hybridization times are used which allows for the increase of gene discovery rates by biasing the normalized libraries toward low-abundance cDNAs that are well represented in a standard transcript image.

III Isolation and Sequencing of cDNA Clones

Plasmid cDNA was released from the cells and purified using the REAL Prep 96 plasmid kit (Catalog #26173, QIAGEN). The recommended protocol was employed except for the following changes: 1), the bacteria were cultured in 1 ml of sterile Terrific Broth (Life Technologies) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

cDNAs were sequenced according to the method of Sanger et al. ((1975) J. Mol. Biol. 94: 441f), using the Perkin Elmer Catalyst 800 or a MICROLAB 2200 (Hamilton, Reno, Nev.) in combination with DNA ENGINE Thermal Cyclers (PTC200 from MJ Research, Watertown, Mass.) and ABI PRISM 377 on 373 DNA Sequencing Systems (PE Biosystems, Foster City, Calif.) and the reading frame was determined.

IV Homology Searching of cDNA Clones and Their Deduced Proteins

As used herein, "homology" refers to sequence similarity between a reference sequence and at least a portion of a newly sequenced clone insert, and can refer to either a nucleic acid or amino acid sequence. The Genbank databases which contain previously identified and annotated sequences, were searched for regions of homology using BLAST (Basic Local Alignment Search Tool). (See, e.g., Altschul, S. F. (1993) J. Mol. Evol. 36: 290–300; and Altschul et al. (1990) J. Mol. Biol. 215: 403–410.)

BLAST involves first finding similar segments between the query sequence and a database sequence, then evaluating the statistical significance of any matches that are found and finally reporting only those matches that satisfy a user-selectable threshold of significance. BLAST produces alignments of both nucleotide and amino acid sequences to determine sequence similarity. The fundamental unit of the BLAST algorithm output is the High scoring Segment Pair (HSP). An HSP consists of two sequence fragments of arbitrary, but equal lengths, whose alignment is locally maximal and for which the alignment score meets or exceeds a threshold or cutoff score set by the user.

The basis of the search is the product score, which is defined as:

$$\frac{\% \text{ sequence identity} \times \% \text{ maximum BLAST score}}{100}$$

The product score takes into account both the degree of similarity (identity) between two sequences and the length of the sequence match as reflected in the BLAST score. The BLAST score is calculated by scoring +5 for every base that matches in an HSP and −4 for every mismatch. For example, with a product score of 40, the match will be exact within a 1% to 2% error, and, with a product score of 70, the match will be exact. Homologous molecules are usually identified by selecting those which show product scores between 15 and 40, although lower scores may identify related molecules. The P-value for any given HSP is a function of its expected frequency of occurrence and the number of HSPs observed against the same database sequence with scores at least as high.

V Transcript Imaging

Transcript profiles were generated using the Lifeseq® Transcript Imaging tool (Incyte). To identify genes that are differentially expressed in hematopoietic or inflamed biological samples, reverse transcript profiles from specific target cDNA library pools derived from either hematopoietic or inflamed biological samples were obtained. The number of cDNA libraries in a cDNA library pool varied from one cDNA library member to 6 cDNA library members. For library pools which contained more than one member, an averaged reverse transcript image was obtained. The target library pools were the following: 1. ADENINB01; 2. COLSUCT01, COLNNOT23, SINTNOT13; 3. COLNCRT01, COLNNOT27, SINTBST01; 4. ENDCNOT01, ENDCNOT02, ENDCNOT03, HUVELPB01, HUVENOB01, HUVESTB01; 5. EOSIHET02, UCMCL5T01; 6. HMC1NOT01; 7. LNODNOT02, LNODNOT03; 8. LUNGAST01; 9. MMLR1DT01, MMLR2DT01, MMLR3DT01; 10. NEUTFMT01, NEUTGMT01, NEUTLPT01; 11. PANCDIT01, 12. TONSNOT01; 13. SYNOOAT01; 14. SYNORAB01, SYNORAT01, SYNORAT03, SYNORAT04, SYNORAT05; 15. THP1PLB01, THP1PLB02; and 16. TMLR2DT01, TMLR3DT01, TMLR3DT02.

Reverse transcript profiles were also derived from 39 subtraction cDNA libraries which were derived from predominantly nonhematopoetic noninflamed biological samples. The following is a list of the cDNA libraries: FIBRAGT01, FIBRAGT02, FIBRANT01, FIBRNGT01, FIBRNGT02, FIBRSEM01, KERANOT01, COLNNOM01, COLNTUM01, EYECNOM01, FIBRFEM01, HNT2NOM01, OVARTUM02, PANCTUM01, UTRPNOM01, CARDFEM01, FIBRSEM01, PANCISM01, LUNGFEM01, PTHYTUM01, BRAINOM01, BRAINOM02, BRAINOM03, BRSTNOM01, BRSTNOM02, COCHFEM01, LIVRNOM01, LUNGNOM01, MELANOM01, NERVMSM01, OLFENOM01, OVARNOM01, OVARTUM01, PINENOM01, PLACNOM01, PLACNOM02, PLACNOM03, RETNNOM01, and RETNNOM02. In some cases, one or more subtraction libraries were derived from hematopoietic or inflamed biological samples, such as the NERVMSM01 library derived from the tissue of a patient suffering from multiple sclerosis. An averaged subtraction transcript profile was obtained by poling the transcript information from all 39 libraries.

The LifeSeq® Multiple Transcript Subsetting tool (Incyte) was used to subtract the averaged subtraction transcript profile from each target cDNA library pool. A list of subtracted transcripts which consisted of clustered ESTs was generated. The subtracted transcripts were ranked according to abundance. The 40 most abundant transcripts were selected from each set of subtracted library pools.

To identify additional genes that are differentially expressed in immunological responses, reverse transcript profiles from specific target cDNA libraries derived from inflamed biological samples were obtained. Subtraction cDNA library transcript profiles were generated from healthy counterparts. In some cases the subtraction transcript profile was created by averaging transcript images from a pool of cDNA libraries. Target and subtraction cDNA libraries are listed in the following table.

| TARGET LIBRARY | SUBTRACTION LIBRARIES |
| --- | --- |
| LUNGAST01 | LUNGFEMO1, LUNGFET03, LUNGNOM01, LUNGNOTO1, LUNGNOT02, LUNGNOT03, LUNGNOT04, LUNGNOT09, LUNGNOT10, LUNGNOT12, LUNGNOT14, LUNGNOT15, LUNGNOT18, LUNGNOT20 |
| COLNCRT01 | COLNNOT05 |
| HUVELPBO1 | HUVENOB01, HUVESTB01 |
| PANCDIT01 | PANCNOT01, PANCNOT04, PANCNOT05 |

A list of subtracted transcripts which consisted of clustered ESTs was generated. After subtracting transcript profiles, all upregulated sequences were selected.

To identify novel genes that are abundantly expressed in an immunological response, 43 cDNA libraries derived from hematopoietic or inflamed biological samples were picked. These libraries were: ADENINB01, AMLBNOT01, BMARNOR02, BMARNOT02, BMARNOT03, EOSIHET02, HMC1NOTO01, LEUKNOT02, LEUKNOT03, LNODNOT02, LNODNOT03, MMLR1DT01, MMLR2DT01, MMLR3DT01, MPHGLPT02, MPHGNOT02, MPHGNOT03, NEUTFMT01, NEUTGMT01, NEUTLPT01, THYMNOT02, TLYMNOT01, TLYMNOT02, TMLR2DT01, TMLR3DT01, TMLR3DT02, SPLNFET01, SPLNFET02, SPLNNOT02, SPLNNOT04, TBLYNOT01, THP1NOB01, THP1NOT01, THP1NOT03, THP1AZT01, THP1PEB01, THP1PLB01, THP1PLB02, THP1T7T01, TONSNOT01, U937NOT01, UCMCL5T01, and UCMCNOT02.

Reverse transcript profiles were generated from the 43 cDNA libraries using a product score of 100 as the maximum cutoff. Using this setting returns all the sequences in the transcript profile. The top most abundant sequences were selected. Reverse transcript profiles were also generated from the chosen libraries using a product score of 70 as the maximum cutoff. This procedure effectively removed exact matches to gene sequences found in GenBank. A list of transcripts which consisted of clustered ESTs was generated. The top 20 most abundant sequences were selected.

To identify genes known to be associated with the regulation of blood cell biology, the literature was surveyed and relevant sequences in GenBank and Lifeseq® databases were identified. Genes were selected on the following basis. Genes were identified from the literature that are involved in blood cell biology. Then GenBank database and Lifeseq® databases (Incyte) were screened to identify other genes containing homologous sequences using BLAST. Additionally, the Lifeseq® database (Incyte) was searched using a group of key words including cyclin, cul, phosphatase, apoptosis, kinase, serine kinase, tyrosine kinase, cdk, phosphodiesterase, protease, protease inhibitor, metalloproteinase, cathepsin, phospholipase, E2F, integrin, receptor, cytochrome, p450, cox, lipocortin, retinoic acid, CD, cdc, fas, TNF, gadd, cytokine, chemokine, growth factor, interleukin, heat shock protein, HSP, stress, STAT, myb, jun, fos, dpl, myc, bak, bcl, p53, phox, inflammation, oxidase, and glutathione.

After selecting the transcripts (ESTs) of interest, partial sets of ESTs representing a single gene were identified. Partial sets of ESTs for the same gene but identified by different selection methods were clustered. Sets of partial sequences (and their quality scores) were used to assemble contiguous sequences using the Phrap program with default settings. The longest "high quality" set of partial sequences was chosen. "High quality" is defined as sequences starting and ending with at least 10 contiguous base calls with quality scores above 12. When performing the clustering process, the full Lifeseq® database (Incyte) was searched in order to obtain the longest "high quality" set of partial sequences.

After clustering related ESTs, EST clusters were checked for redundancy. The cDNAs were compared to each other using the BLASTn database search program. Any two sequences with similarity scores greater than 250 and percent identities greater than 95% were considered redundant. A representative cDNA sequence from each redundancy set was chosen and corresponds to the EST with the longest read sequence. In some cases, the representative cDNA sequence did not originate from the original cDNA libraries used in the selection processes.

Full length cDNAs (identified from Genbank or database and database (Incyte) Lifeseq®) and EST sets were also compared with each other to remove redundant sequences.

Illustrative polynucleotide probes for use in this invention are provided in the Sequence Listing and are SEQ ID Nos: 1–1508. The polynucleotide probes are derived from genes implicated in blood cell biology, including hematopoiesis, immunological responses and immuno-pathology. Of the 1,508 nonredundant polynucleotide probes 43% were exact matches to sequences in the public domain, 57% were homolgous to public domain sequences or unique sequences which are abundantly or differentially expressed in blood cell biology. Some of the public domain sequences were not known to be abundantly expressed or differentially expressed in hematopoiesis or immunological responses.

VI Preparation of a Microarray

A microarray was prepared as follows: 96 different PCR polynucleotide probes were laid down in quadruplicate (4 arrays 100 spots each) on a aldehyde derivatized slide available from Cel Associates (Houston, Tex.). The glass slide had dimensions of 18×24 mm. The distance between the spots on the array is 500 microns. Samples were printed on the glass slide from the left upper corner to the right lower corner in the following order: g177865 (Human tumor necrosis factor alpha); g177869 (Human alpha-2-macroglobulin); g178163 (Human ADP-ribosylation factor 1); g219475 (Human immediate-early-response); g179699 (Human C5a anaphylatoxin receptor); g179892 (Human CAMP phosphodiesterase); g184840 (Human Fc-gamma receptor I); g181181 (Human cathepsin G); g181485 (Human DNA-binding protein B); g182487 (Human Fc-epsilon-receptor gamma-chain); g182504 (Human ferritin H chain mRNA); g182632 (Human FKBP-12 protein); g182976 (Human glyceraldehyde-3-phosphate dehydrogenase); g183063 (Human glia-derived nexin); g183067 (Human mRNA sequence with homology to GDP binding protein); g31914 (Human mRNA for coupling protein G(s) alpha); g184420 (Human 90-kDa heat-shock protein); g186264 (Human gamma-interferon-inducible protein); g179579 (Human beta-thromboglobulin-like protein); g187172 (Human leukotriene A-4 hydrolase); g187220 (Human L-plastin gene); g187243 (Human lysozyme mRNA); g188255 (Human MHC class II HLA-DR-alpha); g189150 (Human nephropontin); g190813 (Human Wilm's tumor-related protein); g189267 (Human neutrophil oxidase factor; g219868 (Human HM89); g182482 (Human fibroblast collagenase inhibitor); g189546 (Human plasminogen activator inhibitor); g899458 (Human 14-3-3 protein); g184628 (Human interleukin 6); g250802 (cathepsin S); g264772 (thymosin beta-10); g28251 (beta-actin.); g291926 (Human cystatin B); g292416 (Human macrophage inflammatory protein); g29508 (Human BTG1); g181179 (Human cathepsin D); g179952 (Human cathepsin L); g186933 (Human leukocyte adhesion protein); g29793 (leukocyte antigen CD37); g184628 (Human interleukin 6);

g29850 (Human CDw40 nerve growth factor); g238776 (p55); g306467 (Human binding protein mRNA); g306486 (Human cap-binding protein); g306773 (Human GM-CSF receptor); g307165 (Human myeloid cell differentiation protein); g307374 (Human RHOA proto-oncogene multidrug-resistance); g31097 (Human mRNA for elongation factor 1 alpha); g32576 (Human mRNA for interleukin-1 receptor); g220063 (Human sphingolipid activator proteins); g186283 (Human interleukin 1-beta); g190419 (Human secretory granule proteoglycan peptide); g33917 (Human mRNA for gamma-interferon inducible protein); g339420 (Human T cell-specific protein (RANTES)); g339688 (Human thymosin beta-4 mRNA); g339690 (Human prothymosin alpha); g339737 (Human tumor necrosis factor (TNF)); g340020 (Human alpha-tubulin); g34312 (Human mRNA for lactate dehydrogenase-A); g187434 (Human monocyte chemotactic and activatinG factor); g179579 (Human beta-thromboglobulin-like protein); g34625 (Human gene for melanoma growth stimulator); g188558 (Human macrophage inflam-matory protein); g181191 (Human cathepsin B proteinase); g348911 (Human glycoprotein); g337494 (Human ribosomal protein L7a); g35517 (Human mRNA for pleckstrin (P47)); g1562497 (Human poly(A)-binding protein); g338285 (Human manganese-containing superoxide dismutase); g339737 (Human tumor necrosis factor (TNF)); g404012 (Human pre-B cell enhancing factor); g495286 (Human melanoma differentiation associated factor); g416368 (Human CTLA4 counter-receptor); g433415 (Human mRNA for DNA-binding protein, TAXR); g434760 (Human mRNA for ORF); g598867 (Human HepG2 partial cDNA); g450280 (Human sui1iso1); g517197 (Human urokinase-type plasminogen activator); g187151 (Human lysosomal acid lipase); g468150 (Human MAP kinase); g496975 (Human cyclooxygenase-2); g186512 (Human (clone 1950.2) interferon-gamma); g560790 (Human mRNA for calgizzarin); g1255239 (Human lysosomal-associated multitransmembrane protein); g245388 (beta 2-microglobulin); g178019 (Human cytokine (SCYA2) gene); g1304482 (Human tissue inhibitor of metalloprotein); g886049 (Human Ich-2 cysteine protease); g189177 (Human nuclear factor kappa-B DNA binding protein); g37983 (Human mRNA of X-CGD gene); g178083 (Human adenylyl cyclase-associated protein); g29899 Human mRNA for c-fms proto-oncogene); and g36606 (Human spermidine/spermine N1-acetyltransferase). The 9th and the 18th rows contained controls derived from *Drosophila melonogaster* and *Arabidopsis thaliana*.

An experiment was performed to measure gene expression in A. THP1 cells and B. THP1 cells first treated with 100 ng/ml PMA (phorbol ester myristate) for 48 hours and then treated with 1 microgram/ml LPS (liposacharride) for 48 hours. THP1 cells were obtained for the American Type Culture Collection. Treated and untreated cells were lysed, mRNA was purified using oligo d(T) chromatography. The mRNA was labeled by adding oligo(dT)20 (5 micrograms) to 2 micrograms mRNA and heating the reaction to 70° C. Hybridization was performed with 5×SSC/0.2% SDS for six (6) hours at 60° C. The slides were washed for five (5) minutes in 1×SSC/0.2%SDS at 30° C. followed by five (5) minutes in 0.1×SSC/0.2 SDS at room temperature followed by 30 minutes in 0.1×SCC at room temperature. Signals were detected using a custom made confocal fluorescence microscope.

Figure 2:
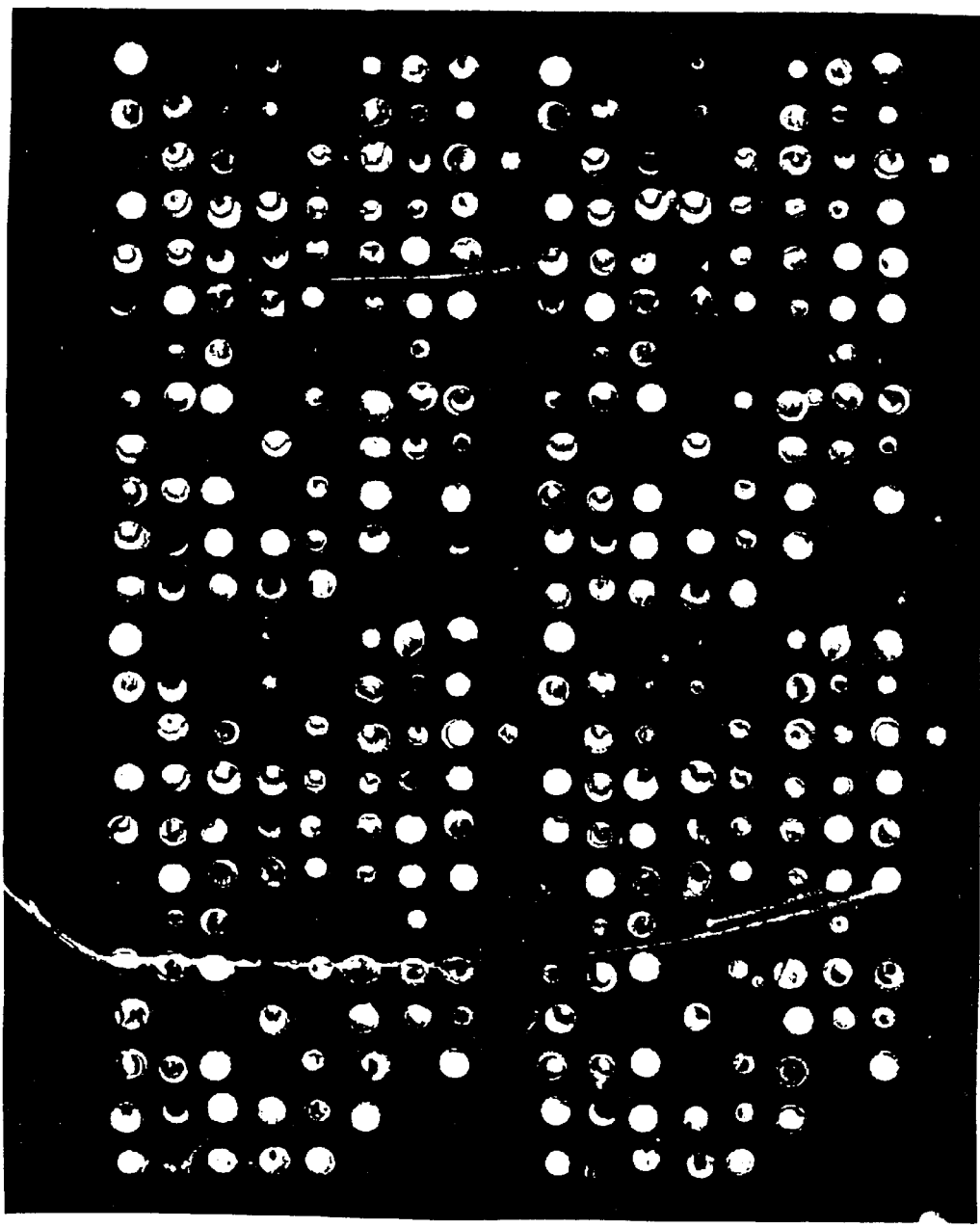
FIG. 2 is an image derived from an experiment where gene expression of treated THP cells is investigated using a microarray comprising cDNA polynucleotides.

Gene expression analysis was performed to identify gene sequences which were expressed at higher levels in treated THP1 cells rather than untreated THP1 cells. FIG. 1 shows the gene expression pattern observed in untreated THP1 cells. FIG. 2 shows the gene expression pattern observed in treated THP1 cells. By a comparision of both expression patterns, those genes differentially expressed in treated THP1 cells can be identified. For example, genes that are highly expressed in treated THP1 cells include the macrophage inflammatory protein gene, the cytokine (SCYA2) gene, and beta-thromboglobulin gene among others.

TABLE 1

| | CLONE ID | MATCH GI | ANNOTATION |
|---|---|---|---|
| SEQ ID NO: 1 | 000137 | INCYTE | INCYTE |
| SEQ ID NO: 2 | 000197 | INCYTE | INCYTE |
| SEQ ID NO: 3 | 000204 | INCYTE | INCYTE |
| SEQ ID NO: 4 | 000236 | INCYTE | INCYTE |
| SEQ ID NO: 5 | 000367 | INCYTE | INCYTE |
| SEQ ID NO: 6 | 000496 | INCYTE | INCYTE |
| SEQ ID NO: 7 | 000513 | g550069 | *Homo sapiens* GTP-binding protein (RAB5) mRNA, complete cds. |
| SEQ ID NO: 8 | 000596 | g2224680 | Human mRNA for KIAA0370 gene, partial cds. |
| SEQ ID NO: 9 | 000667 | INCYTE | INCYTE |
| SEQ ID NO: 10 | 000706 | INCYTE | INCYTE |
| SEQ ID NO: 10 | 000706 | INCYTE | INCYTE |
| SEQ ID NO: 11 | 000844 | INCYTE | INCYTE |
| SEQ ID NO: 12 | 001107 | g2190277 | Human mRNA for karyopherin alhph 3, complete cds. |
| SEQ ID NO: 13 | 001168 | INCYTE | INCYTE |
| SEQ ID NO: 14 | 001273 | INCYTE | INCYTE |
| SEQ ID NO: 15 | 001454 | INCYTE | INCYTE |
| SEQ ID NO: 16 | 001697 | INCYTE | INCYTE |
| SEQ ID NO: 17 | 002030 | INCYTE | INCYTE |
| SEQ ID NO: 18 | 002158 | INCYTE | INCYTE |
| SEQ ID NO: 19 | 002481 | g1911773 | putative Rab5-interacting protein {clone L1-57} [human, HeLa cells |
| SEQ ID NO: 20 | 002501 | INCYTE | INCYTE |
| SEQ ID NO: 21 | 002523 | INCYTE | INCYTE |
| SEQ ID NO: 22 | 002664 | g1945444 | Human autoantigen DFS70 mRNA, partial cds. |
| SEQ ID NO: 23 | 002682 | g2232056 | *Homo sapiens* Sm-like protein CaSm (CaSm) mRNA, complete cds. |
| SEQ ID NO: 24 | 002783 | INCYTE | INCYTE |
| SEQ ID NO: 25 | 002832 | INCYTE | INCYTE |
| SEQ ID NO: 26 | 003095 | INCYTE | INCYTE |
| SEQ ID NO: 27 | 003104 | g1799569 | Rat mRNA for TIP120, complete cds |
| SEQ ID NO: 28 | 003107 | INCYTE | INCYTE |
| SEQ ID NO: 29 | 003109 | INCYTE | INCYTE |
| SEQ ID NO: 30 | 003119 | g1694681 | Human mRNA for Src-like adapter protein, complete cds |
| SEQ ID NO: 31 | 003122 | INCYTE | INCYTE |
| SEQ ID NO: 32 | 003203 | INCYTE | INCYTE |
| SEQ ID NO: 33 | 003228 | INCYTE | INCYTE |
| SEQ ID NO: 34 | 003256 | INCYTE | INCYTE |
| SEQ ID NO: 35 | 003269 | INCYTE | INCYTE |
| SEQ ID NO: 36 | 003311 | INCYTE | INCYTE |
| SEQ ID NO: 37 | 003437 | g2183320 | *Mus musculus* unknown mRNA, complete cds |
| SEQ ID NO: 38 | 003440 | INCYTE | INCYTE |

TABLE 1-continued

| SEQ ID NO | ID | Accession | Description |
|---|---|---|---|
| SEQ ID NO: 39 | 003442 | INCYTE | INCYTE |
| SEQ ID NO: 40 | 003759 | INCYTE | INCYTE |
| SEQ ID NO: 41 | 003770 | INCYTE | INCYTE |
| SEQ ID NO: 42 | 003842 | INCYTE | INCYTE |
| SEQ ID NO: 43 | 003847 | INCYTE | INCYTE |
| SEQ ID NO: 44 | 003876 | INCYTE | INCYTE |
| SEQ ID NO: 45 | 003911 | INCYTE | INCYTE |
| SEQ ID NO: 46 | 004225 | INCYTE | INCYTE |
| SEQ ID NO: 47 | 004563 | INCYTE | INCYTE |
| SEQ ID NO: 48 | 004700 | INCYTE | INCYTE |
| SEQ ID NO: 49 | 004773 | INCYTE | INCYTE |
| SEQ ID NO: 50 | 007648 | INCYTE | INCYTE |
| SEQ ID NO: 51 | 008007 | g1813645 | Human MEK kinase 3 mRNA, complete cds. |
| SEQ ID NO: 52 | 008134 | g2224556 | Human mRNA for KIAA0308 gene, partial cds. |
| SEQ ID NO: 53 | 008653 | INCYTE | INCYTE |
| SEQ ID NO: 54 | 008724 | INCYTE | INCYTE |
| SEQ ID NO: 55 | 009118 | g1136742 | Human mRNA for protein disulfide isomerase-related protein P5, complete cds |
| SEQ ID NO: 56 | 009197 | g1870687 | Human Bruton's tyrosine kinase-associated protein-135 mRNA, complete cds. |
| SEQ ID NO: 57 | 009268 | INCYTE | INCYTE |
| SEQ ID NO: 58 | 009424 | INCYTE | INCYTE |
| SEQ ID NO: 59 | 010084 | INCYTE | INCYTE |
| SEQ ID NO: 60 | 010297 | INCYTE | INCYTE |
| SEQ ID NO: 61 | 010383 | INCYTE | INCYTE |
| SEQ ID NO: 62 | 010466 | INCYTE | INCYTE |
| SEQ ID NO: 63 | 010470 | INCYTE | INCYTE |
| SEQ ID NO: 64 | 010479 | g1753108 | Human cyclin A1 mRNA, complete cds. |
| SEQ ID NO: 65 | 010484 | g927532 | S.cerevisiae chromosome XIII left telomere and lambda 4987.CYTOCHROME C OXIDASE ASSEMBLY PROTEIN COX14. |
| SEQ ID NO: 66 | 010488 | INCYTE | INCYTE |
| SEQ ID NO: 67 | 010507 | INCYTE | INCYTE |
| SEQ ID NO: 68 | 010598 | g1913891 | Human clone 23652 mRNA sequence. |
| SEQ ID NO: 69 | 010699 | g1813543 | Human A28-RGS14p mRNA, complete cds. |
| SEQ ID NO: 70 | 010776 | INCYTE | INCYTE |
| SEQ ID NO: 71 | 010890 | INCYTE | INCYTE |
| SEQ ID NO: 72 | 010985 | INCYTE | INCYTE |
| SEQ ID NO: 73 | 011136 | INCYTE | INCYTE |
| SEQ ID NO: 74 | 011191 | g1167505 | Mouse mRNA for TAK1 (TGF-beta-activated kinase), complete cds. |
| SEQ ID NO: 75 | 011353 | INCYTE | Human BAC clone RG104I04 from 7q21-7q22, complete sequence. |
| SEQ ID NO: 76 | 011633 | INCYTE | INCYTE |
| SEQ ID NO: 77 | 011686 | g1666699 | Mouse Btk locus, alpha-D-galactosidase A |
| SEQ ID NO: 78 | 012092 | INCYTE | INCYTE |
| SEQ ID NO: 79 | 012364 | INCYTE | INCYTE |
| SEQ ID NO: 80 | 013321 | g247168 | protein phosphatase 2C alpha [human, teratocarcinoma, mRNA, 2346 nt]. |
| SEQ ID NO: 81 | 013985 | g1127832 | Human heat shock protein hsp40 homolog mRNA, complete cds. |
| SEQ ID NO: 82 | 014021 | INCYTE | INCYTE |
| SEQ ID NO: 83 | 014046 | g1928965 | Mouse SrcSH3 binding protein mRNA |
| SEQ ID NO: 84 | 014308 | g1596162 | Human mRNA for Iba1 (ionized calcium binding adapter molecule 1), |
| SEQ ID NO: 85 | 014571 | INCYTE | INCYTE |
| SEQ ID NO: 86 | 014617 | g1256605 | Mouse p53 responsive (EI24) mRNA, comple |
| SEQ ID NO: 87 | 015027 | INCYTE | INCYTE |
| SEQ ID NO: 88 | 015221 | g951289 | H.sapiens DNA for Rod cG-PDE gene (exons 4 to 10) and joined CDS. |
| SEQ ID NO: 89 | 015280 | INCYTE | INCYTE |
| SEQ ID NO: 90 | 015290 | INCYTE | INCYTE |
| SEQ ID NO: 91 | 015295 | INCYTE | INCYTE |
| SEQ ID NO: 92 | 015350 | INCYTE | INCYTE |
| SEQ ID NO: 93 | 015353 | INCYTE | INCYTE |
| SEQ ID NO: 94 | 015407 | INCYTE | INCYTE |
| SEQ ID NO: 95 | 015742 | INCYTE | INCYTE |
| SEQ ID NO: 96 | 015919 | INCYTE | INCYTE |
| SEQ ID NO: 97 | 015936 | INCYTE | INCYTE |
| SEQ ID NO: 98 | 015937 | g1778032 | Human GT334 protein (GT334) gene mRNA, complete cds. |
| SEQ ID NO: 99 | 016270 | g642119 | Mouse XRCC1 DNA repair gene, genomic. |
| SEQ ID NO: 99 | 016270 | g2415381 | Homo sapiens TFII-I protein (TFII-I) mRNA, complete cds. |
| SEQ ID NO: 100 | 016413 | INCYTE | INCYTE |

TABLE 1-continued

| SEQ ID NO | Number | ID | Description |
|---|---|---|---|
| SEQ ID NO: 101 | 018314 | INCYTE | INCYTE |
| SEQ ID NO: 102 | 018977 | INCYTE | INCYTE |
| SEQ ID NO: 103 | 018989 | INCYTE | INCYTE |
| SEQ ID NO: 104 | 019095 | INCYTE | INCYTE |
| SEQ ID NO: 105 | 019674 | INCYTE | INCYTE |
| SEQ ID NO: 106 | 019794 | g1778156 | *Mus musculus* nucleophosmin/nucleoplasmin-related protein (Npm3-ps1) pseudogene, complete cds. |
| SEQ ID NO: 107 | 020293 | INCYTE | INCYTE |
| SEQ ID NO: 108 | 020370 | INCYTE | INCYTE |
| SEQ ID NO: 109 | 020386 | INCYTE | INCYTE |
| SEQ ID NO: 110 | 020478 | INCYTE | INCYTE |
| SEQ ID NO: 111 | 020575 | INCYTE | INCYTE |
| SEQ ID NO: 112 | 020586 | g2280487 | Human mRNA for KIAA0392 gene, partial cds. |
| SEQ ID NO: 113 | 020596 | g2232173 | *Homo sapiens* putative fatty acid desaturase MLD mRNA, complete cds. |
| SEQ ID NO: 114 | 020696 | INCYTE | INCYTE |
| SEQ ID NO: 115 | 020833 | INCYTE | Human PAC clone DJ073F11 from Xq23, complete sequence. |
| SEQ ID NO: 116 | 021517 | INCYTE | INCYTE |
| SEQ ID NO: 117 | 021671 | INCYTE | INCYTE |
| SEQ ID NO: 118 | 022747 | g1843410 | Human mRNA for RP105, complete cds. |
| SEQ ID NO: 119 | 023284 | INCYTE | INCYTE |
| SEQ ID NO: 120 | 023381 | INCYTE | INCYTE |
| SEQ ID NO: 121 | 024130 | INCYTE | INCYTE |
| SEQ ID NO: 122 | 024704 | INCYTE | INCYTE |
| SEQ ID NO: 123 | 024741 | INCYTE | INCYTE |
| SEQ ID NO: 124 | 026498 | g180461 | Human cGMP-gated cation channel protein mRNA, complete cds. |
| SEQ ID NO: 125 | 026618 | INCYTE | INCYTE |
| SEQ ID NO: 126 | 026722 | g1911775 | putative Rab5-interacting protein {clone L1-94} [human, HeLa cells |
| SEQ ID NO: 127 | 026905 | INCYTE | INCYTE |
| SEQ ID NO: 128 | 027073 | g190126 | Human mitochondrial matrix protein P1 (nuclear encoded) mRNA, complete |
| SEQ ID NO: 129 | 027267 | INCYTE | INCYTE |
| SEQ ID NO: 130 | 027514 | INCYTE | INCYTE |
| SEQ ID NO: 131 | 027756 | INCYTE | INCYTE |
| SEQ ID NO: 132 | 027824 | INCYTE | INCYTE |
| SEQ ID NO: 133 | 027971 | INCYTE | INCYTE |
| SEQ ID NO: 134 | 028148 | INCYTE | INCYTE |
| SEQ ID NO: 135 | 028787 | g1729776 | *M.musculus* mRNA for TEL protein. |
| SEQ ID NO: 136 | 028971 | g1255917 | CDC4 |
| SEQ ID NO: 137 | 029270 | INCYTE | INCYTE |
| SEQ ID NO: 138 | 029592 | g1791002 | Human macrophage inflammatory protein 3 beta (MIP-3beta) mRNA, complete cds. |
| SEQ ID NO: 139 | 030041 | g1702923 | *H.sapiens* mRNA for p0071 protein. |
| SEQ ID NO: 140 | 030137 | g1710240 | Human clone 23733 mRNA, complete cds. |
| SEQ ID NO: 141 | 030424 | g2370152 | *Homo sapiens* mRNA for putatively prenylated protein. |
| SEQ ID NO: 142 | 030659 | g1710265 | Human clone 23867 mRNA sequence. |
| SEQ ID NO: 143 | 030772 | INCYTE | INCYTE |
| SEQ ID NO: 144 | 030796 | g167801 | Dictyostelium discoideum glycoprotein phosphorylase 2 (glpD) gene |
| SEQ ID NO: 145 | 030880 | INCYTE | INCYTE |
| SEQ ID NO: 146 | 030897 | INCYTE | INCYTE |
| SEQ ID NO: 147 | 031122 | INCYTE | INCYTE |
| SEQ ID NO: 148 | 031139 | g2230877 | *H.sapiens* mRNA for nucleolar protein hNop56. |
| SEQ ID NO: 149 | 031413 | INCYTE | INCYTE |
| SEQ ID NO: 150 | 031416 | g35211 | *H.sapiens* mRNA for p53-associated gene. |
| SEQ ID NO: 151 | 031470 | INCYTE | INCYTE |
| SEQ ID NO: 152 | 031859 | INCYTE | INCYTE |
| SEQ ID NO: 153 | 031968 | g1665762 | Human mRNA for KIAA0247 gene, complete cds. |
| SEQ ID NO: 154 | 031982 | INCYTE | INCYTE |
| SEQ ID NO: 155 | 032302 | INCYTE | INCYTE |
| SEQ ID NO: 156 | 033600 | g1136395 | Human mRNA for KIAA0168 gene, complete cds. |
| SEQ ID NO: 157 | 034109 | g1890631 | Human SNC19 mRNA sequence. |
| SEQ ID NO: 158 | 034755 | g1698691 | Human growth factor independence-1 (Gfi-1) mRNA, complete cds. |
| SEQ ID NO: 159 | 034925 | INCYTE | INCYTE |
| SEQ ID NO: 160 | 034995 | INCYTE | INCYTE |

TABLE 1-continued

| SEQ ID NO: 161 | 035437 | g758415 | Human transcription factor E2F-5 mRNA, complete cds. |
|---|---|---|---|
| SEQ ID NO: 162 | 036448 | INCYTE | INCYTE |
| SEQ ID NO: 163 | 037497 | g2232240 | *Homo sapiens* secretory carrier membrane protein (SCAMP2) mRNA, |
| SEQ ID NO: 164 | 040266 | INCYTE | INCYTE |
| SEQ ID NO: 165 | 040330 | g1854034 | Human Cdc5-related protein (PCDC5RP) mRNA, complete cds |
| SEQ ID NO: 166 | 040395 | g2224604 | Human mRNA for KIAA0332 gene, partial cds. |
| SEQ ID NO: 167 | 040476 | INCYTE | INCYTE |
| SEQ ID NO: 168 | 040550 | INCYTE | INCYTE |
| SEQ ID NO: 169 | 040601 | g1695739 | M130 of smooth muscle myosin phosphatase |
| SEQ ID NO: 170 | 040808 | INCYTE | INCYTE |
| SEQ ID NO: 171 | 040940 | INCYTE | INCYTE |
| SEQ ID NO: 172 | 040996 | INCYTE | INCYTE |
| SEQ ID NO: 173 | 041116 | g7758 | crooked neck (crn) |
| SEQ ID NO: 174 | 041860 | g1916640 | Human FK506-binding protein FKBP51 mRNA, complete cds. |
| SEQ ID NO: 175 | 042027 | g1491937 | CAF; p300 CBP-associated factor |
| SEQ ID NO: 176 | 043386 | INCYTE | INCYTE |
| SEQ ID NO: 177 | 045328 | INCYTE | INCYTE |
| SEQ ID NO: 178 | 045451 | INCYTE | INCYTE |
| SEQ ID NO: 179 | 045454 | INCYTE | INCYTE |
| SEQ ID NO: 180 | 052437 | g961445 | Human mRNA for KIAA0241 gene, partial cds. |
| SEQ ID NO: 181 | 053209 | INCYTE | INCYTE |
| SEQ ID NO: 182 | 053532 | INCYTE | INCYTE |
| SEQ ID NO: 183 | 053537 | INCYTE | INCYTE |
| SEQ ID NO: 184 | 057310 | INCYTE | INCYTE |
| SEQ ID NO: 185 | 059081 | INCYTE | INCYTE |
| SEQ ID NO: 186 | 059846 | g1167537 | Human caveolin-2 mRNA, complete cds. |
| SEQ ID NO: 187 | 060269 | INCYTE | INCYTE |
| SEQ ID NO: 188 | 060309 | g1663703 | Human mRNA for KIAA0242 gene, partial cds. |
| SEQ ID NO: 189 | 060779 | INCYTE | INCYTE |
| SEQ ID NO: 190 | 060951 | INCYTE | INCYTE |
| SEQ ID NO: 191 | 064994 | INCYTE | INCYTE |
| SEQ ID NO: 192 | 071177 | INCYTE | INCYTE |
| SEQ ID NO: 193 | 073159 | INCYTE | INCYTE |
| SEQ ID NO: 194 | 073293 | INCYTE | INCYTE |
| SEQ ID NO: 195 | 073345 | INCYTE | INCYTE |
| SEQ ID NO: 196 | 073347 | INCYTE | INCYTE |
| SEQ ID NO: 197 | 073582 | g557875 | *Mus musculus* SKD1 protein mRNA, complete cds. |
| SEQ ID NO: 198 | 073735 | g529642 | Human mRNA for leukotriene B4 omega-hydroxylase, complete cds. |
| SEQ ID NO: 199 | 074398 | INCYTE | INCYTE |
| SEQ ID NO: 200 | 074431 | INCYTE | INCYTE |
| SEQ ID NO: 201 | 074449 | g1791256 | Human copine I mRNA, complete cds. |
| SEQ ID NO: 203 | 075091 | g38050 | *M.fascicularis* gene for apolipoprotein A-IV. |
| SEQ ID NO: 204 | 075169 | INCYTE | INCYTE |
| SEQ ID NO: 205 | 078090 | INCYTE | INCYTE |
| SEQ ID NO: 206 | 078610 | INCYTE | INCYTE |
| SEQ ID NO: 207 | 078771 | INCYTE | INCYTE |
| SEQ ID NO: 208 | 078822 | INCYTE | INCYTE |
| SEQ ID NO: 209 | 079378 | INCYTE | INCYTE |
| SEQ ID NO: 210 | 079479 | INCYTE | INCYTE |
| SEQ ID NO: 211 | 079895 | INCYTE | INCYTE |
| SEQ ID NO: 212 | 080226 | INCYTE | INCYTE |
| SEQ ID NO: 213 | 080231 | INCYTE | INCYTE |
| SEQ ID NO: 214 | 080369 | INCYTE | INCYTE |
| SEQ ID NO: 215 | 080752 | g1913891 | Human clone 23652 mRNA sequence. |
| SEQ ID NO: 216 | 081040 | INCYTE | INCYTE |
| SEQ ID NO: 217 | 081583 | INCYTE | INCYTE |
| SEQ ID NO: 218 | 084009 | g339877 | *Homo sapiens* tripeptidyl peptidase II mRNA, 3' end. |
| SEQ ID NO: 219 | 084374 | INCYTE | INCYTE |
| SEQ ID NO: 220 | 086674 | INCYTE | INCYTE |
| SEQ ID NO: 221 | 087031 | INCYTE | INCYTE |
| SEQ ID NO: 222 | 087235 | g1654324 | Human chromosome 5 Mad homolog Smad5 mRNA, complete cds. |
| SEQ ID NO: 223 | 089993 | g184349 | Human hypoxanthine phosphoribosyltransferase (HPRT) mRNA |
| SEQ ID NO: 224 | 098835 | g2330739 | SPAC1B3.05 hypothetical protein |
| SEQ ID NO: 225 | 1000787 | INCYTE | INCYTE |
| SEQ ID NO: 226 | 1004415 | g1707479 | *H.sapiens* mRNA for CRM1 protein. |

TABLE 1-continued

| SEQ ID | Number | Accession | Description |
|---|---|---|---|
| SEQ ID NO: 227 | 101411 | INCYTE | INCYTE |
| SEQ ID NO: 228 | 103585 | INCYTE | INCYTE |
| SEQ ID NO: 229 | 103656 | INCYTE | INCYTE |
| SEQ ID NO: 230 | 103704 | INCYTE | INCYTE |
| SEQ ID NO: 231 | 103933 | g2358042 | *Homo sapiens* T-cell receptor alpha delta locus from bases 501613 to 103933 |
| SEQ ID NO: 232 | 104098 | INCYTE | INCYTE |
| SEQ ID NO: 233 | 104159 | INCYTE | INCYTE |
| SEQ ID NO: 234 | 104211 | INCYTE | INCYTE |
| SEQ ID NO: 235 | 104368 | g1022903 | Human phosducin-like protein (PhLP) gene, partial cds. intron 2(partial)/exon 3/intron 3 (partial). |
| SEQ ID NO: 236 | 104451 | g2351798 | Human clone HM18 monocyte inhibitory receptor precursor mRNA, |
| SEQ ID NO: 237 | 104731 | INCYTE | INCYTE |
| SEQ ID NO: 238 | 104903 | INCYTE | INCYTE |
| SEQ ID NO: 239 | 104965 | INCYTE | INCYTE |
| SEQ ID NO: 240 | 105088 | g2088550 | Human hereditary haemochromatosis region, histone 2A-like protein |
| SEQ ID NO: 241 | 105363 | INCYTE | INCYTE |
| SEQ ID NO: 242 | 108082 | g1399461 | Human serine/threonine-protein kinase PRP4h (PRP4h) mRNA, complete |
| SEQ ID NO: 243 | 108465 | g38014 | Human mRNA for zinc finger protein (clone 431) |
| SEQ ID NO: 244 | 108608 | g2078532 | Human DNA binding protein FKHL15 (FKHL15) mRNA, complete cds. |
| SEQ ID NO: 245 | 108762 | INCYTE | INCYTE |
| SEQ ID NO: 246 | 108819 | INCYTE | INCYTE |
| SEQ ID NO: 247 | 109390 | INCYTE | INCYTE |
| SEQ ID NO: 248 | 109451 | INCYTE | INCYTE |
| SEQ ID NO: 249 | 109706 | INCYTE | INCYTE |
| SEQ ID NO: 250 | 109719 | INCYTE | INCYTE |
| SEQ ID NO: 251 | 114110 | INCYTE | INCYTE |
| SEQ ID NO: 252 | 114495 | g169880 | nodulin |
| SEQ ID NO: 253 | 1216210 | g391765 | Mouse mRNA for peptidylarginine deiminase, complete cds. |
| SEQ ID NO: 254 | 1217861 | g2443362 | *Homo sapiens* mRNA for STAT induced STAT inhibitor-3, complete cds. |
| SEQ ID NO: 255 | 1218519 | g1864004 | Human mRNA for transmembrane protein, complete cds. |
| SEQ ID NO: 256 | 122762 | g2194202 | *Homo sapiens* pescadillo mRNA, complete cds. |
| SEQ ID NO: 257 | 1234356 | g407307 | Human 54 kDa protein mRNA, complete cds. |
| SEQ ID NO: 258 | 1241495 | g1944415 | Human mRNA for KIAA0235 gene, partial cds. |
| SEQ ID NO: 259 | 1242547 | g1000861 | *Homo sapiens* creatine kinase B mRNA, complete cds. |
| SEQ ID NO: 260 | 1243040 | g1731808 | Human mRNA for c-myc binding protein, complete cds. |
| SEQ ID NO: 261 | 1256257 | g793182 | *Homo sapiens* cDNA clone 38356 5' similar to SP:S34291 S34291 CYTOCHROME P-450 - FRUIT FLY |
| SEQ ID NO: 262 | 1257695 | g1817732 | Human KIT protein and alternatively spliced KIT protein (KIT) gene, |
| SEQ ID NO: 263 | 1257906 | g2286223 | IKK-a; IKK-a kinase |
| SEQ ID NO: 264 | 1260257 | g1139592 | *Mus musculus* leptin receptor (Ob-r) mRNA, complete CDs. |
| SEQ ID NO: 265 | 1261161 | * INCYTE | INCYTE |
| SEQ ID NO: 266 | 1265680 | g286230 | Rat NAP-22 mRNA for acidic membrane protein of rat brain, complete |
| SEQ ID NO: 267 | 126758 | INCYTE | INCYTE |
| SEQ ID NO: 268 | 1268703 | g407955 | Human membrane-associated protein (HEM-1) mRNA, complete cds. |
| SEQ ID NO: 269 | 1271822 | g189389 | *Homo sapiens* osteogenic protein-2 (OP-2) mRNA, complete CDs. |
| SEQ ID NO: 270 | 1274145 | g263309 | Vgr-2 = transforming growth factor-beta homolog |
| SEQ ID NO: 271 | 1286844 | g1226242 | EF-hand Ca2 + binding protein p22 |
| SEQ ID NO: 272 | 1291208 | g642116 | Human XRCC1 DNA repair gene, genomic. |
| SEQ ID NO: 273 | 1292521 | g1490514 | Rat maspin mRNA, complete cds. |
| SEQ ID NO: 274 | 1298861 | g1229044 | C11H1 *C.elegans* |
| SEQ ID NO: 275 | 1299537 | g1008046 | Cytochrome P450 |
| SEQ ID NO: 276 | 1302907 | g401771 | *Homo sapiens* ribosomal protein S6 kinase 2 (RPS6KA2) mRNA, partial cds. |
| SEQ ID NO: 277 | 1303190 | INCYTE | INCYTE |
| SEQ ID NO: 278 | 1305494 | g1654001 | *H.sapiens* mRNA for Sop2p-like protein |
| SEQ ID NO: 279 | 1307464 | g473361 | vitellogenic carboxypeptidase |
| SEQ ID NO: 280 | 1307568 | g1572817 | K08F11 *C.elegans* |
| SEQ ID NO: 281 | 1310265 | g452059 | Human insulin-like growth factor binding protein 5 (IGFBP5) mRNA. |
| SEQ ID NO: 282 | 1317697 | g1216525 | Human p38-2G4 mRNA, partial cds. |

TABLE 1-continued

| SEQ ID NO | ID | Accession | Description |
|---|---|---|---|
| SEQ ID NO: 283 | 131925 | INCYTE | INCYTE |
| SEQ ID NO: 284 | 132313 | INCYTE | INCYTE |
| SEQ ID NO: 285 | 132537 | g1638827 | Human DNA sequence from BAC 397C4 on chromosome 22q12-qter contains ESTs and STS. |
| SEQ ID NO: 286 | 1326793 | g220391 | Mouse gene for cytokeratin endo A. |
| SEQ ID NO: 287 | 133060 | BL01066B | Hypothetical YBR002c family proteins. |
| SEQ ID NO: 288 | 133089 | g2315986 | Human high-affinity copper uptake protein (hCTR1) mRNA, complete cds |
| SEQ ID NO: 289 | 133107 | INCYTE | INCYTE |
| SEQ ID NO: 290 | 1339742 | g1575664 | Rat calcium-activated potassium channel |
| SEQ ID NO: 291 | 1340453 | g473406 | *Mus musculus* Hsp70-related NST-1 (hsr.1) mRNA, complete cds |
| SEQ ID NO: 292 | 1341948 | g1209752 | Cybb; gp91phox |
| SEQ ID NO: 293 | 1344641 | g598955 | Human mRNA for hepatoma-derived growth factor, complete cds. |
| SEQ ID NO: 294 | 134481 | g1857330 | Human SPS1/STE20 homolog KHS1 mRNA, complete cds. |
| SEQ ID NO: 295 | 1346478 | g1667346 | T13F2 *C.elegans* |
| SEQ ID NO: 296 | 1347577 | g1389723 | Mouse transcription factor MMUSF (USF) gene, exons 1–10 complete cds |
| SEQ ID NO: 297 | 1347596 | g575457 | CDC40; Cdc40p |
| SEQ ID NO: 298 | 134898 | INCYTE | INCYTE |
| SEQ ID NO: 299 | 134902 | g484295 | Rat mRNA for Synaptotagmin III, complete cds |
| SEQ ID NO: 300 | 1350210 | g1127832 | Human heat shock protein hsp40 homolog mRNA, complete cds. |
| SEQ ID NO: 301 | 1353065 | g182736 | Human cerebellar degeneration-associated protein mRNA, complete cds |
| SEQ ID NO: 302 | 135360 | INCYTE | INCYTE |
| SEQ ID NO: 303 | 135394 | g1137697 | *Homo sapiens* cDNA clone 261714 5' similar to SP:BYR2_SCHPO P28829 PROTEIN KINASE BYR2 |
| SEQ ID NO: 304 | 135651 | g180617 | *Homo sapiens* collagenase mRNA, complete cds. |
| SEQ ID NO: 305 | 1362601 | g886049 | Human Ich-2 cysteine protease mRNA, complete cds. |
| SEQ ID NO: 306 | 1363543 | g183007 | Human glucocerebrosidase mRNA, complete cds. |
| SEQ ID NO: 307 | 136466 | g1518917 | Human DNAJ homolog (DNAJW) gene, complete cds. |
| SEQ ID NO: 308 | 1378524 | g2305263 | *Homo sapiens* chemokine receptor X (CKRX) mRNA, complete cds. |
| SEQ ID NO: 309 | 1382605 | g1794218 | Human 150 kDa oxygen-regulated protein ORP150 mRNA, complete cds. |
| SEQ ID NO: 310 | 139332 | INCYTE | INCYTE |
| SEQ ID NO: 311 | 139645 | INCYTE | INCYTE |
| SEQ ID NO: 312 | 140055 | g1914848 | *Mus musculus* WW domain binding protein 3 mRNA, partial cds. |
| SEQ ID NO: 313 | 140290 | INCYTE | INCYTE |
| SEQ ID NO: 314 | 140314 | INCYTE | INCYTE |
| SEQ ID NO: 315 | 140340 | INCYTE | INCYTE |
| SEQ ID NO: 316 | 1404269 | g1517896 | Human renal cell carcinoma antigen RAGE-1 mRNA, complete putative |
| SEQ ID NO: 317 | 1405467 | g220391 | Mouse ferritin heavy chain gene, complet |
| SEQ ID NO: 318 | 1406078 | g340038 | Human protein tyrosine kinase related mRNA sequence. |
| SEQ ID NO: 319 | 140628 | INCYTE | INCYTE |
| SEQ ID NO: 320 | 140652 | INCYTE | INCYTE |
| SEQ ID NO: 321 | 140693 | INCYTE | INCYTE |
| SEQ ID NO: 322 | 140704 | INCYTE | INCYTE |
| SEQ ID NO: 323 | 140809 | INCYTE | INCYTE |
| SEQ ID NO: 324 | 141286 | INCYTE | INCYTE |
| SEQ ID NO: 325 | 141304 | INCYTE | INCYTE |
| SEQ ID NO: 326 | 141389 | INCYTE | INCYTE |
| SEQ ID NO: 327 | 141399 | g2072422 | Human huntingtin interacting protein (HIP1) mRNA, complete cds. |
| SEQ ID NO: 328 | 1414094 | g640037 | A20 protein; murine A20 |
| SEQ ID NO: 329 | 141454 | g1019164 | Human beta adaptin gene, exons 1–4, and partial cds. |
| SEQ ID NO: 330 | 141618 | INCYTE | INCYTE |
| SEQ ID NO: 331 | 1418681 | g825544 | unknown. |
| SEQ ID NO: 332 | 1418802 | g396492 | *H.sapiens* mRNA for rod cGMP phosphodiesterase. |
| SEQ ID NO: 333 | 1418874 | g391694 | Hamster mRNA for cyclinB2, complete cds |
| SEQ ID NO: 334 | 1419118 | g2062674 | inhibitor of apoptosis protein 1 |

TABLE 1-continued

| SEQ ID NO: | | | |
|---|---|---|---|
| SEQ ID NO: 335 | 142456 | g1236166 | Human DNA sequence from cosmid J30E17, between markers DXS366 and DXS87 on chromosome X contains repeat polymorphism and ribosomal protein L7A. |
| SEQ ID NO: 336 | 1425434 | g1469187 | KIAA0132 |
| SEQ ID NO: 337 | 1427866 | g1665772 | Human mRNA for KIAA0253 gene, partial cds. |
| SEQ ID NO: 338 | 1429970 | g1718196 | Human translation initiation factor eIF-3 p110 subunit gene, complete cds. |
| SEQ ID NO: 339 | 143092 | g1848232 | Human DNA-binding protein CPBP (CPBP) mRNA, partial cds. |
| SEQ ID NO: 340 | 143157 | g2460199 | *Homo sapiens* eukaryotic translation initiation factor 3 subunit (p42) |
| SEQ ID NO: 341 | 1432736 | g1632761 | Human mRNA for TPRDI, complete cds. |
| SEQ ID NO: 342 | 143379 | g183369 | Human glia maturation factor beta mRNA, complete cds. |
| SEQ ID NO: 343 | 143403 | INCYTE | INCYTE |
| SEQ ID NO: 344 | 1439061 | g1666070 | *H.sapiens* mRNA for GAR22 protein. |
| SEQ ID NO: 345 | 1440128 | g401766 | *Homo sapiens* growth-arrest-specific protein (gas) mRNA, complete cds. |
| SEQ ID NO: 346 | 144388 | INCYTE | INCYTE |
| SEQ ID NO: 347 | 1444245 | g1857460 | Human immunoglobulin-like transcript-3 mRNA, complete cds. |
| SEQ ID NO: 348 | 144484 | INCYTE | INCYTE |
| SEQ ID NO: 349 | 144491 | INCYTE | INCYTE |
| SEQ ID NO: 350 | 1445507 | g2406579 | *Homo sapiens* nuclear VCP-like protein NVLp.1 (NVL.1) mRNA, complete |
| SEQ ID NO: 351 | 144735 | g563126 | Human acid finger protein mRNA, complete cds. |
| SEQ ID NO: 352 | 1447451 | g2437846 | Rattus sp. mRNA for DNA binding protein, KET |
| SEQ ID NO: 353 | 144991 | INCYTE | INCYTE |
| SEQ ID NO: 354 | 1450668 | g2317724 | *Mus musculus* putative lysophosphatidic acid acyltransferase mRNA |
| SEQ ID NO: 355 | 145287 | INCYTE | INCYTE |
| SEQ ID NO: 356 | 145330 | g31742 | Human gene for Gi3 alpha protein, intron 7 through exon 9, variant U6 gene, and snRNP E protein pseudogene LH87. |
| SEQ ID NO: 357 | 1453807 | g1517913 | Human monocytic leukaemia zinc finger protein (MOZ) mRNA, complete cds. |
| SEQ ID NO: 358 | 1456841 | g309217 | epidermal growth factor receptor kinase substrate |
| SEQ ID NO: 359 | 145856 | g1665814 | Human mRNA for KIAA0275 gene, complete cds. |
| SEQ ID NO: 360 | 1459391 | g190510 | Human PRB2 locus salivary proline-rich protein mRNA, clone cP7. |
| SEQ ID NO: 361 | 146190 | INCYTE | INCYTE |
| SEQ ID NO: 362 | 146204 | INCYTE | INCYTE |
| SEQ ID NO: 363 | 146256 | INCYTE | INCYTE |
| SEQ ID NO: 364 | 1467987 | g1572756 | C43G2 *C.elegans* |
| SEQ ID NO: 365 | 146892 | INCYTE | INCYTE |
| SEQ ID NO: 366 | 146907 | g339242 | Human Tcr-C-delta gene, exons 1–4; Tcr-V-delta gene, exons 1–2; T-cell receptor alpha (Tcr-alpha) gene, J1–J61 segments; and Tcr-C-alpha gene, exons 1–4. |
| SEQ ID NO: 367 | 146947 | g899108 | Human histidyl-tRNA synthetase homolog (HO3) mRNA, complete cds. |
| SEQ ID NO: 368 | 1473337 | g1507666 | ORF N118 |
| SEQ ID NO: 369 | 1477849 | g2352903 | *Homo sapiens* DNJ3/CPR3 mRNA, complete cds. |
| SEQ ID NO: 370 | 1481932 | g1781008 | *H.sapiens* mRNA for P2X4 purinoceptor. |
| SEQ ID NO: 371 | 1482516 | g431253 | Human PAX3/forkhead transcription factor gene fusion mRNA, complete cds. |
| SEQ ID NO: 372 | 148286 | INCYTE | INCYTE |
| SEQ ID NO: 373 | 1488169 | g1916849 | Human scaffold protein Pbp1 mRNA, complete cds. |
| SEQ ID NO: 374 | 1488278 | g1151230 | LPG12w; Lpg12p |
| SEQ ID NO: 375 | 1489285 | g603951 | Human mRNA for KIAA0097 gene, complete cds. |
| SEQ ID NO: 376 | 1491277 | g312044 | *H.sapiens* mRNA for bone-marrow proteoglycan (BMPG). |
| SEQ ID NO: 377 | 1495437 | g1575504 | Mouse Tera (Tera) mRNA, complete cds |
| SEQ ID NO: 378 | 1501023 | g2415296 | *Homo sapiens* p53 induced protein mRNA, partial cds. |
| SEQ ID NO: 379 | 150135 | g2462850 | *Rattus norvegicus* Spinophilin mRNA, complete cds. |
| SEQ ID NO: 380 | 1503740 | g1666070 | *H.sapiens* mRNA for GAR22 protein. |

TABLE 1-continued

| | | | |
|---|---|---|---|
| SEQ ID NO: 381 | 1506007 | g587531 | orf, len: 423, CAI: 0.18, 27.4% identity in 307 aa overlap with S36201 S36201 hypothetical protein 1 - *Rhizobium leguminosarum* |
| SEQ ID NO: 382 | 1508778 | g307310 | *Homo sapiens* neuroendocrine-specific protein C (NSP) mRNA, complete cds. |
| SEQ ID NO: 383 | 150993 | INCYTE | INCYTE |
| SEQ ID NO: 384 | 1511256 | g1041308 | E04D5 |
| SEQ ID NO: 385 | 1516618 | g1568642 | Human RNA binding protein Etr-3 mRNA, complete cds. |
| SEQ ID NO: 386 | 151873 | g1058795 | *Homo sapiens* cDNA clone 241480 5' similar to contains Alu repetitive element;. |
| SEQ ID NO: 387 | 1520835 | g1161128 | TNFR2-TRAF signalling complex protein |
| SEQ ID NO: 388 | 1522948 | g34675 | Human myosin alkali light chain mRNA. |
| SEQ ID NO: 389 | 1526164 | INCYTE | INCYTE |
| SEQ ID NO: 390 | 1526481 | INCYTE | INCYTE |
| SEQ ID NO: 391 | 152657 | g1778050 | Human Prt1 homolog mRNA, complete cds. |
| SEQ ID NO: 392 | 152887 | g2257694 | *Homo sapiens* mRNA for SCGF, complete cds. |
| SEQ ID NO: 393 | 1531886 | g28850 | *H.sapiens* mRNA for arrestin (partial) |
| SEQ ID NO: 394 | 1532102 | INCYTE | INCYTE |
| SEQ ID NO: 395 | 153338 | g186260 | Human placental ribonuclease inhibitor mRNA, complete cds. |
| SEQ ID NO: 396 | 153423 | INCYTE | INCYTE |
| SEQ ID NO: 397 | 1538925 | g7219 | *D.discoideum* CABP1 gene for CABP1 cAMP binding protein. |
| SEQ ID NO: 398 | 155094 | g2065560 | Human DNA fragmentation factor-45 mRNA, complete cds. |
| SEQ ID NO: 399 | 1555947 | g1791256 | Human copine I mRNA, complete cds. |
| SEQ ID NO: 400 | 156196 | g1549395 | MMPDE7A; cyclic nucleotide phosphodiesterase PDE7A2. |
| SEQ ID NO: 401 | 156352 | INCYTE | INCYTE |
| SEQ ID NO: 402 | 157234 | INCYTE | INCYTE |
| SEQ ID NO: 403 | 1573272 | INCYTE | INCYTE |
| SEQ ID NO: 404 | 1573553 | INCYTE | INCYTE |
| SEQ ID NO: 405 | 1574210 | INCYTE | INCYTE |
| SEQ ID NO: 406 | 1574415 | INCYTE | INCYTE |
| SEQ ID NO: 407 | 1574617 | g2055255 | Human mRNA for proteasome subunit p27, complete cds. |
| SEQ ID NO: 408 | 1574637 | INCYTE | INCYTE |
| SEQ ID NO: 409 | 1576661 | INCYTE | INCYTE |
| SEQ ID NO: 410 | 158325 | INCYTE | INCYTE |
| SEQ ID NO: 411 | 1594362 | g1695802 | Human PAS protein 3 mRNA, complete cds. |
| SEQ ID NO: 412 | 159452 | g971273 | Mouse mRNA for osteoglycin, complete cds |
| SEQ ID NO: 413 | 159508 | g2459832 | *Rattus norvegicus* Maxp1 mRNA, complete cds. |
| SEQ ID NO: 414 | 1596759 | g6640 | B0464 |
| SEQ ID NO: 415 | 1597325 | g1255335 | *C. elegans* sex-determining protein FEM-1 |
| SEQ ID NO: 416 | 1602090 | g1944184 | Human mRNA for hSLK, complete cds. |
| SEQ ID NO: 417 | 1602848 | g205532 | metallothionein 2 |
| SEQ ID NO: 418 | 1603031 | g1657771 | Human herpesvirus entry mediator mRNA, complete cds. |
| SEQ ID NO: 419 | 1603383 | g1815657 | Human novel unknown gene, partial 3'UTR, and VEGF-related factor |
| SEQ ID NO: 420 | 1606384 | g1217604 | Yeast DNA for pre-mRNA splicing factor, complete cds. |
| SEQ ID NO: 421 | 160970 | INCYTE | INCYTE |
| SEQ ID NO: 422 | 1610405 | g727224 | *H.sapiens* partial mRNA for pyrophosphatase. |
| SEQ ID NO: 423 | 1610609 | g1923255 | Human 26S proteasome-associated pad1 homolog (POH1) mRNA, complete cds. |
| SEQ ID NO: 424 | 1610701 | g2208838 | Rat mRNA for peptide/histidine transporter, complete cds. |
| SEQ ID NO: 425 | 161120 | g1408462 | actin-binding protein of ectoplasmic specialization |
| SEQ ID NO: 426 | 161755 | g1419560 | Human DNA sequence from PAC 107N3, between markers DXS6791 and |
| SEQ ID NO: 427 | 1619615 | g1773070 | Human mRNA downregulated in adenovirus 5-infected cells. |
| SEQ ID NO: 428 | 162249 | g1871530 | Human BDP1 mRNA for protein-tyrosine-pho |
| SEQ ID NO: 429 | 1645339 | g50865 | *M.musculus* mRNA of enhancer-trap-locus 1. |
| SEQ ID NO: 430 | 1658706 | g453568 | SUR4 |
| SEQ ID NO: 431 | 1667573 | INCYTE | INCYTE |

TABLE 1-continued

| SEQ ID NO: | | | |
|---|---|---|---|
| SEQ ID NO: 432 | 1668184 | INCYTE | INCYTE |
| SEQ ID NO: 433 | 1668715 | INCYTE | INCYTE |
| SEQ ID NO: 434 | 1669352 | g804729 | *Homo sapiens* (subclone 6_f3 from P1 H19) DNA sequence. |
| SEQ ID NO: 435 | 169278 | INCYTE | INCYTE |
| SEQ ID NO: 436 | 169300 | INCYTE | INCYTE |
| SEQ ID NO: 437 | 169570 | INCYTE | INCYTE |
| SEQ ID NO: 438 | 169928 | g2181682 | *H.sapiens* telomeric DNA sequence, clone 3QTEL026 |
| SEQ ID NO: 439 | 169959 | INCYTE | INCYTE |
| SEQ ID NO: 440 | 170890 | INCYTE | INCYTE |
| SEQ ID NO: 441 | 1713576 | g180020 | Human monocyte antigen CD14 (CD14) mRNA, complete cds. |
| SEQ ID NO: 442 | 1713794 | INCYTE | INCYTE |
| SEQ ID NO: 443 | 171449 | g2224588 | Human mRNA for KIAA0324 gene, partial cds. |
| SEQ ID NO: 444 | 1714912 | g790386 | M03C11 |
| SEQ ID NO: 445 | 1715913 | g1323049 | ORF YGR046w |
| SEQ ID NO: 446 | 171603 | g198326 | Mouse interleukin 2 receptor (p55 IL-2R) mRNA, 5' end. |
| SEQ ID NO: 447 | 1716372 | INCYTE | INCYTE |
| SEQ ID NO: 448 | 171924 | g181884 | Human dystrophin gene, exon 44. |
| SEQ ID NO: 449 | 1728875 | g181040 | Human cAMP response element regulatory protein (CREB2) mRNA, complete gb100pri |
| SEQ ID NO: 450 | 1730829 | g1145293 | MIHB |
| SEQ ID NO: 451 | 1736515 | g1944454 | Mouse mRNA for Kryn, complete cds. |
| SEQ ID NO: 452 | 173727 | g2408231 | *Homo sapiens* lysosomal pepstatin insensitive protease (CLN2) mRNA, |
| SEQ ID NO: 453 | 1739540 | g1199745 | hamster NADPH-cytochrome P450 oxidoreductase. |
| SEQ ID NO: 454 | 174139 | INCYTE | INCYTE |
| SEQ ID NO: 455 | 174396 | g726392 | F25B5 |
| SEQ ID NO: 456 | 174675 | INCYTE | INCYTE |
| SEQ ID NO: 457 | 1748866 | g553971 | Ig H-chain (V-region VHD6.96) |
| SEQ ID NO: 458 | 1749560 | g1684889 | Human soluble protein Jagged mRNA, partial cds. |
| SEQ ID NO: 459 | 1749882 | g713204 | *Homo sapiens* CDNA clone 112101 5' similar to SP:CPG1_RABIT P24461 CYTOCHROME P450 IIG1 |
| SEQ ID NO: 460 | 001750 | g842696 | *Homo sapiens* CDNA clone 141589 5' similar to SP:S26076 S26076 DNA-BINDING PROTEIN - |
| SEQ ID NO: 461 | 176361 | INCYTE | INCYTE |
| SEQ ID NO: 462 | 176898 | g2280479 | Human mRNA for KIAA0346 gene, partial cds |
| SEQ ID NO: 463 | 177044 | INCYTE | INCYTE |
| SEQ ID NO: 464 | 1772802 | g53040 | Mouse myeloid differentiation primary response mRNA encoding MyD116 protein |
| SEQ ID NO: 465 | 177384 | INCYTE | INCYTE |
| SEQ ID NO: 466 | 177562 | g460085 | Human BTK region clone ftp-3 mRNA. |
| SEQ ID NO: 467 | 177606 | INCYTE | INCYTE |
| SEQ ID NO: 468 | 177867 | INCYTE | INCYTE |
| SEQ ID NO: 469 | 178337 | g1345423 | drs consensus repeat domain: nt120–174; consensus repeat domain: nt262–317; consensus repeat domain: nt57–115; transmembrane domain: nt376–413. |
| SEQ ID NO: 470 | 181611 | g2315988 | Human putative copper uptake protein (hCTR2) mRNA, complete cds. |
| SEQ ID NO: 471 | 1844277 | g901095 | *Homo sapiens* cDNA clone 182255 5' similar to contains Alu repetitive element;. |
| SEQ ID NO: 472 | 1852619 | g995826 | Skp2; cyclin A CDK2-associated p45 |
| SEQ ID NO: 473 | 1862092 | g1353236 | Mouse T cell transcription factor NFAT1 |
| SEQ ID NO: 474 | 1873202 | g2351804 | Human clone HL9 monocyte inhibitory receptor precursor mRNA, complete |
| SEQ ID NO: 475 | 1876702 | BL01066B | Hypothetical YBR002c family proteins. |
| SEQ ID NO: 476 | 1878710 | g2370077 | Human DNA sequence from PAC 339A18 on chromosome Xp11.2. Contains KIAA0178 gene, similar to mitosis-specific chromosome segregation protein SMC1 of *S.cerevisiae*, DNA binding protein similar to URE-B1, ESTs and STS. |
| SEQ ID NO: 477 | 1878722 | INCYTE | INCYTE |
| SEQ ID NO: 478 | 1878957 | g32391 | HOX4C; homeobox |
| SEQ ID NO: 479 | 1905986 | g219667 | Human plasma (extracellular) mRNA for glutathione peroxidase, complete cds. |
| SEQ ID NO: 480 | 1906277 | g475005 | Human mRNA for T-cell acute lymphoblastic leukemia associated antigen 1906277 |

TABLE 1-continued

| | | | |
|---|---|---|---|
| SEQ ID NO: 481 | 1908804 | g1809219 | human K+ channel beta 2 subunit mRNA, complete cds. |
| SEQ ID NO: 482 | 1912826 | g189991 | Human (clone lambda-hPKC-gamma6) protein kinase C-gamma (PRKCG) mRNA, 5' end cds. |
| SEQ ID NO: 483 | 1914645 | g1375485 | CDC37 homolog |
| SEQ ID NO: 484 | 192279 | INCYTE | INCYTE |
| SEQ ID NO: 485 | 1922816 | g178984 | Human ADP-ribosylation factor 4 (ARF4) mRNA, complete cds. |
| SEQ ID NO: 486 | 1927932 | g1370103 | H.sapiens mRNA for C-C chemokine receptor-4. |
| SEQ ID NO: 487 | 1940690 | g1702921 | H.sapiens mRNA for neurogranin. |
| SEQ ID NO: 488 | 1940966 | g1167906 | COL18A1; alpha-1XVIII collagen |
| SEQ ID NO: 489 | 194278 | INCYTE | INCYTE |
| SEQ ID NO: 490 | 1959635 | g2351377 | Human translation initiation factor eIF3 p66 subunit mRNA, complete |
| SEQ ID NO: 491 | 197958 | INCYTE | INCYTE |
| SEQ ID NO: 492 | 198126 | INCYTE | INCYTE |
| SEQ ID NO: 493 | 199094 | INCYTE | INCYTE |
| SEQ ID NO: 494 | 199150 | INCYTE | INCYTE |
| SEQ ID NO: 495 | 199173 | INCYTE | INCYTE |
| SEQ ID NO: 496 | 199305 | INCYTE | INCYTE |
| SEQ ID NO: 497 | 199690 | g1184317 | Human inhibitor of apoptosis protein 2 mRNA, complete cds. |
| SEQ ID NO: 498 | 199812 | INCYTE | INCYTE |
| SEQ ID NO: 499 | 1999147 | g1041680 | Rattus norvegicus phospholipase A-2-activating protein (plap) mRNA, complete cds. |
| SEQ ID NO: 500 | 200015 | INCYTE | INCYTE |
| SEQ ID NO: 501 | 200044 | g1136395 | Human mRNA for KIAA0168 gene, complete cds. gb100pri |
| SEQ ID NO: 502 | 200097 | INCYTE | INCYTE |
| SEQ ID NO: 503 | 200212 | INCYTE | INCYTE |
| SEQ ID NO: 504 | 2006402 | g1216374 | Rat Tclone4 mRNA. |
| SEQ ID NO: 505 | 200844 | INCYTE | INCYTE |
| SEQ ID NO: 506 | 201349 | INCYTE | INCYTE |
| SEQ ID NO: 507 | 201358 | INCYTE | INCYTE |
| SEQ ID NO: 508 | 201392 | BL00257 | Bombesin-like peptides family proteins. |
| SEQ ID NO: 509 | 201507 | INCYTE | INCYTE |
| SEQ ID NO: 510 | 2016903 | g247306 | cytochrome P450 reductase [human, placenta, mRNA Partial, 2403 nt] |
| SEQ ID NO: 511 | 201696 | INCYTE | INCYTE |
| SEQ ID NO: 512 | 202259 | INCYTE | INCYTE |
| SEQ ID NO: 513 | 2024815 | g35496 | H.sapiens mRNA for protein kinase C gamma (partial). |
| SEQ ID NO: 514 | 203852 | g1177434 | H.sapiens mRNA for unknown 14 kDa protein. |
| SEQ ID NO: 515 | 203960 | g189675 | Human vacuolar H+ ATPase proton channel subunit mRNA, complete cds. |
| SEQ ID NO: 516 | 204502 | INCYTE | INCYTE |
| SEQ ID NO: 517 | 2045226 | INCYTE | INCYTE |
| SEQ ID NO: 518 | 2048834 | g2253262 | Rattus norvegicus neuronal pentraxin receptor mRNA, complete cds |
| SEQ ID NO: 519 | 205155 | g2244605 | Human gene for TMEM1 and PWP2, complete a |
| SEQ ID NO: 520 | 2059533 | g183802 | Human alpha-globin gene cluster on chromosome 16, pseudogene psi-a2 |
| SEQ ID NO: 521 | 206130 | INCYTE | INCYTE |
| SEQ ID NO: 522 | 2062218 | g2224541 | KIAA0300 |
| SEQ ID NO: 523 | 206465 | INCYTE | INCYTE |
| SEQ ID NO: 524 | 206520 | g50003 | Mouse mRNA for adipocyte p27 protein. |
| SEQ ID NO: 525 | 206587 | INCYTE | INCYTE |
| SEQ ID NO: 526 | 206638 | INCYTE | INCYTE |
| SEQ ID NO: 527 | 207052 | g2370071 | Human DNA sequence from PAC 204E5 on chromosome 12. Contains exon |
| SEQ ID NO: 528 | 207681 | g1730287 | Human acetolactate synthase homolog mRNA, complete cds. |
| SEQ ID NO: 529 | 2079250 | g1226237 | Mus musculus cytochrome P450 Cyp7b1 mRNA, complete cds |
| SEQ ID NO: 530 | 2100016 | g313837 | A.thaliana gene for hemC. |
| SEQ ID NO: 53i | 212088 | g1845344 | Human placental equilibrative nucleoside transporter 1 (hENT1) mRNA, complete cds. |
| SEQ ID NO: 532 | 2130869 | INCYTE | INCYTE |
| SEQ ID NO: 533 | 213940 | INCYTE | INCYTE |
| SEQ ID NO: 534 | 215150 | g644878 | Human Gps1 (GPS1) mRNA, complete cds. |
| SEQ ID NO: 535 | 2160348 | g431321 | EC 3.4.16; cleaves C-terminal amino acids linked to penultimate proline; prolylcarboxypeptidase |
| SEQ ID NO: 536 | 216982 | INCYTE | INCYTE |
| SEQ ID NO: 537 | 216991 | INCYTE | INCYTE |

TABLE 1-continued

| | | | |
|---|---|---|---|
| SEQ ID NO: 538 | 021786 | g1099250 | *Homo sapiens* cDNA clone 231999 3' |
| SEQ ID NO: 539 | 2186852 | g24762 | *H.sapiens* mRNA fragment for alpha-2 macroglobulin receptor. |
| SEQ ID NO: 540 | 2192167 | g1150648 | EC 2.4.1.83; dolichyl-phosphate-mannose synthase |
| SEQ ID NO: 541 | 2198554 | g306811 | glutathione S-transferase |
| SEQ ID NO: 542 | 2203436 | g1679778 | Human nucleosome assembly protein 2 mRNA, complete cds. |
| SEQ ID NO: 543 | 221877 | g1336022 | Human HeLa mRNA isolated as a false positive in a two-hybrid-screen. |
| SEQ ID NO: 544 | 2219639 | g2463647 | *Mus musculus* snRNP core Sm protein homolog Sm-X5 (Sm-X5) gene, two |
| SEQ ID NO: 545 | 2220010 | g1508382 | *H.sapiens* flow-sorted chromosome 6 HindIII fragment, SC6pA22F2. |
| SEQ ID NO: 546 | 2223685 | g510281 | Human mRNA for kinesin-related protein, partial cds. |
| SEQ ID NO: 547 | 222689 | g189569 | Human plasminogen activator inhibitor 1 (PAI-1) gene, exon 2. |
| SEQ ID NO: 548 | 224798 | g832913 | Human high molecular weight B cell growth factor mRNA sequence. |
| SEQ ID NO: 549 | 2252906 | g303602 | Human mRNA for cytochrome P-450LTBV. |
| SEQ ID NO: 550 | 2256528 | g206619 | Rat 5S RNA gene, clone 5S-6 |
| SEQ ID NO: 551 | 2258960 | PubEST | PubEST |
| SEQ ID NO: 552 | 2259319 | g1552995 | Human erythroid-specific transcription factor EKLF mRNA, complete cds. |
| SEQ ID NO: 553 | 2270581 | g248 | CI-B9; EC 1.6.99; NADH dehydrogenase |
| SEQ ID NO: 554 | 2271485 | g36556 | *H.sapiens* Sox-8 mRNA. |
| SEQ ID NO: 555 | 2279032 | g2317645 | *Homo sapiens* mRNA for smallest subunit of ubiquinol-cytochrome c reductase, complete cds. |
| SEQ ID NO: 556 | 2284186 | g699497 | IkB beta |
| SEQ ID NO: 557 | 2315951 | g1301622 | C08B6 |
| SEQ ID NO: 558 | 2349047 | g829619 | Fas interacting protein; cell death; RIP |
| SEQ ID NO: 559 | 2353627 | g191228 | Hamster uridine diphosphate N-acetyl D-glucosamine dolichol phosphate N-acetyl-glucosamine-1 phosphatetransferase mRNA |
| SEQ ID NO: 560 | 2356044 | g1429348 | NHP2; high-mobility-group protein |
| SEQ ID NO: 561 | 2365149 | g1161342 | Mouse interleukin 17 receptor mRNA, comp |
| SEQ ID NO: 562 | 236660 | INCYTE | INCYTE |
| SEQ ID NO: 563 | 237704 | INCYTE | INCYTE |
| SEQ ID NO: 564 | 239988 | INCYTE | INCYTE |
| SEQ ID NO: 565 | 240885 | INCYTE | *Homo sapiens* interleukin 9 receptor (IL9R) gene, complete cds. |
| SEQ ID NO: 566 | 2448372 | g1550782 | *M.musculus* mRNA for transcription factor BARX1. 2448372 |
| SEQ ID NO: 567 | 2471348 | g951301 | *M.musculus* GEG-154 mRNA. |
| SEQ ID NO: 568 | 2473119 | g307437 | Human pre-mRNA splicing factor SRp75 mRNA, complete cds. |
| SEQ ID NO: 569 | 255361 | INCYTE | INCYTE |
| SEQ ID NO: 570 | 257321 | INCYTE | INCYTE |
| SEQ ID NO: 571 | 263518 | g55820 | *R.norvegicus* mRNA for brain-derived neurotrophic factor (exon IV). |
| SEQ ID NO: 572 | 264226 | INCYTE | INCYTE |
| SEQ ID NO: 573 | 270483 | g1854034 | Human Cdc5-related protein (PCDC5RP) mRNA, complete cds. |
| SEQ ID NO: 574 | 274605 | INCYTE | INCYTE |
| SEQ ID NO: 575 | 275010 | g1753108 | Human cyclin A1 mRNA, complete cds. |
| SEQ ID NO: 576 | 2804907 | g866469 | *Homo sapiens* cDNA clone 150936 5' similar to contains Alu repetitive element |
| SEQ ID NO: 576 | 2804907 | g292359 | Human NFG genomic fragment. |
| SEQ ID NO: 577 | 285202 | g165652 | protein kinase delta |
| SEQ ID NO: 578 | 287240 | g1009451 | *S.pombe* chromosome I cosmid c22G7 |
| SEQ ID NO: 579 | 287586 | INCYTE | INCYTE |
| SEQ ID NO: 580 | 288492 | g1291337 | Soares fetal lung NbHL19W *Homo sapiens* cDNA clone 301455 5' similar to WP:W06B4.2 CE02891 |
| SEQ ID NO: 581 | 289171 | INCYTE | INCYTE |
| SEQ ID NO: 582 | 290214 | INCYTE | INCYTE |
| SEQ ID NO: 583 | 290510 | g1665778 | Human mRNA for KIAA0256 gene, complete cds. |
| SEQ ID NO: 584 | 290628 | INCYTE | INCYTE |
| SEQ ID NO: 585 | 291736 | INCYTE | INCYTE |
| SEQ ID NO: 586 | 2918759 | g338630 | Human synaptobrevin 2 (SYB2) gene, exon 5. |
| SEQ ID NO: 587 | 2922560 | INCYTE | INCYTE |

TABLE 1-continued

| | | | |
|---|---|---|---|
| SEQ ID NO: 588 | 029244 | g756234 | *Homo sapiens* cDNA clone 125197 5' similar to gb:M14565 CYTOCHROME P450 XIA1, MITOCHONDRIAL (HUMAN) |
| SEQ ID NO: 589 | 292708 | INCYTE | INCYTE |
| SEQ ID NO: 590 | 3038216 | g1469884 | KIAA0151 |
| SEQ ID NO: 591 | 3043265 | PubEST | PubEST |
| SEQ ID NO: 592 | 3044325 | g788133 | *Homo sapiens* cDNA clone 134940 5' similar to contains Alu repetitive element |
| SEQ ID NO: 593 | 309389 | INCYTE | INCYTE |
| SEQ ID NO: 594 | 3100562 | g516680 | Chicken gene for c-maf proto-oncogene product c-Maf, short form yv87e05 |
| SEQ ID NO: 595 | 310202 | g2415582 | *Homo sapiens* mRNA for Marenostrin protein, complete. |
| SEQ ID NO: 596 | 310487 | g33942G | Human T cell-specific protein (RANTES) mRNA, complete cds. |
| SEQ ID NO: 597 | 3125445 | g2224588 | Human mRNA for KIAA0324 gene, partial cds. |
| SEQ ID NO: 598 | 318358 | g2224600 | Human mRNA for KIAA0330 gene, partial cds. |
| SEQ ID NO: 599 | 318438 | INCYTE | INCYTE |
| SEQ ID NO: 600 | 318444 | INCYTE | INCYTE |
| SEQ ID NO: 601 | 318774 | g1064915 | *H.sapiens* mRNA for ubiquitin conjugating enzyme, UbcH7. |
| SEQ ID NO: 602 | 3188122 | g2266637 | Human OB-RGRP gene. |
| SEQ ID NO: 603 | 3191066 | g2280475 | Human mRNA for KIAA0315 gene, partial cds. |
| SEQ ID NO: 604 | 319684 | INCYTE | INCYTE |
| SEQ ID NO: 605 | 320014 | g1558796 | *Homo sapiens* cDNA clone 525535 5' similar to SPA1 MOUSE P46062 GTPASE-ACTIVATING PROTEIN SPA-1 |
| SEQ ID NO: 606 | 320811 | INCYTE | INCYTE |
| SEQ ID NO: 607 | 321651 | INCYTE | INCYTE |
| SEQ ID NO: 608 | 334959 | INCYTE | INCYTE |
| SEQ ID NO: 609 | 335100 | INCYTE | INCYTE |
| SEQ ID NO: 610 | 336724 | INCYTE | INCYTE |
| SEQ ID NO: 611 | 338196 | INCYTE | INCYTE |
| SEQ ID NO: 612 | 338339 | INCYTE | INCYTE |
| SEQ ID NO: 613 | 338345 | INCYTE | INCYTE |
| SEQ ID NO: 614 | 338368 | INCYTE | INCYTE |
| SEQ ID NO: 615 | 338435 | INCYTE | INCYTE |
| SEQ ID NO: 616 | 339045 | INCYTE | INCYTE |
| SEQ ID NO: 617 | 339198 | INCYTE | INCYTE |
| SEQ ID NO: 618 | 339335 | INCYTE | INCYTE |
| SEQ ID NO: 619 | 339678 | INCYTE | INCYTE |
| SEQ ID NO: 620 | 339997 | INCYTE | INCYTE |
| SEQ ID NO: 621 | 340100 | INCYTE | INCYTE |
| SEQ ID NO: 622 | 340318 | INCYTE | INCYTE |
| SEQ ID NO: 623 | 340422 | INCYTE | INCYTE |
| SEQ ID NO: 624 | 340450 | INCYTE | INCYTE |
| SEQ ID NO: 625 | 340883 | INCYTE | INCYTE |
| SEQ ID NO: 626 | 341595 | INCYTE | INCYTE |
| SEQ ID NO: 627 | 342342 | g806765 | Human 76 kDa tyrosine phosphoprotein SLP-76 mRNA, complete cds. |
| SEQ ID NO: 628 | 343466 | INCYTE | INCYTE |
| SEQ ID NO: 629 | 343595 | g1184698 | Human tyrosyl-tRNA synthetase mRNA, complete cds |
| SEQ ID NO: 630 | 343619 | BL00425A | Arthropod defensins proteins. |
| SEQ ID NO: 631 | 344012 | INCYTE | INCYTE |
| SEQ ID NO: 632 | 345315 | INCYTE | INCYTE |
| SEQ ID NO: 633 | 345380 | g337810 | Human MAR/SAR DNA binding protein (SATB1) mRNA, complete cds. |
| SEQ ID NO: 634 | 345409 | INCYTE | INCYTE |
| SEQ ID NO: 635 | 345472 | INCYTE | INCYTE |
| SEQ ID NO: 636 | 346439 | INCYTE | INCYTE |
| SEQ ID NO: 637 | 346597 | g8651 | Mst87F; structural sperm protein |
| SEQ ID NO: 638 | 346869 | g2257694 | *Homo sapiens* mRNA for SCGF, complete cds. |
| SEQ ID NO: 639 | 347184 | g1197073 | GEF1 |
| SEQ ID NO: 640 | 003490 | g30337 | Human CYP2D7BP pseudogene for cytochrome |
| SEQ ID NO: 641 | 349715 | INCYTE | INCYTE |
| SEQ ID NO: 642 | 3518373 | g2282039 | *Homo sapiens* Arp2/3 protein complex subunit p20-Arc (ARC20) mRNA |
| SEQ ID NO: 643 | 3523611 | g1710211 | Human clone 23732 mRNA, partial cds |
| SEQ ID NO: 644 | 3534074 | g19867 | extensin (AA 1–620) |
| SEQ ID NO: 645 | 3538629 | g1386895 | Soares fetal heart NbHH19W *Homo sapiens* cDNA clone 345320 5' simiiar to SWLCOGY_MOUSE Q02853 STROMELYSIN-3 PRECURSOR |

TABLE 1-continued

| | | | |
|---|---|---|---|
| SEQ ID NO: 646 | 358673 | g2465410 | *Homo sapiens* Bcl-1/Bcl-2 binding protein (BAD) mRNA, partial cds |
| SEQ ID NO: 647 | 361577 | g189389 | *Homo sapiens* osteogenic protein-2 (OP-2) mRNA, complete cds. |
| SEQ ID NO: 648 | 369126 | g1905905 | *Homo sapiens* DNA from chromosome 19p13.2 cosmids R31240, R30272 and R28549 containing the EKLF, GCDH, CRTC, and RAD23A genes, genomic sequence. |
| SEQ ID NO: 649 | 375230 | g2505956 | *Rattus norvegicus* mRNA for 70 kDa tumor specific antigen, partial. |
| SEQ ID NO: 650 | 375755 | g1924939 | *H.sapiens* mRNA for myosin-IE. |
| SEQ ID NO: 651 | 377250 | INCYTE | INCYTE |
| SEQ ID NO: 652 | 377292 | INCYTE | INCYTE |
| SEQ ID NO: 653 | 380124 | g1800224 | Human JAK3 gene, complete cds. |
| SEQ ID NO: 654 | 383060 | g556529 | Mouse mRNA for arylhydrocarbon receptor |
| SEQ ID NO: 655 | 383280 | BL01066B | Hypothetical YBR002c family proteins. |
| SEQ ID NO: 656 | 388684 | BL00881B | Protein splicing proteins. |
| SEQ ID NO: 657 | 389702 | INCYTE | INCYTE |
| SEQ ID NO: 658 | 390602 | INCYTE | INCYTE |
| SEQ ID NO: 659 | 394012 | g1483249 | C52E4 |
| SEQ ID NO: 660 | 003945 | g1151653 | *Homo sapiens* cDNA clone 265499 5' similar to WP:C38C10.2 CE00105 SODIUM/PHOSPHATE TRANSPORTER |
| SEQ ID NO: 661 | 400581 | g288564 | *H.sapiens* TOP2 mRNA for DNA topoisomerase II (partial). |
| SEQ ID NO: 662 | 401022 | INCYTE | INCYTE |
| SEQ ID NO: 663 | 401043 | g458904 | YHR163w |
| SEQ ID NO: 664 | 401587 | g339947 | Human tropomodulin mRNA, complete cds. |
| SEQ ID NO: 665 | 402766 | g38014 | Human mRNA for zinc finger protein (clone 431) |
| SEQ ID NO: 666 | 406422 | INCYTE | INCYTE |
| SEQ ID NO: 667 | 407527 | INCYTE | INCYTE |
| SEQ ID NO: 668 | 409041 | g2209028 | *Homo sapiens* ribonuclease 6 precursor, mRNA, complete cds. |
| SEQ ID NO: 669 | 413341 | BL00509B | Ras GTPase-activating proteins. |
| SEQ ID NO: 670 | 415659 | INCYTE | INCYTE |
| SEQ ID NO: 671 | 427571 | g38317 | Human mRNA for nuclear p68 protein. |
| SEQ ID NO: 672 | 437714 | g532118 | cytochrome P450 |
| SEQ ID NO: 673 | 440958 | INCYTE | INCYTE |
| SEQ ID NO: 674 | 441128 | g2274843 | *Schizosaccharomyces pombe* gene for carboxypeptidase Y, complete cds. |
| SEQ ID NO: 675 | 441141 | INCYTE | INCYTE |
| SEQ ID NO: 676 | 441180 | INCYTE | INCYTE |
| SEQ ID NO: 677 | 441337 | INCYTE | INCYTE |
| SEQ ID NO: 678 | 441539 | g189210 | Human Nil-2-a zinc finger protein mRNA, 3' flank. |
| SEQ ID NO: 679 | 441541 | INCYTE | INCYTE |
| SEQ ID NO: 680 | 441865 | INCYTE | INCYTE |
| SEQ ID NO: 681 | 443093 | g559419 | C38D4.5 |
| SEQ ID NO: 682 | 443710 | g929659 | *H.sapiens* mRNA for PQ-rich protein. |
| SEQ ID NO: 683 | 444827 | INCYTE | INCYTE |
| SEQ ID NO: 684 | 445186 | g1840405 | membrane guanylyl cyclase OLGC5 |
| SEQ ID NO: 685 | 447212 | g1220319 | *Homo sapiens* H2K binding factor 2 (KBF2) mRNA, complete cds. |
| SEQ ID NO: 686 | 447323 | INCYTE | INCYTE |
| SEQ ID NO: 687 | 447687 | INCYTE | INCYTE |
| SEQ ID NO: 688 | 448520 | INCYTE | INCYTE |
| SEQ ID NO: 689 | 450088 | g498720 | *H.sapiens* HZF10 mRNA for zinc finger protein. |
| SEQ ID NO: 690 | 451538 | g1857330 | Human SPS1/STE20 homolog KHS1 mRNA, complete cds. |
| SEQ ID NO: 691 | 469895 | g1039418 | Human tyrosine protein kinase (Jak3B) splice variant mRNA, complete gb100pri |
| SEQ ID NO: 692 | 470564 | g1931580 | Human macrophage-derived chemokine precursor (MDC) mRNA, complete |
| SEQ ID NO: 693 | 475569 | INCYTE | INCYTE |
| SEQ ID NO: 694 | 476160 | g35206 | Human mRNA for cytochrome P-450IIB6. |
| SEQ ID NO: 695 | 476365 | INCYTE | INCYTE |
| SEQ ID NO: 696 | 478861 | g1502408 | Human CC chemokine receptor 5 mRNA, complete cds. |
| SEQ ID NO: 696 | 478861 | g1457945 | Human CC chemokine receptor 5 (CCR5) mRNA, complete cds. |
| SEQ ID NO: 696 | 478861 | g1502408 | Human CC chemokine receptor 5 mRNA, complete cds. |
| SEQ ID NO: 697 | 479403 | INCYTE | INCYTE |
| SEQ ID NO: 698 | 486270 | g298664 | CD68 = 110 kda transmembrane glycoprotein [human, promonocyte cell lin |

TABLE 1-continued

| | | | |
|---|---|---|---|
| SEQ ID NO: 699 | 488842 | g632961 | *Homo sapiens* clk1 mRNA, complete cds. |
| SEQ ID NO: 700 | 493135 | g1381148 | Hs-CUL-4A; Hs-cul-4A |
| SEQ ID NO: 701 | 497005 | INCYTE | INCYTE |
| SEQ ID NO: 702 | 497024 | INCYTE | INCYTE |
| SEQ ID NO: 703 | 497034 | INCYTE | INCYTE |
| SEQ ID NO: 704 | 497391 | INCYTE | INCYTE |
| SEQ ID NO: 705 | 497471 | INCYTE | INCYTE |
| SEQ ID NO: 706 | 497557 | INCYTE | INCYTE |
| SEQ ID NO: 707 | 497670 | INCYTE | INCYTE |
| SEQ ID NO: 708 | 497826 | INCYTE | INCYTE |
| SEQ ID NO: 709 | 497850 | INCYTE | INCYTE |
| SEQ ID NO: 710 | 497960 | INCYTE | INCYTE |
| SEQ ID NO: 711 | 497994 | INCYTE | INCYTE |
| SEQ ID NO: 712 | 498105 | g1669680 | Human DNA sequence from PAC 293E14 contains ESTs, STS. |
| SEQ ID NO: 713 | 498294 | INCYTE | INCYTE |
| SEQ ID NO: 714 | 498387 | INCYTE | INCYTE |
| SEQ ID NO: 715 | 498413 | INCYTE | INCYTE |
| SEQ ID NO: 716 | 498540 | INCYTE | INCYTE |
| SEQ ID NO: 717 | 498630 | INCYTE | INCYTE |
| SEQ ID NO: 718 | 498780 | INCYTE | INCYTE |
| SEQ ID NO: 719 | 499243 | INCYTE | INCYTE |
| SEQ ID NO: 720 | 499486 | INCYTE | INCYTE |
| SEQ ID NO: 721 | 499526 | INCYTE | INCYTE |
| SEQ ID NO: 722 | 499553 | g1619273 | COS1.3 |
| SEQ ID NO: 723 | 499608 | INCYTE | INCYTE |
| SEQ ID NO: 724 | 500205 | INCYTE | INCYTE |
| SEQ ID NO: 725 | 500677 | INCYTE | INCYTE |
| SEQ ID NO: 726 | 500726 | INCYTE | INCYTE |
| SEQ ID NO: 727 | 501612 | INCYTE | INCYTE |
| SEQ ID NO: 728 | 501746 | INCYTE | INCYTE |
| SEQ ID NO: 729 | 502018 | INCYTE | INCYTE |
| SEQ ID NO: 730 | 502031 | INCYTE | INCYTE |
| SEQ ID NO: 731 | 502964 | INCYTE | INCYTE |
| SEQ ID NO: 732 | 503172 | INCYTE | INCYTE |
| SEQ ID NO: 733 | 504312 | INCYTE | INCYTE |
| SEQ ID NO: 734 | 505309 | g1067025 | R07E5.14 |
| SEQ ID NO: 735 | 505420 | INCYTE | INCYTE |
| SEQ ID NO: 736 | 506770 | INCYTE | INCYTE |
| SEQ ID NO: 737 | 506822 | g11075 | Mst84Dc |
| SEQ ID NO: 738 | 507473 | g2281121 | cysteine protease inhibitor; cystatin C |
| SEQ ID NO: 739 | 508644 | g1122807 | F49C12.12 |
| SEQ ID NO: 740 | 512988 | g34625 | Human gene for melanoma growth stimulatory activity (MGSA). |
| SEQ ID NO: 741 | 513237 | g1552243 | Rat liver mRNA for lysophospholipase, complete cds. |
| SEQ ID NO: 742 | 516292 | g1800302 | Human HIV-1 Nef interacting protein (Nip7-1) mRNA, partial cds. |
| SEQ ID NO: 743 | 520251 | g485107 | C18F10weakly similar to ANK repeat region of Fowlpox virus BamHI-orf7 protein |
| SEQ ID NO: 744 | 523661 | INCYTE | INCYTE |
| SEQ ID NO: 745 | 531728 | g1293686 | transcription factor C1 HCF |
| SEQ ID NO: 746 | 543880 | g166693 | intron splice site between bp 1278 . . . 1279[*Arabidopsis thaliana* recombination and DNA-damage resistance protein (DRT111) mRNA, complete cds.], gene product. |
| SEQ ID NO: 747 | 543972 | g1066996 | K03H1 |
| SEQ ID NO: 748 | 548896 | g1055166 | T13C2 |
| SEQ ID NO: 749 | 553078 | g1806039 | *H.sapiens* mRNA for adipophilin. |
| SEQ ID NO: 750 | 555803 | INCYTE | INCYTE |
| SEQ ID NO: 751 | 556635 | INCYTE | INCYTE |
| SEQ ID NO: 752 | 557918 | g190220 | EC 3.1.3.16; protein phosphatase 2A 130 |
| SEQ ID NO: 753 | 559785 | INCYTE | INCYTE |
| SEQ ID NO: 754 | 561790 | INCYTE | INCYTE |
| SEQ ID NO: 755 | 561825 | g49442 | Guinea pig mRNA for platelet activating factor (PAF) receptor |
| SEQ ID NO: 756 | 562315 | g1050967 | *Mus musculus* epsilon tyrosine phosphatase (Ptpre) mRNA, transmembranal isoform, complete cds |
| SEQ ID NO: 757 | 562700 | g1183162 | cyclin I |
| SEQ ID NO: 758 | 566890 | g1255239 | Human lysosomal-associated multitransmembrane protein (LAPTm5) mRNA |
| SEQ ID NO: 759 | 567375 | INCYTE | INCYTE |
| SEQ ID NO: 760 | 569293 | INCYTE | INCYTE |
| SEQ ID NO: 761 | 569414 | INCYTE | INCYTE |
| SEQ ID NO: 762 | 569493 | g1359580 | Human copine I mRNA, complete cds. |

TABLE 1-continued

| | | | |
|---|---|---|---|
| SEQ ID NO: 763 | 569636 | g1688075 | Human tetratricopeptide repeat protein (tpr2) mRNA, complete cds. |
| SEQ ID NO: 764 | 570733 | INCYTE | INCYTE |
| SEQ ID NO: 765 | 585906 | g437781 | *H.sapiens* mRNA for alpha 7B integrin. |
| SEQ ID NO: 766 | 589345 | g1773292 | Human tissue inhibitor of metalloproteinase 4 mRNA, complete cds. |
| SEQ ID NO: 767 | 598696 | g1575303 | Human proto-oncogene (FRAT1) gene, complete cds. |
| SEQ ID NO: 768 | 602872 | g1054740 | *H.sapiens* DMA, DMB, HLA-Z1, IPP2, LMP2, TAP1, LMP7, TAP2, DOB, DQB2 and RING8, 9, 13 and 14 genes. |
| SEQ ID NO: 769 | 604657 | INCYTE | INCYTE |
| SEQ ID NO: 770 | 607227 | INCYTE | INCYTE |
| SEQ ID NO: 771 | 620417 | g1749367 | Human mRNA for NOTCH4, partial cds. |
| SEQ ID NO: 772 | 622708 | g609305 | Human cocaine and amphetamine regulated transcript CART (hCART) mRNA, complete cds. |
| SEQ ID NO: 773 | 626570 | INCYTE | INCYTE |
| SEQ ID NO: 774 | 627856 | g498909 | Human endothelial-monocyte activating polypeptide II mRNA, complete cds. |
| SEQ ID NO: 775 | 634343 | g468824 | EC 3.5.1.12; biotinidase |
| SEQ ID NO: 776 | 635562 | g1103872 | *Mus musculus* putative G protein-coupled receptor TDAG8 (TDAG8) mRNA, complete cds. |
| SEQ ID NO: 777 | 637984 | g1732425 | Human TNF receptor associated factor 6 (TRAF6) mRNA, complete cds. |
| SEQ ID NO: 778 | 640287 | INCYTE | INCYTE |
| SEQ ID NO: 779 | 640544 | g1110498 | Human transforming growth factor-beta type II receptor (TGF-beta RII), promoter region. |
| SEQ ID NO: 780 | 642272 | g201107 | Mouse adipocyte-specific mRNA, partial |
| SEQ ID NO: 781 | 643784 | g1216375 | Rat clone N27 mRNA. |
| SEQ ID NO: 782 | 660821 | g1562534 | csdp; single-strand DNA-binding |
| SEQ ID NO: 783 | 662097 | g2326942 | *Xenopus laevis* mRNA for Fizzy-related protein. |
| SEQ ID NO: 784 | 664692 | g2326226 | *Homo sapiens* phosphatidylinositol 4-kinase 230 (pi4K230) mRNA, |
| SEQ ID NO: 785 | 667680 | g303620 | RCC1 |
| SEQ ID NO: 786 | 675530 | g184427 | heat shock protein G2; heparan sulfate proteoglycan |
| SEQ ID NO: 787 | 677833 | g2224726 | Human mRNA for KIAA0393 gene, complete cds. |
| SEQ ID NO: 788 | 681899 | g206731 | *Rattus norvegicus* large subunit ribosomal protein L36a mRNA, complete |
| SEQ ID NO: 789 | 690282 | INCYTE | INCYTE |
| SEQ ID NO: 790 | 692911 | g984955 | Human connective tissue growth factor mRNA, partial cds. |
| SEQ ID NO: 791 | 693932 | INCYTE | INCYTE |
| SEQ ID NO: 792 | 696057 | INCYTE | INCYTE |
| SEQ ID NO: 793 | 696087 | bBL00257 | Bombesin-like peptides family proteins. |
| SEQ ID NO: 794 | 696390 | INCYTE | INCYTE |
| SEQ ID NO: 795 | 696878 | g1216372 | Human RGP4 mRNA, complete cds. |
| SEQ ID NO: 796 | 697122 | g971274 | Rat mRNA for neurodapl gene. |
| SEQ ID NO: 797 | 699789 | INCYTE | INCYTE |
| SEQ ID NO: 798 | 699889 | INCYTE | INCYTE |
| SEQ ID NO: 799 | 700033 | INCYTE | INCYTE |
| SEQ ID NO: 802 | 702552 | g32106 | Human gene for histone H1(0) |
| SEQ ID NO: 803 | 702628 | g1684902 | Human Cdc6-related protein (HsCDC6) mRNA, complete cds. |
| SEQ ID NO: 804 | 705344 | INCYTE | INCYTE |
| SEQ ID NO: 805 | 706613 | INCYTE | INCYTE |
| SEQ ID NO: 806 | 734113 | INCYTE | INCYTE |
| SEQ ID NO: 808 | 736812 | g1223890 | putative T1/ST2 receptor binding protein precursor |
| SEQ ID NO: 809 | 753522 | g1665792 | Human mRNA for KIAA0263 gene, complete cds. |
| SEQ ID NO: 810 | 757560 | g598675 | Human HepG2 partial cDNA, clone hmd2g05m5 |
| SEQ ID NO: 811 | 758770 | g695584 | *H.sapiens* XAP-4 mRNA for GDP-dissociation inhibitor. |
| SEQ ID NO: 812 | 766493 | g7428 | DhTc3; testis-specific RNA |
| SEQ ID NO: 813 | 768545 | g682722 | *Mus musculus* bacteria binding macrophage receptor MARCO mRNA, complete |
| SEQ ID NO: 814 | 770712 | g1703500 | Human BTG2 (BTG2) mRNA, complete cds |
| SEQ ID NO: 815 | 776108 | g1550785 | iap38; immune-associated protein 38 |
| SEQ ID NO: 816 | 781552 | g248405 | cathepsin S = elastinolytic cysteine protease [human, alveolar] |

TABLE 1-continued

| | | | |
|---|---|---|---|
| SEQ ID NO: 817 | 797908 | g1871153 | Human g16 protein (g16) mRNA, partial cds |
| SEQ ID NO: 818 | 816532 | g606410 | CYP4M2; cytochrome P450 |
| SEQ ID NO: 819 | 816957 | g1147602 | Human BRCA1 gene, partial cds. |
| SEQ ID NO: 820 | 828764 | g403127 | Human gadd45 gene, complete cds. |
| SEQ ID NO: 821 | 836115 | g2506079 | Homo sapiens mRNA for HsGAK, complete cds. |
| SEQ ID NO: 822 | 836623 | g533212 | Homo sapiens secreted T cell protein (H400; SIS-gamma) mRNA, complete 836623 |
| SEQ ID NO: 823 | 857334 | g1813425 | Human mRNA for heat shock transcription factor 4, complete cds. |
| SEQ ID NO: 824 | 859619 | g2425164 | Rattus norvegicus RT1.P1 pseudogene for TL antigen. |
| SEQ ID NO: 825 | 862403 | g567206 | GDF-9; growth factor |
| SEQ ID NO: 826 | 866123 | g1335639 | Pkc53E |
| SEQ ID NO: 827 | 873034 | g1556398 | H.sapiens mRNA for FAN protein. |
| SEQ ID NO: 828 | 873352 | g1695171 | M.musculus mRNA for new member of PDGF/VEGT family of growth factors |
| SEQ ID NO: 829 | 875380 | g1167502 | Human mRNA for TI-227H. |
| SEQ ID NO: 830 | 877276 | g404781 | Rat proto-oncogene (Ets-1) mRNA, complete cds. |
| SEQ ID NO: 831 | 877555 | g56493 | Rat mRNA for integrin alpha-1. |
| SEQ ID NO: 832 | 887176 | g1065506 | C27F2, nearly identical to C. elegans predicted protein F17C8.5 (GB:Z35719) |
| SEQ ID NO: 833 | 893413 | g292062 | Human glutathione S-transferase A3 (GSTA3) gene, exon 4. |
| SEQ ID NO: 834 | 900544 | g659964 | Homo sapiens cDNA clone 72292 5' contains LTR6 repetitive element. |
| SEQ ID NO: 835 | 907936 | g410207 | E2F-2 |
| SEQ ID NO: 836 | 908419 | g796828 | Homo sapiens cDNA clone 137454 5' |
| SEQ ID NO: 837 | 908819 | INCYTE | INCYTE |
| SEQ ID NO: 838 | 918331 | g33798 | H.sapiens gene for interleukin-1 receptor antagonist |
| SEQ ID NO: 839 | 934291 | g2190401 | Homo sapiens mRNA for latent transforming growth factor-beta binding |
| SEQ ID NO: 840 | 935293 | g487835 | Homo sapiens transcription factor mRNA, 5' end. |
| SEQ ID NO: 841 | 949299 | g1916228 | Human line-1 reverse transcriptase gene, partial cds, and granulocyte chemotactic protein-2 (GCP-2) gene, complete cds. |
| SEQ ID NO: 842 | 953491 | g2230872 | H.sapiens mRNA for M phase phosphoprotein 10. |
| SEQ ID NO: 843 | 958978 | g2289785 | Homo sapiens mRNA for HYA22, complete cds. |
| SEQ ID NO: 844 | 959745 | g2072184 | Human osteoprotegerin (OPG) mRNA, complete cds. |
| SEQ ID NO: 845 | 965517 | g1924937 | H.sapiens mRNA for monocyte chemotactic protein 2. |
| SEQ ID NO: 846 | 971847 | PubEST | PubEST |
| SEQ ID NO: 847 | 974618 | g1469002 | C50B8 |
| SEQ ID NO: 848 | 978696 | g511229 | rRAFT1; rapamycin and FKBP12 target-1 protein |
| SEQ ID NO: 849 | 983922 | g202598 | Rat alpha-2-macroglobulin gene, 5' end. |
| SEQ ID NO: 850 | 984212 | g1572718 | Drosophila melanogaster PAST-1 mRNA |
| SEQ ID NO: 851 | 991324 | g1731985 | H.sapiens mRNA for MMP-19 protein. |
| SEQ ID NO: 852 | 991781 | INCYTE | INCYTE |
| SEQ ID NO: 853 | 995140 | g1171561 | H.sapiens brca2 gene exon 9. |
| SEQ ID NO: 854 | 996226 | g1063264 | Mouse mRNA for SCID complementing gene 2. |

| | CLONE ID | ANNOTATION |
|---|---|---|
| SEQ ID NO: 855 | g1000283 | Human selenium donor protein (selD) mRNA, complete cds. |
| SEQ ID NO: 856 | g1004356 | Human KIR (cl-5) NK receptor precursor protein mRNA, complete cds. |
| SEQ ID NO: 857 | g1008914 | Human mRNA for proteasome activator hPA28 subunit beta, complete cds. |
| SEQ ID NO: 858 | g1008970 | H.sapiens mRNA for intracellular IL-1 receptor antagonist type II. |
| SEQ ID NO: 859 | g1015963 | Human T cell surface glycoprotein CD-6 mRNA, complete cds. |
| SEQ ID NO: 860 | g1016272 | Human retinoblastoma-binding protein (RbAp46) mRNA, complete cds. |
| SEQ ID NO: 86i | g1036804 | Human TGF-beta receptor interacting protein 1 mRNA, complete cds. |
| SEQ ID NO: 862 | g1039418 | Human tyrosine protein kinase (Jak3B) splice variant mRNA, complete |

TABLE 1-continued

| | | |
|---|---|---|
| SEQ ID NO: 863 | g1039420 | [human, testis, mRNA, 762 nt]. |
| SEQ ID NO: 864 | g1045058 | *H.sapiens* DS-1 mRNA. |
| SEQ ID NO: 865 | g1048988 | SEQ ID NO: 866 g1049069 Human Gps2 (GPS2) mRNA, complete cds. |
| SEQ ID NO: 866 | g1049069 | Human Gps2 (GPS2) mRNA, complete cds. |
| SEQ ID NO: 867 | g1049089 | Human splicing factor SRp40-2 (SRp40) mRNA, complete cds. |
| SEQ ID NO: 868 | g1050526 | *H.sapiens* mRNA for seryl-tRNA synthetase. |
| SEQ ID NO: 869 | g1050957 | Human chitotriosidase precursor mRNA, complete cds. |
| SEQ ID NO: 870 | g1060913 | Human mRNA for very-long-chain acyl-CoA dehydrogenase (VLCAD), |
| SEQ ID NO: 871 | g1061145 | *H.sapiens* mRNA for E2F-4 protein. |
| SEQ ID NO: 872 | g1063261 | Human GTP cyclohydrolase I gene, exon 6. |
| SEQ ID NO: 873 | g1066270 | *H.sapiens* mRNA for Pr22 protein. |
| SEQ ID NO: 874 | g1079557 | Human Bcl-2 related (Bfl-1) mRNA, complete cds. |
| SEQ ID NO: 875 | g1088447 | Human mRNA for NADP dependent leukotriene b4 12-hydroxydehydrogenase, |
| SEQ ID NO: 876 | g1101785 | Human cell surface glycoprotein CD44 mRNA, complete cds. |
| SEQ ID NO: 877 | g1101910 | Human CDK inhibitor p19INK4d mRNA, complete cds. |
| SEQ ID NO: 878 | g1107697 | *H.sapiens* mRNA for GAIP protein. |
| SEQ ID NO: 879 | g1109791 | Human protein tyrosine phosphatase sigma mRNA, complete cds. |
| SEQ ID NO: 880 | g1119216 | *Homo sapiens* UDP-Galactose 4 epimerase (GALE) gene, complete cds. |
| SEQ ID NO: 881 | g1122218 | Human mNA for platelet activating factor acetylhydrolase IB |
| SEQ ID NO: 882 | g1125055 | Human interleukin-15 receptor alpha chain precursor (IL15RA) mRNA, |
| SEQ ID NO: 883 | g1127832 | Human heat shock protein hsp40 homolog mRNA, complete cds. |
| SEQ ID NO: 884 | g1136797 | Human MAP kinase Mxi2 (MXI2) mRNA, complete cds. |
| SEQ ID NO: 885 | g1139594 | Human leptin receptor (Ob-r) mRNA, complete cds. |
| SEQ ID NO: 886 | g1143491 | *H.sapiens* mRNA for BiP protein. |
| SEQ ID NO: 887 | g1147602 | Human BRCA1 gene, partial cds. |
| SEQ ID NO: 888 | g1149557 | Human TNF-related apoptosis inducing ligand TRAIL mRNA, complete cds. |
| SEQ ID NO: 889 | g1150990 | Human receptor tyrosine kinase Flt4 (short form) mRNA, complete cds. |
| SEQ ID NO: 890 | g1155218 | Human uncoupling protein (UCP) mRNA, complete cds. |
| SEQ ID NO: 891 | g1155222 | NO: 891 g1155222 Human IL-17 mRNA, complete cds |
| SEQ ID NO: 892 | g1160928 | *Homo sapiens* cytoplasmic antiproteinase 3 (CAP3) mRNA, complete cds. |
| SEQ ID NO: 893 | g1160966 | *Homo sapiens* palmitoyl-protein thioesterase gene, complete cds. |
| SEQ ID NO: 894 | g1160974 | *Homo sapiens* TNFR2-TRAF signalling complex protein mRNA, complete |
| SEQ ID NO: 895 | g1161921 | Human p19 protein mRNA, complete cds. |
| SEQ ID NO: 896 | g1163233 | Human homozygous deletion target in pancreatic carcinoma (DPC4) mRNA, |
| SEQ ID NO: 897 | g1166437 | *H.sapiens* mRNA for ATP receptor. |
| SEQ ID NO: 898 | g1174071 | Human G alpha-q (Gaq) mRNA, complete cds. |
| SEQ ID NO: 899 | g1183162 | Human mRNA for cyclin I, complete cds. |
| SEQ ID NO: 900 | g1184319 | Human X-linked inhibitor of apotosis protein XIAP mRNA, complete cds. |
| SEQ ID NO: 901 | g1185439 | Human eotaxin precursor gene, complete cds. |
| SEQ ID NO: 902 | g1185451 | Human cytochrome P450 monooxygenase CYP2J2 mRNA, complete cds. |
| SEQ ID NO: 903 | g1185462 | Human ARF-activated phosphatidylcholine-specific phospholipase D1a |
| SEQ ID NO: 904 | g1196416 | *Homo sapiens* CLP mRNA, partial cds. |
| SEQ ID NO: 905 | g1199579 | Human eosinophil CC chemokine receptor 3 mRNA, complete cds. |
| SEQ ID NO: 906 | g1206008 | Human putative transmembrane receptor IL-1Rrp mRNA, complete cds. |
| SEQ ID NO: 907 | g1215680 | Human tissue inhibitor of metalloproteinases-3 (TIMP3) gene, exon 5, |
| SEQ ID NO: 908 | g1220363 | Human pre-B cell stimulating factor homologue (SDF1a) mRNA, complete |
| SEQ ID NO: 909 | g1235723 | Human mRNA for ESP1/CRP2, complete cds. |
| SEQ ID NO: 910 | g1235901 | Human FRAP-related protein (FRP1) mRNA, complete cds. |
| SEQ ID NO: 911 | g1236078 | Human interleukin-1 receptor-related protein mRNA, complete cds. |
| SEQ ID NO: 912 | g1236232 | *Homo sapiens* cyclin G1 mRNA, complete cds. |
| SEQ ID NO: 913 | g1236234 | *Homo sapiens* cyclin G2 mRNA, complete cds. |

TABLE 1-continued

| | | |
|---|---|---|
| SEQ ID NO: 914 | g1236942 | Human RIP protein kinase gene, complete cds. |
| SEQ ID NO: 915 | g1244767 | Human mucosal addressin cell adhesion molecule-1 (MAdCAM-1) mRNA, |
| SEQ ID NO: 916 | g1245045 | Human specific 116-kDa vacuolar proton pump subunit (OC-116KDa) mRNA, |
| SEQ ID NO: 917 | g1245371 | Human retinoic acid-responsive protein (NN8-4AG) mRNA, complete cds. |
| SEQ ID NO: 918 | g1255719 | Human MEK5 mRNA, complete cds. |
| SEQ ID NO: 919 | g1255924 | *H.sapiens* mRNA for CD40-ligand. |
| SEQ ID NO: 920 | g1256700 | Human CD46 mRNA, complete cds. |
| SEQ ID NO: 921 | g1261911 | *H.sapiens* mRNA for CD5 protein. |
| SEQ ID NO: 922 | g1277177 | Human YMP mRNA, complete cds. |
| SEQ ID NO: 923 | g1289370 | Human Ikaros/LYF-1 homolog (hIk-1) mRNA, complete cds. |
| SEQ ID NO: 924 | g1296608 | *H.sapiens* mRNA for chemokine CC-2 and CC-1. |
| SEQ ID NO: 925 | g1296656 | *H.sapiens* mRNA for MHC class I mic-B antigen. |
| SEQ ID NO: 926 | g1304113 | Human Placenta, Testis mRNA for NPAT gene product, partial cds. |
| SEQ ID NO: 927 | g1311467 | Human RNA for urokinase-type plasminogen activator, partial cds. |
| SEQ ID NO: 928 | g1311504 | CHN = steroid/thyroid orphan receptor homolog gene [human, fetal brain |
| SEQ ID NO: 929 | g1322221 | Human RACH1 (RACH1) mRNA, complete cds. |
| SEQ ID NO: 930 | g1353773 | Human transcription factor NFAT1 isoform B (NFAT1) mRNA, complete |
| SEQ ID NO: 931 | g1354384 | Human Grb2-related adaptor protein (Grap) mRNA, complete cds. |
| SEQ ID NO: 932 | g1369836 | *Homo sapiens* Grb14 mRNA, complete cds. |
| SEQ ID NO: 933 | g1370103 | *H.sapiens* mRNA for C-C chemokine receptor-4. |
| SEQ ID NO: 934 | g1375484 | Human CDC37 homolog mRNA, complete cds. |
| SEQ ID NO: 935 | g1381141 | Human Hs-cul-1 mRNA, complete cds. |
| SEQ ID NO: 936 | g1381145 | Human Hs-cul-3 mRNA, partial cds. |
| SEQ ID NO: 937 | g1381147 | Human Hs-cul-4A mRNA, partial cds. |
| SEQ ID NO: 938 | g1381149 | Human Hs-cul-4A mRNA, partial cds. |
| SEQ ID NO: 939 | g1381163 | Human huntingtin interacting protein (HIP2) mRNA, complete cds. |
| SEQ ID NO: 940 | g1381809 | Human skeletal muscle LIM-protein SLIM2 mRNA, partial cds. |
| SEQ ID NO: 941 | g1401351 | Human apoptotic cysteine protease Mch5 isoform alpha (Mch5) mRNA, |
| SEQ ID NO: 942 | g1403712 | Human chromosome 18 Mad homolog JV18-1 mRNA, complete cds. |
| SEQ ID NO: 943 | g1405318 | Human Liver mRNA for interferon-gamma inducing factor(IGIF), complete |
| SEQ ID NO: 944 | g1418815 | *H.sapiens* FAS/Apo 1 mRNA for FAS soluble protein (clone FAS |
| SEQ ID NO: 945 | g1418931 | *H.sapiens* mRNA for phosphotyrosine phosphatase kappa. |
| SEQ ID NO: 946 | g1418933 | *H.sapiens* mRNA for protein-tyrosine-phosphatase (tissue type: |
| SEQ ID NO: 947 | g1419373 | Human lysosomal alpha-mannosidase (MANB) mRNA, complete cds. |
| SEQ ID NO: 948 | g1431875 | Human cyclin G mRNA, complete cds. |
| SEQ ID NO: 949 | gl439565 | Human chitinase precursor (HUMTCHIT) mRNA, exon 1a form, complete |
| SEQ ID NO: 950 | g1439612 | Human neural cell adhesion molecule CD56 mRNA, complete cds. |
| SEQ ID NO: 951 | g1457945 | Human CC chemokine receptor 5 (CCR5) mRNA, complete cds. |
| SEQ ID NO: 952 | g1463124 | Human JNK3 alpha2 protein kinase (JNK3A2) mRNA, complete cds. |
| SEQ ID NO: 953 | g1463128 | Human JNK2 alpha1 protein kinase (JNK2A1) mRNA, complete cds. |
| SEQ ID NO: 954 | g1468914 | Human mRNA for fructose 6-phosphate,2-kinase/fructose |
| SEQ ID NO: 955 | g1468978 | Human chemokine receptor-like protein (TER1) gene, complete cds. |
| SEQ ID NO: 956 | g1469178 | Human mRNA for KIAA0128 gene, partial cds. |
| SEQ ID NO: 957 | g1478067 | *Homo sapiens* B56-delta mRNA, complete cds. |
| SEQ ID NO: 958 | g1479978 | *Homo sapiens* STAT4 mRNA, complete cds. |
| SEQ ID NO: 959 | g1480480 | Human eosinophil eotaxin receptor (CMKBR3) gene, complete cds. |
| SEQ ID NO: 960 | g1480921 | Human cyclooxygenase-1 (PTSG1) mRNA, partial cds. |
| SEQ ID NO: 961 | g1483349 | *H.sapiens* mRNA for IL13 receptor. |
| SEQ ID NO: 962 | g1486366 | *H.sapiens* PNP1 mRNA. |
| SEQ ID NO: 963 | g1488065 | Human soluble type II interleukin-1 receptor mRNA, complete cds. |
| SEQ ID NO: 964 | g1491709 | *H.sapiens* mRNA for NC2 alpha subunit. |

TABLE 1-continued

| SEQ ID NO: 965 | g1495461 | H.sapiens mRNA for interleukin-15 (cell line NCIH82). |
|---|---|---|
| SEQ ID NO: 966 | g1502342 | H.sapiens mRNA for receptor phosphate PCP-2. |
| SEQ ID NO: 967 | g1502408 | Human CC chemokine receptor 5 mRNA, complete cds. |
| SEQ ID NO: 968 | g1503985 | Human mRNA for KIAA0201 gene, complete cds. |
| SEQ ID NO: 969 | g1504025 | Human mRNA for KIAA0223 gene, partial cds. |
| SEQ ID NO: 970 | g1515434 | Human 1L8-related receptor (DRY6) mRNA, complete cds. |
| SEQ ID NO: 971 | g1517891 | Human tissue inhibitor of metalloproteinases-2 (TIMP-2) gene, exon 5 |
| SEQ ID NO: 972 | g1517900 | Human renal cell carcinoma antigen RAGE-2 mRNA, complete putative |
| SEQ ID NO: 973 | g1518017 | Human TRAF-interacting protein I-TRAF mRNA, complete cds. |
| SEQ ID NO: 974 | g1524068 | H.sapiens mRNA for protein-tyrosine-phosphatase. |
| SEQ ID NO: 975 | g1524091 | H.sapiens mRNA for adenosine triphosphatase, calcium. |
| SEQ ID NO: 976 | g1526425 | Human mRNA for proteasome subunit p42, complete cds |
| SEQ ID NO: 977 | g1549382 | Human Jun activation domain binding protein mRNA, complete cds. |
| SEQ ID NO: 978 | g1552240 | Human mRNA for eotaxin, complete cds. |
| SEQ ID NO: 979 | g1552531 | Human mad protein homolog (hMAD-3) mRNA, complete cds. |
| SEQ ID NO: 980 | g1552845 | H.sapiens mRNA for G-protein coupled receptor. |
| SEQ ID NO: 981 | g1572720 | Human megakaryocyte stimulating factor mRNA, complete cds. |
| SEQ ID NO: 982 | g1575433 | Human glutathione S-transferase P1c (GSTp1c) mRNA, complete cds. |
| SEQ ID NO: 983 | g1592737 | H.sapiens mRNA for transcription factor E2F5. |
| SEQ ID NO: 984 | g1617516 | Human orphan G protein-coupled receptor (RDC1) mRNA, partial cds. |
| SEQ ID NO: 985 | g1619596 | H.sapiens vegf gene, 3'UTR. |
| SEQ ID NO: 986 | g1620019 | Human brain mRNA homologous to 3'UTR of human CD24 gene, partial |
| SEQ ID NO: 987 | g1628406 | H.sapiens mRNA for TCR alpha (TRCAV). |
| SEQ ID NO: 988 | g1628410 | H.sapiens mRNA for TCR beta (TRCBV). |
| SEQ ID NO: 989 | g1657311 | H.sapiens mRNA for FAA protein. |
| SEQ ID NO: 990 | g1658074 | Aequorea victoria green fluorescent protein mutant 3 (GFP) gene, complete cds. |
| SEQ ID NO: 991 | g1666422 | H.sapiens mRNA for receptor protein tyrosine phosphatase. |
| SEQ ID NO: 992 | g1668735 | H.sapiens G protein-coupled receptor CKR-L1. |
| SEQ ID NO: 993 | g1668737 | H.sapiens G protein-coupled receptor CKR-L3. |
| SEQ ID NO: 994 | g1684902 | Human Cdc6-related protein (HsCDC6) mRNA, complete cds. |
| SEQ ID NO: 995 | g177181 | Human cytochrome P4502C18 (CYP2C18) mRNA, clone 6b. |
| SEQ ID NO: 996 | g177204 | Human type IV collagenase mRNA, complete cds. |
| SEQ ID NO: 997 | g1772663 | Human tumor susceptiblity protein (TSG101) mRNA, complete cds. |
| SEQ ID NO: 998 | g1773292 | Human tissue inhibitor of metalloproteinase 4 mRNA, complete cds. ˆKˆK |
| SEQ ID NO: 999 | g178017 | Human activation (Act-2) mRNA, complete cds. |
| SEQ ID NO: 1000 | g178083 | Homo sapiens adenylyl cyclase-associated protein (CAP) mRNA, complete |
| SEQ ID NO: 1001 | g178245 | A (EC 3.2.1-22) |
| SEQ ID NO: 1002 | g178251 | Human epidermal growth factor receptor-related gene, 5' end. |
| SEQ ID NO: 1003 | g178285 | Human angiotensin I-converting enzyme mRNA, complete cds. |
| SEQ ID NO: 1004 | g178325 | Human protein-serine/threonine (AKT2) mRNA, complete cds. |
| SEQ ID NO: 1005 | g178401 | Human aldehyde dehydrogenase type III (ALDHIII) mRNA, complete cds. |
| SEQ ID NO: 1006 | g178535 | Human aminopeptidase N/CD13 mRNA encoding aminopeptidase N, complete |
| SEQ ID NO: 1007 | g178850 | Human apolipoprotein E (epsilon 2 and 3 alleles) mRNA |
| SEQ ID NO: 1008 | g178860 | peptide mRNA. |
| SEQ ID NO: 1009 | g178994 | Human liver arginase mRNA, complete cds. |
| SEQ ID NO: 1010 | g179035 | reductase (EC 1.1.1.2) |
| SEQ ID NO: 1011 | g179094 | Human acid sphingomyelinase (ASM) mRNA, complete cds. |
| SEQ ID NO: 1012 | g179133 | Human T-cell surface antigen CD2 (T11) mRNA, complete cds. |
| SEQ ID NO: 1013 | g179143 | Human T4 surface glycoprotein CD4 gene, complete cds. |
| SEQ ID NO: 1014 | g179145 | Homo sapiens T-cell surface protein T8 mRNA. |

TABLE 1-continued

| SEQ ID NO: 1015 | g179370 | Human bcl-2 mRNA. |
| SEQ ID NO: 1016 | g179410 | Human transglutaminase mRNA, 3' untranslated region. |
| SEQ ID NO:.1017 | g179528 | Human bactericidal permeability increasing protein (BPI) mRNA, |
| SEQ ID NO: 1018 | g179699 | Human C5a anaphylatoxin receptor mRNA, complete cds. |
| SEQ ID NO: 1019 | g179833 | Human common acute lymphoblastic leukemia antigen (CALLA) mRNA, |
| SEQ ID NO: 1020 | g179933 | Human mast cell carboxypeptidase A mRNA, complete cds. |
| SEQ ID NO: 1021 | g179984 | Human C-C chemokine receptor type 1 (C-C CKR-1) mRNA, complete cds. |
| SEQ ID NO: 1022 | g179999 | Human D-type cyclin (CCND2) mRNA, complete cds. |
| SEQ ID NO: 1023 | g180002 | Human D3-type cyclin (CCND3) mRNA, complete cds. |
| SEQ ID NO: 1024 | g180020 | Human monocyte antigen CD14 (CD14) mRNA, complete cds. |
| SEQ ID NO: 1025 | g180035 | Human thymocyte antigen CD1a mRNA, complete cds. |
| SEQ ID NO: 1026 | g180082 | Human dipeptidyl peptidase IV (CD26) mRNA, complete cds. |
| SEQ ID NO: 1027 | g180084 | *Homo sapiens* T cell activation antigen (CD27) mRNA, complete cds. |
| SEQ ID NO: 1028 | g180095 | *H.sapiens* lymphocyte activation antigen CD30 mRNA, complete cds. |
| SEQ ID NO: 1029 | g180097 | Human differentiation antigen (CD33) mRNA, complete cds. |
| SEQ ID NO: 1030 | g180108 | Human CD34 mRNA, complete cds. |
| SEQ ID NO: 1031 | g180116 | Human antigen CD36 mRNA, complete cds |
| SEQ ID NO: 1032 | g180138 | Human pan-leukocyte antigen (CD48) mRNA, complete cds. |
| SEQ ID NO: 1033 | g180140 | Human cell surface antigen (CD53) mRNA, complete cds. |
| SEQ ID NO: 1034 | g18015 | Human lymphocytic antigen CD59/MEM43 mRNA, complete cds. |
| SEQ ID NO: 1035 | g180154 | Human lysosomal membrane glycoprotein CD63 mRNA. |
| SEQ ID NO: 1036 | g180175 | Human cdc25Hs mRNA, complete cds. |
| SEQ ID NO: 1037 | g180177 | Human cdc2-related protein kinase mRNA, complete cds. |
| SEQ ID NO: 1038 | g180495 | *Homo sapiens* lymphocyte chemoattractant factor mRNA, complete cds. |
| SEQ ID NO: 1039 | g180539 | Human heart chymase mRNA, complete cds. |
| SEQ ID NO: 1040 | g180617 | *Homo sapiens* collagenase mRNA, complete cds. |
| SEQ ID NO: 1041 | g180623 | Human cytotoxic lymphocyte maturation factor 35 kDa subunit mRNA, SEQ ID NO: 1041 g180623 |
| SEQ ID NO: 1042 | g180655 | Human c-myb mRNA, 3' end. |
| SEQ ID NO: 1043 | g180710 | Human ciliary neurotrophic factor receptor (CNTFR) mRNA, complete cds. |
| SEQ ID NO: 1044 | g180923 | Human connective tissue growth factor, complete cds. |
| SEQ ID NO: 1045 | g180968 | Human lung cytochrome P450 (IV subfamily) BI protein, complete cds. |
| SEQ ID NO: 1046 | g181181 | Human cathepsin G mRNA, complete cds. |
| SEQ ID NO: 1047 | g181212 | Human aromatase system cytochrome P-450 (P450XIX) mRNA, complete cds. |
| SEQ ID NO: 1048 | g181243 | Human cyclin B mRNA, 3' end. |
| SEQ ID NO: 1049 | g181248 | Human cyclin E mRNA sequence. |
| SEQ ID NO: 1050 | g181253 | *Homo sapiens* cyclooxygenase-2 (Cox-2) mRNA, complete cds. |
| SEQ ID NO: 1051 | g181271 | Human cyclin protein gene, complete cds. |
| SEQ ID NO: 1052 | g181275 | Human cytochrome P-1-450 (TCDD-inducible) mRNA, complete cds. |
| SEQ ID NO: 1053 | g181293 | Human cytochrome P450-IIB (hIIB3) mRNA, complete cds. |
| SEQ ID NO: 1054 | g181297 | Human cytochrome P4502C17 (CYP2C17) mRNA, clone 254c. |
| SEQ ID NO: 1055 | g181299 | Human cytochrome P4502C18 (CYP2C18) mRNA, clone 29c. |
| SEQ ID NO: 1056 | g181301 | Human cytochrome P4502C9 (CYP2C9) mRNA, clone 25. |
| SEQ ID NO: 1057 | g181302 | Human cytochrome P4502C9 (CYP2C9) mRNA, clone 65. |
| SEQ ID NO: 1058 | g181341 | Human cytochrome P450c17 (steroid 17-alpha-hydroxylase/17,20 lyase) |
| SEQ ID NO: 1059 | g181343 | Human cytochrome P4502C19 (CYP2C19) mRNA, clone 11a. |
| SEQ ID NO: 1060 | g181345 | Human cytochrome P450 PCN3 gene, complete cds. |
| SEQ ID NO: 1061 | g181357 | Human cytochrome P450IIF1 protein (CYP2F) mRNA, complete cds. |

TABLE 1-continued

| SEQ ID NO: | ID | Description |
|---|---|---|
| SEQ ID NO: 1062 | g181373 | Human P450 mRNA encoding nifedipine oxidase, complete cds. |
| SEQ ID NO: 1063 | g181375 | Human cholesterol side-chain cleavage enzyme P450scc mRNA, complete |
| SEQ ID NO: 1064 | g181464 | Human decay-accelerating factor mRNA, complete cds. |
| SEQ ID NO: 1065 | g181905 | Human e12 protein (E2A) mRNA, complete cds. |
| SEQ ID NO: 1066 | g181939 | Human CR2/CD21/C3d/Epstein-Barr virus receptor mRNA, complete cds. |
| SEQ ID NO: 1067 | g181954 | Human eosinophyl-derived neurotoxin mRNA, complete cds. |
| SEQ ID NO: 1068 | g181966 | Human elongation factor 1-alpha (EF1A) mRNA, partial cds. |
| SEQ ID NO: 1069 | g181986 | Human early growth response 2 protein (EGR2) mRNA, complete cds. |
| SEQ ID NO: 1070 | g182068 | Human ELAM-1 ligand fucosyltransferase (ELFT) mRNA, complete cds. |
| SEQ ID NO: 1071 | g182131 | Homo sapiens galectin-7 mRNA, complete cds. |
| SEQ ID NO: 1072 | g182262 | Human transcription factor ETR103 mRNA, complete cds. |
| SEQ ID NO: 1073 | g182282 | Human EVI2B3P gene, exon and complete cds. |
| SEQ ID NO: 1074 | g182409 | Human Fas antigen (fas) mRNA, complete cds. |
| SEQ ID NO: 1075 | g182447 | Human Fc-epsilon receptor (IgE receptor) mRNA, complete cds (H107 |
| SEQ ID NO: 1076 | g182473 | Human IgG low affinity Fc fragment receptor (FcRIIa) mRNA, complete |
| SEQ ID NO: 1077 | g182482 | Human fibroblast collagenase inhibitor mRNA, complete cds. |
| SEQ ID NO: 1078 | g182513 | Human ferritin L chain mRNA, complete cds. |
| SEQ ID NO: 1079 | g182525 | precursor (insulin-like growth factor). |
| SEQ ID NO: 1080 | g182573 | Human fgr proto-oncogene encoded p55-c-fgr protein, complete cds. |
| SEQ ID NO: 1081 | g182625 | Human rapamycin binding protein (FK506) mRNA, complete cds. |
| SEQ ID NO: 1082 | g182739 | gene, complete cds and Alu repeats. |
| SEQ ID NO: 1083 | g182741 | Human formyl peptide receptor-like receptor (FPRL1) mRNA, complete |
| SEQ ID NO: 1084 | g182860 | Human glyceraldehyde-3-phosphate dehydrogenase mRNA, complete cds. |
| SEQ ID NO: 1085 | g182939 | Human growth arrest and DNA-damage-inducible protein (gadd45) mRNA, |
| SEQ ID NO: 1086 | g183046 | Human granulocyte colony-stimulating factor receptor (G-CSFR-1) mRNA, |
| SEQ ID NO: 1087 | g183083 | Human basic fibroblast growth factor (bFGF) 22.5 kd, 21 kd and 18 kd |
| SEQ ID NO: 1088 | g183260 | peroxidase (EC 1.11.1.9.). |
| SEQ ID NO: 1089 | g183361 | Human GM-CSF receptor mRNA, complete cds. |
| SEQ ID NO: 1090 | g183390 | Human granule membrane protein-140 mRNA, complete cds. |
| SEQ ID NO: 1091 | g183416 | Human guanine nucleotide-binding protein G-s, alpha subunit mRNA, |
| SEQ ID NO: 1092 | g183442 | H.sapiens zinc finger transcriptionai regulator mRNA, complete cds. |
| SEQ ID NO: 1093 | g183452 | Human endothelial membrane glycoprotein IIIa (GPIIIa) mRNA, complete |
| SEQ ID NO: 1094 | g183484 | Human Epstein-Barr virus induced G-protein coupled receptor mRNA, |
| SEQ ID NO: 1095 | g183497 | cds, and platelet glycoprotein Ib beta chain |
| SEQ ID NO: 1096 | g183499 | Human platelet glycoprotein Ib alpha chain mRNA, complete cds. |
| SEQ ID NO: 1097 | g183503 | Human platelet glycoprotein IIb mRNA, 3' end. |
| SEQ ID NO: 1098 | g183612 | H.sapiens granulin mRNA, complete cds. |
| SEQ ID NO: 1099 | g183628 | Human cytokine (GRO-beta) mRNA, complete cds. |
| SEQ ID NO: 1100 | g183632 | Human cytokine (GRO-gamma) mRNA, complete cds. |
| SEQ ID NO: 1101 | g183655 | Human glutathione S-transferase mRNA, complete cds. |
| SEQ ID NO: 1102 | g183661 | Homo sapiens glutathione transferase (GST) mRNA, with an 82 bp |
| SEQ ID NO: 1103 | g183666 | Human glutathione S-transferase Ha subunit 2 (GST) mRNA, complete cds. |
| SEQ ID NO: 1104 | g183684 | Human glucose transporter-like protein-III (GLUT3), complete cds. |
| SEQ ID NO: 1105 | g183911 | Human hemopoietic cell protein-tyrosine kinase (HCK) gene, complete |
| SEQ ID NO: 1106 | g183915 | Human hematopoietic cell phosphatase mRNA, complete cds. |
| SEQ ID NO: 1107 | g183944 | Human sickle beta-hemoglobin mRNA. |
| SEQ ID NO: 1108 | g184081 | Human histone H2A.1 (H2A) gene, complete cds. |

TABLE 1-continued

| SEQ ID NO: | ID | Description |
|---|---|---|
| SEQ ID NO: 1109 | g184227 | Human 14 kDa beta-galactoside-binding lectin (114) gene, complete cds. |
| SEQ ID NO: 1110 | g184262 | Human (clones 18, 23, 27, 24) c-myeloproliferative leukemia virus type |
| SEQ ID NO: 1111 | g184402 | shock transcription factor 4, complete cds. |
| SEQ ID NO: 1112 | g184413 | Human 70 kDa heat shock protein (hsp70) gene segment. |
| SEQ ID NO: 1113 | g184508 | Human interleukin 9 receptor mRNA, complete cds. |
| SEQ ID NO: 1114 | g184524 | Human integrin beta-5 subunit mRNA, complete cds |
| SEQ ID NO: 1115 | g184532 | Human major group rhinovirus receptor (HRV) mRNA, complete cds. |
| SEQ ID NO: 1116 | g184622 | Human interferon-beta mRNA, complete cds. |
| SEQ ID NO: 1117 | g184636 | (IFN-alpha-F) mRNA, complete cds. |
| SEQ ID NO: 1118 | g184645 | Human interferon-alpha receptor (HuIFN-alpha-Rec) mRNA, complete cds. |
| SEQ ID NO: 1119 | g184650 | Human interferon-gamma receptor mRNA, complete cds |
| SEQ ID NO: 1120 | g185361 | Human (hybridoma H210) anti-hepatitis A IgG variable region, constant |
| SEQ ID NO: 1121 | g186264 | Human gamma-interferon-inducible protein (IP-30) mRNA, complete cds. |
| SEQ ID NO: 1122 | g186270_2 | mRNA, complete cds. |
| SEQ ID NO: 1123 | g186270_1 | complete cds. |
| SEQ ID NO: 1124 | g186279 | *Homo sapiens* interleukin 1 alpha (IL 1) mRNA, complete cds. |
| SEQ ID NO: 1125 | g186289 | Human interleukin 1 receptor mRNA, complete cds. |
| SEQ ID NO: 1126 | g186322 | Human interleukin 2 receptor beta chain (p70–75) mRNA, complete cds. |
| SEQ ID NO: 1127 | g186326 | Human interleukin 3 (IL-3) mRNA, complete cds. |
| SEQ ID NO: 1128 | g186330 | Human interleukin 3 receptor (hIL-3Ra) mRNA, complete cds. |
| SEQ ID NO: 1129 | g186334 | Human interleukin 4 (IL-4) mRNA, complete cds. |
| SEQ ID NO: 1130 | g186346 | (IL-6) receptor. |
| SEQ ID NO: 1131 | g186353 | Human membrane glycoprotein gp130 mRNA, complete cds. |
| SEQ ID NO: 1132 | g186363 | Human interleukin 7 (IL-7) mRNA, complete cds. |
| SEQ ID NO: 1133 | g186365 | Human interleukin-7 receptor (IL-7) mRNA, complete cds. |
| SEQ ID NO: 1134 | g186369 | Human IL-8 receptor mRNA, complete cds. |
| SEQ ID NO: 1135 | g186377 | Human interleuken 8 receptor B mRNA, complete cds. |
| SEQ ID NO: 1136 | g186379 | Human interleukin enhancer binding factor 2 (ILF2) mRNA. |
| SEQ ID NO: 1137 | g186439 | Human insulin receptor mRNA, complete cds. |
| SEQ ID NO: 1138 | g186496 | Human integrin alpha-3 chain mRNA, complete cds. |
| SEQ ID NO: 1139 | g186508 | Human integrin beta-7 subunit mRNA, complete cds. |
| SEQ ID NO: 1140 | g186516 | Human interleukin-8 receptor type B (IL8RB) mRNA, complete cds. |
| SEQ ID NO: 1141 | g186566 | *Homo sapiens* interferon alpha induced transcriptional activator |
| SEQ ID NO: 1142 | g186567 | Human transcription factor ISGF-3 mRNA sequence. |
| SEQ ID NO: 1143 | g186624 | Human c-jun proto oncogene (JUN), complete cds, clone hCJ-1. |
| SEQ ID NO: 1144 | g186626 | (JunB) gene, 5' region and complete |
| SEQ ID NO: 1145 | g186763 | mRNA, complete cds. |
| SEQ ID NO: 1146 | g186933 | Human leukocyte adhesion protein (LFA-1/Mac-1/p150, 95 family) beta |
| SEQ ID NO: 1147 | g186935 | Human CD11b (MAC-1/Mol/CR3) leukocyte adhesion receptor alpha subunit |
| SEQ ID NO: 1148 | g186965 | Human lipopolysaccharide binding protein (LBP) mRNA, complete cds. |
| SEQ ID NO: 1149 | g186967 | Human lipocortin-III mRNA, complete cds. |
| SEQ ID NO: 1150 | g187116 | (leukocyte (neutrophil) elastase. |
| SEQ ID NO: 1151 | g187118 | Human leukosialin mRNA, complete cds. |
| SEQ ID NO: 1152 | g187137 | |
| SEQ ID NO: 1153 | g187172 | Human leukotriene A-4 hydrolase mRNA, complete cds. |
| SEQ ID NO: 1154 | g187182 | Human lymph node homing receptor mRNA, complete cds. |
| SEQ ID NO: 1155 | g187192 | Human lipoxygenase mRNA, complete cds. |
| SEQ ID NO: 1156 | g187239 | Human leukocyte surface protein (CD31) mRNA, complete cds. |
| SEQ ID NO: 1157 | g187262 | Human B cell differentiation antigen mRNA, complete cds. |
| SEQ ID NO: 1158 | g187268 | Human lyn mRNA encoding a tyrosine kinase. |
| SEQ ID NO: 1159 | g187273 | Human eosinophil Charcot-Leyden crystal (CLC) protein |

TABLE 1-continued

| | | |
|---|---|---|
| SEQ ID NO: 1160 | g187288 | *Homo sapiens* antagonizer of myc transcriptional activity (Mad) mRNA, |
| SEQ ID NO: 1161 | g187290 | *Homo sapiens* MAD-3 mRNA encoding IkB-like activity, complete cds. |
| SEQ ID NO: 1162 | g187386 | Human myristoylated alanine-rich C-kinase substrate mRNA, complete |
| SEQ ID NO: 1163 | g187390 | Human helix-loop-helix zipper protein (max) mRNA, complete cds. |
| SEQ ID NO: 1164 | g187414 | Human eosinophil granule major basic protein mRNA, complete cds. |
| SEQ ID NO: 1165 | g187434 | Human monocyte chemotactic and activating factor (MCAF) mRNA, complete |
| SEQ ID NO: 1166 | g187455 | *Homo sapiens* macrophage capping protein mRNA, complete cds. |
| SEQ ID NO: 1167 | g187468 | Human P-glycoprotein (MDR1) mRNA, complete cds. |
| SEQ ID NO: 1168 | g187501 | Human membrane glycoprotein P (mdr3) mRNA, complete cds. |
| SEQ ID NO: 1169 | g187701 | Human MHC protein homologous to chicken B complex protein mRNA, |
| SEQ ID NO: 1170 | g188255 | mRNA, complete cds. |
| SEQ ID NO: 1171 | g188469 | Human major histocompatibility class II antigen gamma chain mRNA, |
| SEQ ID NO: 1172 | g188555 | Human migration inhibitory factor (MIF) mRNA, complete cds. |
| SEQ ID NO: 1173 | g188568 | *Homo sapiens* MAP kinase kinase mRNA, complete cds. |
| SEQ ID NO: 1174 | g188618 | Human matrix metalloproteinase-3 (MMP-3) mRNA, complete cds. |
| SEQ ID NO: 1175 | g188623 | Human monocyte activation antigen (Mo3) mRNA, complete cds. |
| SEQ ID NO: 1176 | g189050 | Human 47-kD autosomal chronic granulomatous disease protein mRNA, |
| SEQ ID NO: 1177 | g189066 | *H.sapiens* NAP (nucleosome assembly protein) mRNA, complete cds. |
| SEQ ID NO: 1178 | g189068 | Human neutrophil adherence receptor alpha-M subunit mRNA. |
| SEQ ID NO: 1179 | g189105 | Human neutrophil cytochrome b light chain p22 phagocyte b-cytochrome |
| SEQ ID NO: 1180 | g189177 | Human nuclear factor kappa-B DNA binding subunit (NF-kappa-B) mRNA, |
| SEQ ID NO: 1181 | g189237 | Human neuroleukin mRNA, complete cds. |
| SEQ ID NO: 1182 | g189243 | Human N-myc oncogene protein mRNA. |
| SEQ ID NO: 1183 | g189267 | Human neutrophil oxidase factor (p67-phox) mRNA, complete cds. |
| SEQ ID NO: 1184 | g189368 | Human ornithine decarboxylase (ODC1) mRNA, complete cds. |
| SEQ ID NO: 1185 | g189501 | Human 65-kilodalton phosphoprotein (p65) mRNA, complete cds. |
| SEQ ID NO: 1186 | g189537 | Human platelet activating factor receptor mRNA, complete cds. |
| SEQ ID NO: 1187 | g189541 | Human plasminogen activator inhibitor-1 (PAI-1) mRNA, complete cds. |
| SEQ ID NO: 1188 | g189544 | Human placental plasminogen activator inhibitor mRNA, complete cds. |
| SEQ ID NO: 1189 | g189546 | Human plasminogen activator inhibitor mRNA, complete cds. |
| SEQ ID NO: 1190 | g189616 | Human protein PP4-X mRNA, complete cds. |
| SEQ ID NO: 1191 | g189679 | Human protein kinase C-delta 13 mRNA, complete cds. |
| SEQ ID NO: 1192 | g189700 | Human platelet-derived endothelial cell growth factor mRNA, complete |
| SEQ ID NO: 1193 | g189731 | Human platelet-derived growth factor (PDGF) receptor mRNA, complete |
| SEQ ID NO: 1194 | g189733 | Human platelet-derived growth factor receptor alpha (PDGFRA) mRNA, |
| SEQ ID NO: 1195 | g189846 | Human perforin mRNA, complete cds. |
| SEQ ID NO: 1196 | g189940 | Human phosphorylase kinase (PSK-C3) mRNA, complete cds. |
| SEQ ID NO: 1197 | g189946 | Human homeobox protein (PHOX1) mRNA, 3' end. |
| SEQ ID NO: 1198 | g189995 | Human pyruvate kinase type L mRNA, complete cds. |
| SEQ ID NO: 1199 | g190003 | Human phosphatidylcholine 2-acylhydrolase (cPLA2) mRNA, complete cds. |
| SEQ ID NO: 1200 | g190012 | Human lung phospholipase A-2 (PLA-2) mRNA, complete cds, clone |
| SEQ ID NO: 1201 | g190035 | C. |
| SEQ ID NO: 1202 | g190039 | *Homo sapiens* phospholipase C-beta-2 mRNA, complete cds. |
| SEQ ID NO: 1203 | g190339 | Human perforin (PRF1) gene, complete cds. |

TABLE 1-continued

| SEQ ID NO: | ID | Description |
|---|---|---|
| SEQ ID NO: 1204 | g190419 | Human secretory granule proteoglycan peptide core mRNA, complete cds. |
| SEQ ID NO: 1205 | g190734 | Human protein-tyrosine kinase (JAK1) mRNA, complete cds. |
| SEQ ID NO: 1206 | g190827 | Human rac protein kinase alpha mRNA, complete cds. |
| SEQ ID NO: 1207 | g190888 | Human RASF-A PLA2 mRNA, complete cds. |
| SEQ ID NO: 1208 | g190899 | Human (T3M-4) cellular transforming oncogene c-Ki-ras, exon 2. |
| SEQ ID NO: 1209 | g219534 | Human CGM1a mRNA for CD66d. |
| SEQ ID NO: 1210 | g219587 | Human mRNA for DnaJ protein homolog, complete cds. |
| SEQ ID NO: 1211 | g219667 | Human plasma (extracellular) mRNA for glutathione peroxidase, complete |
| SEQ ID NO: 1212 | g219866 | Human mRNA for HM74. |
| SEQ ID NO: 1213 | g219868 | Human mRNA for HM89. |
| SEQ ID NO: 1214 | g219924 | Human mRNA for MGC-24, complete cds. |
| SEQ ID NO: 1215 | g219928 | Human midkine gene, complete cds. |
| SEQ ID NO: 1216 | g219935 | Human CGM6 mRNA for CD66b (NCA-95). |
| SEQ ID NO: 1217 | g220138 | Human Pro-urokinase gene, complete cds. |
| SEQ ID NO: 1218 | g232582 | HOX11 = HOX11 homeodomain {homeobox} [human, mRNA, 1988 nt] |
| SEQ ID NO: 1219 | g235648 | tumor necrosis factor receptor = 75-kda [human, mRNA, 3492 nt] |
| SEQ ID NO: 1220 | g23896 | Human placental cDNA coding for 5'nucleotidase (EC 3.1.3.5). |
| SEQ ID NO: 1221 | g243493 | protein kinase inhibitor [human, neuroblastoma cell line SH-SY-5Y, |
| SEQ ID NO: 1222 | g243543 | BPTP-1 = protein-tyrosine phosphatase [human, pre-B cell NALM-6, mRNA, |
| SEQ ID NO: 1223 | g243865 | Ig gamma = immunoglobulin heavy chain [rats, humanized lympholytic MoAb |
| SEQ ID NO: 1224 | g243887 | ubiquitin carboxyl extension protein [human, mRNA, 540 nt]. |
| SEQ ID NO: 1225 | g246741 | CD8 beta 1 = T cell surface glycoprotein CD8 beta 1 chain {alternatively |
| SEQ ID NO: 1226 | g247306 | cytochrome P450 reductase [human, placenta, mRNA Partial, 2403 nt]. |
| SEQ ID NO: 1227 | g250802 | cathepsin S = cysteine proteinase [human, testis, mRNA, 1784 nt]. |
| SEQ ID NO: 1228 | g252001 | GADD153 = growth arrest and DNA-damage-inducible gene [human |
| SEQ ID NO: 1229 | g258761 | AMPD2 = AMP deaminase isoform L [human, T-lymphoblast and placenta, |
| SEQ ID NO: 1230 | g260573 | transcription factor E2F like protein [human, mRNA, 2492 nt]. |
| SEQ ID NO: 1231 | g265702 | A1-A2 lambda hybrid GAU heavy chain {membrane exon} [human, myeloma, mRNA Partial, 360 nt]. ACCESSION S55736 |
| SEQ ID NO: 1232 | g28343 | H.sapiens ACTH-R gene for adrenocorticotropic hormone receptor. |
| SEQ ID NO: 1233 | g28711 | H.sapiens encoding skin-derived antileukoproteinase. |
| SEQ ID NO: 1234 | g28805 | Human mRNA for lipoprotein apoCII. |
| SEQ ID NO: 1235 | g28820 | Human mRNA for A-raf-1 oncogene. |
| SEQ ID NO: 1236 | g288309 | NO: 1236 g288309 H.sapiens mRNA for B cell differentiation factor I. |
| SEQ ID NO: 1237 | g28850 | H.sapiens mRNA for arrestin (partial) |
| SEQ ID NO: 1238 | g28875 | H.sapiens ash mRNA. |
| SEQ ID NO: 1239 | g28976 | Human mRNA for azurocidin. |
| SEQ ID NO: 1240 | g291863 | Human ADP-ribosylation factor-like mRNA (ARL2). |
| SEQ ID NO: 1241 | g291897 | Homo sapiens early activation antigen CD69 mRNA, complete cds. |
| SEQ ID NO: 1242 | g291928 | Homo sapiens Ig superfamily CTLA-4 mRNA, complete cds. |
| SEQ ID NO: 1243 | g292054 | Human helix-loop-helix basic phosphoprotein (G058) mRNA, complete cds. |
| SEQ ID NO: 1244 | g292159 | Human heat shock protein 70 (hsp70) mRNA, complete cds. |
| SEQ ID NO: 1245 | g292276 | Homo sapiens lymphotoxin-beta mRNA, complete cds. |
| SEQ ID NO: 1246 | g292414 | Homo sapiens zeta-crystallin/quinone reductase mRNA, complete cds. |
| SEQ ID NO: 1247 | g292416 | Homo sapiens macrophage inflammatory protein-1-alpha/RANTES receptor |
| SEQ ID NO: 1248 | g292509 | Human squalene synthetase (ERG9) mRNA, complete cds. |
| SEQ ID NO: 1249 | g29370 | Human gene for beta-adrenergic receptor (beta-2 subtype) |

TABLE 1-continued

| SEQ ID NO: | ID | Description |
|---|---|---|
| SEQ ID NO: 1250 | g29388 | *H.sapiens* mRNA for B-cell antigen CD75. |
| SEQ ID NO: 1251 | g29471 | Human mRNA for B-myb gene. |
| SEQ ID NO: 1252 | g29537 | Human mRNA for C1q B-chain of complement system. |
| SEQ ID NO: 1253 | g29645 | *H.sapiens* mRNA for CAMPATH-1 (CDw52) antigen. |
| SEQ ID NO: 1254 | g29744 | Human mRNA for Fc gamma receptor (FcRIII, CD16, FcR-1o). |
| SEQ ID NO: 1255 | g29773 | Human mRNA for B lymphocyte antigen CD20 (B1, Bp35). |
| SEQ ID NO: 1256 | g29778 | *H.sapiens* CD22 mRNA. |
| SEQ ID NO: 1257 | g297787 | NO: 1257 g297787 *H.sapiens* interleukin-13 mRNA. |
| SEQ ID NO: 1258 | g29793 | Human mRNA for leukocyte antigen CD37. |
| SEQ ID NO: 1259 | g29817 | *H.sapiens* CD6 mRNA for T cell glycoprotein CD6. |
| SEQ ID NO: 1260 | g29819 | Human mRNA for CD7 antigen (gp40). |
| SEQ ID NO: 1261 | g298303 | interleukin-6 [human, tonsillar mononuclear cells, mRNA, 657 nt]. |
| SEQ ID NO: 1262 | g29850 | Human CDw40 mRNA for nerve growth factor receptor-related B-lymphocyte |
| SEQ ID NO: 1263 | g298664 | CD68 = 110 kda transmembrane glycoprotein [human, promonocyte cell line |
| SEQ ID NO: 1264 | g30125 | *H.sapiens* mRNA for type I interstitial collagenase. |
| SEQ ID NO: 1265 | g30185 | Human mRNA for complement receptor type 1 (CR1, C3b/C4b receptor, |
| SEQ ID NO: 1266 | g30220 | Human mRNA for cripto protein. |
| SEQ ID NO: 1267 | g30255 | Human mRNA for C-SRC-kinase. |
| SEQ ID NO: 1268 | g30306 | Human mRNA for cyclin A. |
| SEQ ID NO: 1269 | g30308 | Human mRNA-for T-cell cyclophilin. |
| SEQ ID NO: 1270 | g303602 | Human mRNA for cytochrome P-450LTBV. |
| SEQ ID NO: 1270 | g303602 | Human mRNA for cytochrome P-450LTBV. |
| SEQ ID NO: 1271 | g303611 | Human mRNA for interleukin 2 receptor gamma chain. |
| SEQ ID NO: 1272 | g306474 | *Homo sapiens* tyrosine protein kinase (CAK) gene, complete cds. |
| SEQ ID NO: 1273 | g307184 | Homosapiens ERK activator kinase (MEK2) mRNA. |
| SEQ ID NO: 1274 | g307299 | Human NF-kappa-B transcription factor p65 subunit mRNA, complete cds. |
| SEQ ID NO: 1275 | g307387 | Human ribosomal protein L7 (RPL7) mRNA, complete cds. |
| SEQ ID NO: 1276 | g307390 | Human ribosomal protein S13 (RPS13) mRNA, complete cds. |
| SEQ ID NO: 1277 | g30820 | *H.sapiens* mRNA for IFN-inducible gamma2 protein. |
| SEQ ID NO: 1278 | g31097 | Human mRNA for elongation factor 1 alpha subunit (EF-1 alpha) |
| SEQ ID NO: 1279 | g311374 | Human 1-8U gene from interferon-inducible gene family. |
| SEQ ID NO: 1280 | g311375 | *H.sapiens* Humig mRNA. |
| SEQ ID NO: 1281 | g311699 | *H.sapiens* GPx-4 mRNA for phospholipid hydroperoxide glutathione |
| SEQ ID NO: 1282 | g31192 | *H.sapiens* granulin mRNA, complete cds. |
| SEQ ID NO: 1283 | g312141 | *H.sapiens* mRNA for M130 antigen. |
| SEQ ID NO: 1284 | g312145 | *H.sapiens* mRNA for M130 antigen cytoplasmic variant 2. |
| SEQ ID NO: 1285 | g312466 | *H.sapiens* atk mRNA for agammaglobulinaemia tyrosine kinase. |
| SEQ ID NO: 1286 | g31296 | *H.sapiens* FACC mRNA from complementation group C (FA(C)). |
| SEQ ID NO: 1287 | g31323 | Human Fc-gamma RIII-2 cDNA for Fc-gamma receptor III-2 (CD16) |
| SEQ ID NO: 1288 | g31386 | Human mRNA for fibroblast growth receptor 2-Ig domain. |
| SEQ ID NO: 1289 | g31396 | Human mRNA for fibronectin (FN precursor). |
| SEQ ID NO: 1290 | g31421 | Human mRNA for leukocyte-associated molecule-1 alpha subunit (LFA-1 |
| SEQ ID NO: 1291 | g31425 | *H.sapiens* mRNA for five-lipoxygenase activating protein (FLAP). |
| SEQ ID NO: 1292 | g31437 | Human mRNA for fibronectin receptor alpha subunit. |
| SEQ ID NO: 1293 | g31441 | Human mRNA for fibronectin receptor beta subunit. |
| SEQ ID NO: 1294 | g31667 | Human liver mRNA for beta-subunit signal transducing proteins Gs/Gi |
| SEQ ID NO: 1295 | g31880 | *H.sapiens* mRNA for glutathione peroxidase-GI. |
| SEQ ID NO: 1296 | g32054 | Human HS1 gene for heamatopoietic lineage cell specific protein. |
| SEQ ID NO: 1297 | g32432 | Human mRNA for hematopoetic proteoglycan core protein. |
| SEQ ID NO: 1298 | g32449 | Human mRNA encoding IMP:pyrophosphate phosphoribosyltransferase E.C. |

TABLE 1-continued

| | | |
|---|---|---|
| SEQ ID NO: 1299 | g32455 | *H.sapiens* hR-PTPu gene for protein tyrosine phosphatase. |
| SEQ ID NO: 1300 | g32477 | Human mRNA for heat shock protein HSP27. |
| SEQ ID NO: 1301 | g32485 | Human mRNA for heat shock protein hsp86. |
| SEQ ID NO: 1302 | g32691 | Human mRNA for interferon IFN-gamma. |
| SEQ ID NO: 1303 | g32764 | *H. sapiens* Ig constant region gene. |
| SEQ ID NO: 1304 | g32983 | switch region (S epsilon). |
| SEQ ID NO: 1305 | g32998 | Human DNA for insulin-like growth factor II (IGF-2); exon 7 and |
| SEQ ID NO: 1306 | g33058 | Human mRNA for insulin-like growth factor I receptor. |
| SEQ ID NO: 1307 | g33780 | Human mRNA encoding interleukin-2 (IL-2) a lymphozyte regulatory |
| SEQ ID NO: 1308 | g33789 | Human mRNA for interleukin 1 beta. Peripheral blood mononuclear cells. |
| SEQ ID NO: 1309 | g338010 | Human proteolytic serine esterase-like protein (SECT) gene, complete |
| SEQ ID NO: 1310 | g338020 | Human sepiapterin reductase mRNA, complete cds. |
| SEQ ID NO: 1311 | g338079 | Human tyrosine phosphatase mRNA, complete cds. |
| SEQ ID NO: 1312 | g33812 | Human mRNA for interleukin-2 receptor. |
| SEQ ID NO: 1313 | g338227 | Human src-like kinase (slk) mRNA, complete cds. |
| SEQ ID NO: 1314 | g33833 | Human IL-4-R mRNA for the interleukin 4 receptor. |
| SEQ ID NO: 1315 | g33839 | Human HSIL5R2 gene for interleukin-5 receptor type 2. |
| SEQ ID NO: 1316 | g338444 | Human T-cell-specific homodimer surface protein CD28 mRNA, complete |
| SEQ ID NO: 1317 | g338633 | Human syndecan mRNA, complete cds. |
| SEQ ID NO: 1318 | g33906 | Human mRNA for integrin alpha-2 subunit. |
| SEQ ID NO: 1319 | g33910 | Human mRNA for integrin beta(4)subunit. |
| SEQ ID NO: 1320 | g33917 | Human mRNA for gamma-interferon inducible early response gene (with |
| SEQ ID NO: 1321 | g339420 | Human T cell-specific protein (RANTES) mRNA, complete cds. |
| SEQ ID NO: 1322 | g33945 | Human mRNA for integrin alpha-4 subunit. |
| SEQ ID NO: 1323 | g33949 | *H.sapiens* mRNA for integrin, alpha subunit. |
| SEQ ID NO: 1324 | g339515 | Human transferrin receptor mRNA, complete cds. |
| SEQ ID NO: 1325 | g339569 | Human TGF-beta type II receptor mRNA, complete cds. |
| SEQ ID NO: 1326 | g339656 | Human endothelial cell thrombomodulin mRNA, complete cds. |
| SEQ ID NO: 1327 | g339706 | Human metalloproteinase-2 inhibitor (TIMP-2) mRNA, complete cds. |
| SEQ ID NO: 1328 | g339708 | Human thymidine kinase mRNA, complete cds. |
| SEQ ID NO: 1329 | g339737 | Human tumor necrosis factor (TNF) mRNA. |
| SEQ ID NO: 1330 | g339744 | Human tumor necrosis factor receptor mRNA, complete cds. |
| SEQ ID NO: 1331 | g339755 | Human tumor necrosis factor receptor (TNF receptor) mRNA, complete |
| SEQ ID NO: 1332 | g339782 | Human slow skeletal muscle troponin T mRNA, clone M1. |
| SEQ ID NO: 1333 | g340306 | Human cell adhesion protein (vitronectin) receptor alpha subunit mRNA, |
| SEQ ID NO: 1334 | g340396 | complete cds. |
| SEQ ID NO: 1335 | g34084 | Human c-kit proto-oncogene mRNA. |
| SEQ ID NO: 1336 | g34266 | Human mRNA for LCA-homolog. LAR protein (leukocyte antigen related). |
| SEQ ID NO: 1337 | g34275 | Human mRNA for T200 leukocyte common antigen (CD45, LC-A) |
| SEQ ID NO: 1338 | g34280 | Human mRNA for leukocyte common antigen (T200). |
| SEQ ID NO: 1339 | g34288 | Human mRNA for lck tyrosine kinase. |
| SEQ ID NO: 1340 | g34312 | Human mRNA for lactate dehydrogenase-A (LDH-A, EC 1.1.1.27) |
| SEQ ID NO: 1341 | g34346 | Human mRNA for lymphocyte function associated antigen-3 (LFA-3). |
| SEQ ID NO: 1342 | g34387 | Human mRNA for lipocortin. |
| SEQ ID NO: 1343 | g34444 | Human mRNA for lymphotoxin. |
| SEQ ID NO: 1344 | g34513 | mRNA, 739 nt]. |
| SEQ ID NO: 1345 | g34621 | Human mRNA for melanoma growth stimulatory activity (MGSA). |
| SEQ ID NO: 1346 | g34658 | Human mRNA for macrophage inflammatory protein-2alpha (MIP2alpha). |
| SEQ ID NO: 1347 | g34702 | *H.sapiens* mRNA for macrophage mannose receptor. |
| SEQ ID NO: 1348 | g34710 | Human mRNA for Mn superoxide dismutase (EC 1.15.1.1.) |
| SEQ ID NO: 1349 | g34750 | Human 464.2 mRNA for a cytokine effector of inflammatory response. |
| SEQ ID NO: 1350 | g34770 | Human mRNA for calcium-binding protein in macrophages (MRP-14) |

TABLE 1-continued

| | | |
|---|---|---|
| SEQ ID NO: 1351 | g34815 | Human mRNA encoding the c-myc oncogene. |
| SEQ ID NO: 1352 | g348706 | *Homo sapiens* cathepsin B mRNA, 3' UTR with a stem-loop structure |
| SEQ ID NO: 1353 | g348911 | Human glycoprotein mRNA, complete cds. |
| SEQ ID NO: 1354 | g349277 | *Homo sapiens* CD30 ligand mRNA, complete cds. |
| SEQ ID NO: 1355 | g349765 | *Homo sapiens* 3',5'-cyclic AMP phosphodiesterase mRNA, 3'end. |
| SEQ ID NO: 1356 | g35014 | Human melanoma mRNA for nck protein, showing homology to src. |
| SEQ ID NO: 1357 | g35067 | Human mRNA for Nm23 protein, involved in developmental regulation |
| SEQ ID NO: 1358 | g35175 | *H.sapiens* mRNA for leukocyte adhesion glycoprotein p150, 95. |
| SEQ ID NO: 1359 | g35215 | Human mRNA fragment for phosphoprotein p53. |
| SEQ ID NO: 1360 | g35443 | Human mRNA for platelet glycoprotein IX. |
| SEQ ID NO: 1361 | g35492 | Human mRNA for protein kinase C (PKC) type beta II. |
| SEQ ID NO: 1362 | g35500 | *H.sapiens* mRNA for protein kinase C zeta. |
| SEQ ID NO: 1363 | g35567 | Human mRNA for DNA polymerase alpha-subunit. |
| SEQ ID NO: 1364 | g35569 | Human mRNA for polyA binding protein. |
| SEQ ID NO: 1365 | g35631 | Human PRAD1 mRNA for cyclin. |
| SEQ ID NO: 1366 | g35787 | Human HPTP beta mRNA for protein tyrosine phosphatase beta. |
| SEQ ID NO: 1367 | g35795 | Human HPTP zeta mRNA for protein tyrosine phosphatase zeta. |
| SEQ ID NO: 1368 | g35798 | Human pump-1 mRNA homolog. to metalloproteinase, collagenase and |
| SEQ ID NO: 1369 | g36064 | Human mRNA for M1 subunit of ribonucleotide reductase. |
| SEQ ID NO: 1370 | g36154 | cds. |
| SEQ ID NO: 1371 | g36326 | *H.sapiens* mRNA for S-adenosylmethionine synthetase. |
| SEQ ID NO: 1372 | g36560 | Human mRNA for spi-1 proto-oncogene. |
| SEQ ID NO: 1373 | g36612 | *H.sapiens* mRNA cdk3 for serine/threonine protein kinase. |
| SEQ ID NO: 1374 | g36632 | Human mRNA for stromelysin. |
| SEQ ID NO: 1375 | g37039 | Human mRNA for T3 epsilon chain (20K) of T-cell receptor (from |
| SEQ ID NO: 1376 | g37092 | Human mRNA for transforming growth factor-beta (TGF-beta). |
| SEQ ID NO: 1377 | g37408 | *H.sapiens* mRNA for tetranectin. |
| SEQ ID NO: 1378 | g37503 | Human tyk2 mRNA for non-receptor protein tyrosine kinase. |
| SEQ ID NO: 1379 | g37983 | Human mRNA of X-CGD gene involved in chronic granulomatous disease |
| SEQ ID NO: 1380 | g38271 | Human cytochrome P450 (IIB subfamily) mRNA fragment. |
| SEQ ID NO: 1381 | g38273 | Human cytochrome P450 (IIA subfamily) mRNA fragment. |
| SEQ ID NO: 1382 | g38329 | *H.sapiens* (clone pBS NKI) CD3-zeta mRNA. |
| SEQ ID NO: 1383 | g38405_1 | chain constant region (mAb61) |
| SEQ ID NO: 1384 | g38405_2 | heavy chain constant region (mAb61) |
| SEQ ID NO: 1385 | g385858 | P-450LTBV |
| SEQ ID NO: 1386 | g386256 | insulin receptor substrate-1 [human, skeletal muscle, mRNA, 5828 nt]. |
| SEQ ID NO: 1387 | g388165 | Human Bax alpha mRNA, complete cds. |
| SEQ ID NO: 1388 | g388167 | Human Bax beta mRNA, complete cds. |
| SEQ ID NO: 1389 | g392887 | Human SRC-like tyrosine kinase (FRK) mRNA, complete cds. |
| SEQ ID NO: 1390 | g396163 | factor (ECGF-beta) mRNA, complete |
| SEQ ID NO: 1391 | g397938 | *H.sapiens* CD69 gene. |
| SEQ ID NO: 1392 | g398028 | *Homo sapiens* Huntington disease-associated protein (HD) mRNA, complete |
| SEQ ID NO: 1393 | g400362 | *Homo sapiens* NF-E2 protein (NF-E2) mRNA, complete cds. |
| SEQ ID NO: 1394 | g402196 | *H.sapiens* ALK-1 mRNA. |
| SEQ ID NO: 1395 | g402646 | *H.sapiens* mRNA for fast MyBP-C. |
| SEQ ID NO: 1396 | g404012 | Human pre-B cell enhancing factor (PBEF) mRNA, complete cds. |
| SEQ ID NO: 1397 | g407074 | *H.sapiens* mRNA for MAP kinase activated protein kinase. |
| SEQ ID NO: 1398 | g407806 | *H.sapiens* mRNA for CB2 (peripheral) cannabinoid receptor |
| SEQ ID NO: 1399 | g414316 | *Homo sapiens* E2F-related transcription factor (DP-1) mRNA, complete |
| SEQ ID NO: 1400 | g415822 | *H.sapiens* mRNA for NOT. |
| SEQ ID NO: 1401 | g416141 | Human AH-receptor mRNA, complete cds. |
| SEQ ID NO: 1402 | g425147 | Human TGF-b superfamily receptor type I mRNA, complete cds. |

TABLE 1-continued

| SEQ ID NO: | ID | Description |
|---|---|---|
| SEQ ID NO: 1403 | g431327 | Human transcription factor mRNA, complete cds. |
| SEQ ID NO: 1404 | g433494 | H.sapiens mRNA for platelet derived growth factor alpha receptor. |
| SEQ ID NO: 1405 | g438625 | Human cytochrome P450 pseudogene mRNA. |
| SEQ ID NO: 1406 | g439225 | Human mRNA for fructose-1,6-bisphosphatase, complete cds. |
| SEQ ID NO: 1407 | g441452 | H.sapiens mRNA for nitric oxide synthase. |
| SEQ ID NO: 1408 | g453368 | Human maspin mRNA, complete cds. |
| SEQ ID NO: 1409 | g455449 | Human tyrosine kinase (MATK) mRNA, complete cds. |
| SEQ ID NO: 1410 | g456256 | Human stromelysin-3 mRNA. |
| SEQ ID NO: 1411 | g456426 | Human (clone PSK-J3) cyclin-dependent protein kinase mRNA, complete |
| SEQ ID NO: 1412 | g458543 | H.sapiens mRNA for p40phox. |
| SEQ ID NO: 1413 | g463549 | Human clone pSK1 interferon gamma receptor accessory factor-1 (AF-1) |
| SEQ ID NO: 1414 | g464186 | Human mRNA for platelet-type phosphofructokinase, complete cds. |
| SEQ ID NO: 1415 | g467511 | Human mRNA for MLL. |
| SEQ ID NO: 1416 | g469170 | Human chaperonin 10 mRNA, complete cds. |
| SEQ ID NO: 1417 | g471316 | H.sapiens mRNA for ORL1 receptor. |
| SEQ ID NO: 1418 | g472555 | Human monocyte chemoattractant protein 1 receptor (MCP-1RA) |
| SEQ ID NO: 1419 | g472557 | Human monocyte chemoattractant protein 1 receptor (MCP-1RB) |
| SEQ ID NO: 1420 | g475003 | Human mRNA for protein tyrosine phosphatase. |
| SEQ ID NO: 1421 | g482802 | Human interleukin-10 receptor mRNA, complete cds. |
| SEQ ID NO: 1422 | g483844 | Human FLT3/FLK2 ligand mRNA, complete cds. |
| SEQ ID NO: 1423 | g493244 | Human mRNA for DAD-1, complete cds. |
| SEQ ID NO: 1424 | g494988 | Human nicotinamide N-methyltransferase (NNMT) mRNA, complete cds. |
| SEQ ID NO: 1425 | g495251 | H.sapiens TIMP3 mRNA for tissue inhibitor of metalloproteinases-3. |
| SEQ ID NO: 1426 | g501030 | Human dioxin-inducible cytochrome P450 (CYP1B1) mRNA, complete cds. |
| SEQ ID NO: 1427 | g506334 | Human mRNA for BST-1, complete cds. |
| SEQ ID NO: 1428 | g508854 | Human (clone PWHTnT16) skeletal muscle Troponin T mRNA, complete cds. |
| SEQ ID NO: 1429 | g510524 | H.sapiens mRNA for keratinocyte transglutaminase. |
| SEQ ID NO: 1430 | g510900 | H.sapiens bcl-xL mRNA. |
| SEQ ID NO: 1431 | g516558 | Human cyclin-dependent kinase inhibitor p27kip1 mRNA, complete cds. |
| SEQ ID NO: 1432 | g522194 | Human cytochrome P450db1 mRNA, 3' end, clone HLD8.2. |
| SEQ ID NO: 1433 | g529642 | Human mRNA for leukotriene B4 omega-hydroxylase, complete cds. |
| SEQ ID NO: 1434 | g529723 | Human MUC18 glycoprotein mRNA, complete cds. |
| SEQ ID NO: 1435 | g535512 | Human homolog of yeast mutL (hPMS1) gene, complete cds. |
| SEQ ID NO: 1436 | g536878 | Human 37 years old male liver mRNA for fatty acids omega-hydroxylase |
| SEQ ID NO: 1437 | g536919 | Human cyclin H mRNA, complete cds. |
| SEQ ID NO: 1438 | g545022 | TIMP-1 = metalloproteinase inhibitor [human, keratoconus keratocytes, |
| SEQ ID NO: 1439 | g545708 | granulocyte colony-stimulating factor induced gene [human, CML |
| SEQ ID NO: 1440 | g545772 | surface antigen CD70 = type II transmembrane protein [human, |
| SEQ ID NO: 1441 | g557287 | Human protein tyrosine phosphatase 1E (PTP1E) mRNA, complete cds. |
| SEQ ID NO: 1442 | g558656 | Human CDK4-inhibitor (p16-INK4) mRNA, complete cds. |
| SEQ ID NO: 1443 | g559708 | Human mRNA for KIAA0075 gene, partial cds. |
| SEQ ID NO: 1444 | g559854 | Human transcription factor IL-4 Stat mRNA, complete cds. |
| SEQ ID NO: 1445 | g561629 | Human 4E-binding protein 1 mRNA, complete cds. |
| SEQ ID NO: 1446 | g561665 | Human cysteine protease CPP32 isoform alpha mRNA, complete cds. |
| SEQ ID NO: 1447 | g562752 | H.sapiens mRNA for cyclin F. |
| SEQ ID NO: 1448 | g563700 | Human keratinocyte lectin 14 (HKL-14) mRNA, complete cds. |
| SEQ ID NO: 1449 | g595923 | Human Bak mRNA, complete cds. |
| SEQ ID NO: 1450 | g598632 | (SPS2) mRNA, complete cds. |
| SEQ ID NO: 1451 | g598684 | chemokine LARC precursor, complete cds. gb100pri |
| SEQ ID NO: 1452 | g599833 | H.sapiens VE-cadherin mRNA. |
| SEQ ID NO: 1453 | g601892 | Human mRNA for Fas ligand, complete cds. |

TABLE 1-continued

| | | |
|---|---|---|
| SEQ ID NO: 1454 | g601917 | *Homo sapiens* glutathione S-transferase theta 2 (GSTT2) mRNA, complete |
| SEQ ID NO: 1455 | g602449 | Human germline oligomeric matrix protein (COMP) mRNA, complete cds. |
| SEQ ID NO: 1456 | g604478 | Human DP2 (Humdp2) mRNA, complete cds. |
| SEQ ID NO: 1457 | g609453 | Human G0S2 protein gene, complete cds. |
| SEQ ID NO: 1458 | g623236 | *H.sapiens* bcl-xS mRNA. |
| SEQ ID NO: 1459 | g632544 | Human neuronal apoptosis inhibitory protein mRNA, complete cds. |
| SEQ ID NO: 1460 | g632973 | Human cytokine receptor (EBI3) mRNA, complete cds. |
| SEQ ID NO: 1461 | g633072 | Human mRNA for protein-tyrosine phosphatase HPTPeta, complete cds. |
| SEQ ID NO: 1462 | g639715 | Human p14-CDK inhibitor mRNA, complete cds. |
| SEQ ID NO: 1463 | g641957 | Human nonmuscle myosin heavy chain-B (MYH10) mRNA, partial cds. |
| SEQ ID NO: 1464 | g665587 | Human mRNA for calmodulin, complete cds. |
| SEQ ID NO: 1465 | g673391 | *H.sapiens* BLR2 gene. |
| SEQ ID NO: 1466 | g684921 | Human neutrophil-activating ENA-78 prepeptide gene, complete cds. |
| SEQ ID NO: 1467 | g685173 | *Homo sapiens* MAP kinase kinase 3 (MKK3) mRNA, complete cds. |
| SEQ ID NO: 1468 | g703117 | *Homo sapiens* thyroid receptor interactor (TRIP9) gene, complete cds. |
| SEQ ID NO: 1469 | g736236 | *H.sapiens* mRNA for central cannabinoid receptor. |
| SEQ ID NO: 1470 | g736682 | *Homo sapiens* signal transducer and activator of transcription (STAT5) |
| SEQ ID NO: 1471 | g746414 | Human I kappa BR mRNA complete cds. |
| SEQ ID NO: 1472 | g755465 | Human transmembrane protein mRNA, complete cds. |
| SEQ ID NO: 1473 | g755652 | *Homo sapiens* protein tyrosine phosphatase delta mRNA, complete cds. |
| SEQ ID NO: 1474 | g758797 | Human Bak protein mRNA, complete cds. |
| SEQ ID NO: 1475 | g765255 | CD39 = lymphoid cell activation antigen [human, B lymphoblastoid cell |
| SEQ ID NO: 1476 | g780305 | cell receptor precursor mRNA, clone c1-6, |
| SEQ ID NO: 1477 | g780373 | complete cds. |
| SEQ ID NO: 1478 | g784993 | *H.sapiens* mRNA for EMR1 hormone receptor. |
| SEQ ID NO: 1479 | g791184 | Human Rch1 (RCH1) mRNA, complete cds. |
| SEQ ID NO: 1480 | g793842 | *H.sapiens* mRNA for ribosomal protein L29. |
| SEQ ID NO: 1481 | g804984 | *H.sapiens* BAK mRNA for BCl-2 homologue. |
| SEQ ID NO: 1482 | g806640 | *Homo sapiens* cytosolic selenium-dependent glutathione peroxidase gene, |
| SEQ ID NO: 1483 | g806765 | Human 76 kDa tyrosine phosphoprotein SLP-76 mRNA, complete cds. |
| SEQ ID NO: 1484 | g808914 | *Homo sapiens* TNF receptor-1 associated protein (TRADD) mRNA, 3' end of |
| SEQ ID NO: 1485 | g809486 | Human Fas-associating death domain-containing protein mRNA, complete |
| SEQ ID NO: 1486 | g818001 | Human transforming growth factor-beta type III receptor (TGF-beta) |
| SEQ ID NO: 1487 | g829637 | Human pre-granzyme 3 mRNA, complete cds. |
| SEQ ID NO: 1488 | g840770 | *H.sapiens* mRNA for leucocyte antigen CD97. |
| SEQ ID NO: 1489 | g860989 | *H.sapiens* mRNA for RNA polymerase II elongation factor-like protein. |
| SEQ ID NO: 1490 | g862374 | Human 180 kDa transmembrane PLA2 receptor mRNA, complete cds. |
| SEQ ID NO: 1491 | g862620 | Human lymphocyte differentiation antigen CD38 mRNA, complete cds. |
| SEQ ID NO: 1492 | g862622 | Human cell surface protein CD19 (CD19) gene, complete cds. |
| SEQ ID NO: 1493 | g881474 | Human pephBGT-1 betaine-GABA transporter mRNA, complete cds. |
| SEQ ID NO: 1494 | g882253 | Human cysteine protease Mch2 isoform alpha (Mch2) mRNA, complete cds. |
| SEQ ID NO: 1495 | g886049 | Human Ich-2 cysteine protease mRNA, complete cds. |
| SEQ ID NO: 1496 | g886257 | *Homo sapiens* CD6 ligand (ALCAM) mRNA, complete cds. |
| SEQ ID NO: 1497 | g895928 | *H.sapiens* myeloid cell nuclear differentiation antigen mRNA, complete |
| SEQ ID NO: 1498 | g897904 | Human p58 natural killer cell receptor precursor mRNA, clone c1-42, |
| SEQ ID NO: 1499 | g902001 | Human lymphotactin precursor mRNA, complete cds. |
| SEQ ID NO: 1500 | g913405 | OX40 = cell surface antigen [human, mRNA Partial, 1034 nt]. |
| SEQ ID NO: 1501 | g961439 | Human mRNA for LD78 alpha beta, partial cds. |
| SEQ ID NO: 1502 | g975297 | Human stanniocalcin precursor (STC) mRNA, complete cds. |

TABLE 1-continued

| SEQ ID NO: 1503 | g984723 | Homo sapiens cyclin-dependent kinase (CIP1/WAF1) mRNA, with a mutation |
| --- | --- | --- |
| SEQ ID NO: 1504 | g984968 | Human signaling lymphocytic activation molecule (SLAM) mRNA, complete |
| SEQ ID NO: 1505 | g995825 | Human cyclin A/CDK2-associated p45 (Skp2) mRNA, complete cds. |
| SEQ ID NO: 1506 | g995918 | Human G protein gamma-10 subunit mRNA, complete cds. |
| SEQ ID NO: 1507 | g995938 | Human 13kD differentiation-associated protein mRNA, partial cds. |
| SEQ ID NO: 1508 | g998534 | CYP2E1 = cytochrome P450A {3' region} [human, liver, mRNA Partial. |

TABLE 2

DESCRIPTION OF cDNA LIBRARIES

ADENINB01 Library was constructed using RNA isolated from the inflamed adenoid tissue of a 3-year-old child. (RNA came from Clontech.) cDNA synthesis was initiated using a combination of oligo(dT) and random priming. Double-stranded cDNA was blunted, ligated to EcoRI adaptors, digested with XhoI, size-selected, and cloned into the XhoI and EcoRI sites of the Lambda UniZAP vector.

BMARNOT02 Library was constructed using RNA isolated from the normal bone marrow of 24 male and female Caucasian donors, 16 to 70 years old.(RNA came from Clontech.) cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Iambda UniZAP vector.

BMARNOT02 Library was constructed using RNA isolated from the normal bone marrow of 24 male and female Caucasian donors, 16 to 70 years old. (RNA came from Clontech.) cDNA synthesis was initiated using a random primer. Double-stranded cDNA was blunted, ligated to EcoRI adaptors, digested with XhoI, size-selected, and cloned into the XhoI and EcoRI sites of the Lambda UniZAP vector.

BMARNOT03 Library was constructed using 1 microgram of polyA RNA isolated from the nontumorous left tibial bone marrow tissue of a 16-year-old Caucasian male during a partial left tibial ostectomy with free skin graft. Pathology indicated the distal bone marrow and soft tissue margins were negative for tumor. Pathology for the associated tumor tissue, situated within the proximal 7 cm of the left tibia, indicated metastatic alveolar rhabdomyo sarcoma. The tumor perforated the cortical bone anteriorly into the soft tissue, with extension into the articular space. The patient presented with lower leg joint pain. Patient history included an abnormality of the red blood cells. Previous surgeries included bone and bone marrow biopsy, and soft tissue excision. The patient was treated with radiation to the buttock (8 weeks total in 1994, 1995). Patient medications included Vincristine, Adriamycin, and Cytoxan. Family history included osteoarthritis in the mother and alcohol abuse in the father. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

COLNCRT01 Library was constructed using 0.99 micrograms of polyA RNA isolated from a diseased section of the ascending colon of a 40- year-old Caucasian male during a partial colectomy. Pathology indicated Crohn's disease involving the proximal colon and including the cecum. The ascending and transverse colon displayed linear ulcerations and skip lesions. There was transmural inflammation but no fistulas. The ileum was uninvolved. There was also a benign carcinoid tumor in the tip of the appendix. Patient history included anorexia nervosa, candidiasis of the mouth, Type I diabetes, diarrhea, viral meningitis, polyp of the vocal cord, and tobacco use. Previous surgeries included repair of an inguinal hernia. Patient medications included Zantac (ranitidine), Prednisone, Annusol suppositories, and insulin. Family history included hypertension in the mother. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

COLNNOT05 Library was constructed using 1.4 micrograms of polyA RNA isolated from the normal sigmoid colon tissue of a 40-year-old Caucasian male during a partial colectomy. Pathology indicated Crohn's disease involving the proximal colon and including the cecum. The ascending and transverse colon displayed linear ulcerations and skip lesions. There was transmural inflammation but no fistulas. The ileum was uninvolved. There was also a benign carcinoid tumor in the tip of the appendix. Patient history included anorexia nervosa, candidiasis of the mouth, Type I diabetes, diarrhea, viral meningitis, polyp of the vocal cord, and tobacco use. Previous surgeries included repair of an inguinal hernia. Patient medications included Zantac (ranitidine), Prednisone, Annusol suppositories, and insulin. Family history included hypertension in the mother. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector. COLNCRT01 is a diseased ascending colon library from the same donor.

COLNNOT23 Library was constructed using 1 microgram of polyA RNA isolated from diseased colon tissue removed from a 16-year-old Caucasian male during a total colectomy with abdominal/perineal resection. Pathology indicated gastritis and pancolonitis consistent with the acute phase of ulcerative colitis. (The process is characterized by acute colitis with crypt abscess formation.) Inflammation was more severe in the transverse colon, with inflammation confined to the mucosa. There was only mild involvement of the ascending and sigmoid colon, and no significant involvement of the cecum, rectum, or terminal ileum. The patient presented with blood in the stool, anemia, abdominal pain, nausea, and vomiting. Patient medications included Minocin, Cephaxelin, Prednisone, Flagyl, Zantac (ranitidine), cortisone enemas, omrprazole, iron, dextran, and cyclosporin. Family history included irritable bowel syndrome, hypertension, and atherosclerotic coronary artery disease in a grandparent. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

COLNNOT27 Library was constructed using 1 microgram of polyA RNA isolated from diseased cecal tissue removed from 31-year-old Caucasian male during a total intra-abdominal colectomy, appendectomy, and permanent ileostomy. Pathology indicated severe active Crohn's disease involving the colon from the cecum to the rectum. There were deep rake-like ulcerations which spared the intervening mucosa. The ulcers extended into the muscularis, and there was transmural inflammation. The ileum and appendix were uninvolved. The patient presented with enteritis and diarrhea. Patient history included an irritable colon. Previous surgeries included a colonscopy. Patient medications included Asacol (mesalamine), Flagyl (metronidazole), Azulfidine (sulfasalazine), and Prednisone (glucocorticoid). cDNA synthesis was initiated using a NotI-oligo(dT) primer. Double-stranded cDNA was blunted, ligated to Acari adaptors, digested with Not, size-selected, and cloned into the Not and Acari sites of the pINCY vector (Incyte).

COLSUCT01 Library was constructed using 1 microgram of polyA RNA isolated from diseased sigmoid colon tissue removed from a 70-year-old Caucasian male during colectomy with permanent ileostomy. Pathology indicated chronic ulcerative colitis in the distal 25 cm of the colon with acute and chronic inflammation and architectural distortion in the area. Chronic ulcerative colitis was identified in the rectum and sigmoid colon. There was hyperplastic polyp in the ascending colon. The remaining colon, terminal ileum, appendix, and anus showed no diagnostic abnormality. The patient presented with functional diarrhea and blood in the stool. Patient history included benign neoplasm of the colon, hyperlipidemia, benign hypertension, atrial fibrillation, and tobacco use. Patient medications included Asacol (mesalamine) for colitis, Prednisone (glucocorticoid), Coumadine, Lanoxin, Hygroton, Zestril, and Rowasa. Family history included atherosclerotic coronary artery disease and a myocardial infarction in the father, atherosclerotic coronary artery disease and a myocardial infarction in the mother, atherosclerotic coronary artery disease and a myocardial infarction in the sibling(s), and atherosclerotic coronary artery disease in the grandparent(s). cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

ENDCNOT01 Library was constructed using 1 microgram of polyA RNA isolated from endothelial cells removed from the coronary artery of a 58-year-old Hispanic male. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

ENDCNOT02 Library was constructed using 1 microgram of polyA RNA isolated from dermal microvascular endothelial cells removed from a 30-year-old Caucasian female. cDNA synthesis was initiated using a NotI-oligo (dT) primer. Double-stranded cDNA was blunted, ligated to EcoRI adaptors, digested with NotI, size-selected, and cloned into the NotI and EcoRI sites of the pINCY vector (Incyte).

ENDCNOT03 Library was constructed using 1 microgram of polyA RNA isolated from dermal microvascular endothelial cells removed from a neonatal Caucasian male. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

EOSIHET02 Library was constructed using RNA isolated from peripheral blood cells apheresed from a 48-year-old Caucasian male. Patient history included hypereosinophilia. Patient medications included hydroxyurea, allopruinol, warfarin, prednisone, and interferon alpha, ascorbic acid, and aspirin. The cell population was determined to be greater than 77% eosinophils by Wright's staining. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector.

HMC1NOT01 Library was constructed using RNA isolated from the HMC-1 human mast cell line derived from a 52-year-old female. Patient history included mast cell leukemia. Family history included atherosclerotic coronary artery disease and a joint disorder involving multiple joints in the mother; and cerebrovascular disease, diabetes insipidus, and tobacco abuse in the father. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector.

HUVENOB01 Library was constructed using RNA isolated from unstimulated HUV-EC-C (ATCC CRL 1730) cells. HUV-EC-C is an endothelial cell line derived from the vein of a normal human umbilical cord (ref: PNAS 81:6413). RNA was made by lysing $2 \times 10e 8$ cells in GuSCN, followed by DNAse treatment. cDNA synthesis was initiated using a combination of oligo(dT) and random priming. Double-stranded cDNA was blunted, ligated to EcoRI adaptors, digested with XhoI, size-selected, and cloned into the XhoI and EcoRI sites of the Lambda UniZAP vector.

HUVELPB01 Library was constructed using RNA isolated from HUV-EC-C (ATCC CRL 1730) cells that were stimulated with cytokine/LPS. HUV-EC-C is an endothelial cell line derived from the vein of a normal human umbilical cord (ref: PNAS 81:6413). RNA was isolated from two pools of HUV-EC-C cells that had been treated with either gamma IFN and TNF-alpha or IL-1 beta and LPS. In the first instance, HUV-EC-C cells were treated with 4 units/ml TNF and 2 units/ml IFNg for 96 hours at a density of $4.9 \times 10e8$ cells/ml. The yield was 1296 micrograms of total RNA, from which 11 microgrammes of polyA was obtained (0.8% recovery). In the second instance, cells were treated with 1 units/ml IL-1 and 100 ng/ml LPS for 5 hours. Density was $1 \times 108$ cells/ml. The yield was 1000 micrograms of RNA, from which 5.3 micrograms of polyA was isolated (0.5% recovery). cDNA synthesis was initiated using a combination of oligo(dT) and random priming. Double-stranded cDNA was blunted, ligated to EcoRI adaptors, digested with XhoI, size-selected, and cloned into the XhoI and EcoRI sites of the Lambda UniZAP vector.

HUVELPB01 Library was constructed using RNA isolated from HUV-EC-C (ATCC CRL 1730) cells that were stimulated with cytokine/LPS. HUV-EC-C is an endothelial cell line derived from the vein of a normal human umbilical cord (ref: PNAS 81:6413). RNA was isolated from two pools of HUV-EC-C cells that had been treated with either gamma IFN and TNF-alpha or IL-1 beta and LPS. In the first instance, HUV-EC-C cells were treated with 4 units/ml TNF and 2 units/ml IFNg for 96 hours at a density of $4.9 \times 10e8$ cells/ml. The yield was 1296 micrograms of total RNA, from which 11 micrograms of polyA was obtained (0.8% recovery). In the second instance, cells were treated with 1 units/ml IL-1 and 100 ng/ml LPS for 5 hours. Density was $1 \times 108$ cells/ml. The yield was 1000 micrograms of RNA, from which 5.3 micrograms of polyA was isolated (0.5% recovery). cDNA synthesis was initiated using a combination of oligo(dT) and random priming. Double-stranded cDNA was blunted, ligated to EcoRI adaptors, digested with XhoI, size-selected, and cloned into the XhoI and EcoRI sites of the Lambda UniZAP vector.

HUVENOB01 Library was constructed using RNA isolated from unstimulated HUV-EC-C (ATCC CRL 1730) cells. HUV-EC-C is an endothelial cell line derived from the vein of a normal human umbilical cord (ref: *PNAS* 81:6413). RNA was made by lysing $2 \times 10e8$ cells in GuSCN, followed by DNAse treatment. cDNA synthesis was initiated using a combination of oligo(dT) and random priming. Double-stranded cDNA was blunted, ligated to EcoRI adaptors, digested with XhoI, size-selected, and cloned into the XhoI and EcoRI sites of the Lambda UniZAP vector.

HUVESTB01 Library was constructed using RNA isolated from shear-stressed HUV-EC-C (ATCC CRL 1730) cells. HUV-EC-C is an endothelial cell line derived from the vein of a normal human umbilical cord (ref: *PNAS* 81:6413). Before RNA isolation, the cells were subjected to a shear stress of 10 dynes/cm. cDNA synthesis was initiated using a combination of oligo(dT) and random priming. Double-stranded cDNA was blunted, ligated to EcoRI adaptors, digested with XhoI, size-selected, and cloned into the XhoI and EcoRI sites of the Lambda UniZAP vector.

LEUKNOT02 Library was constructed using 1 microgram of polyA RNA isolated from white blood cells of a 45-year-old female with blood type O+. The donor tested positive for cytomegalovirus (CMV). cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

LEUKNOT03 Library was constructed using 1 microgram of polyA RNA isolated from white blood cells of a 27-year-old female with blood type A+. The donor tested negative for cytomegalovirus (CMV). cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

LNODNOT02 Library was constructed using 1 microgram of polyA RNA isolated from the lymph node tissue of a 42-year-old Caucasian female, who died of cardiac arrest. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

LNODNOT03 Library was constructed using 1 microgram of polyA RNA isolated from lymph node tissue removed from a 67-year-old Caucasian male during a segmental lung resection and bronchoscopy. On microscopic exam, this tissue was found to be extensively necrotic with 10% viable tumor. Pathology for the associated tumor tissue indicated invasive grade 3–4 squamous cell carcinoma, forming a mass in the right lower lobe, which grossly puckers the pleura. Microscopically, tumor invaded into but not through the visceral pleura. Focally, tumor was seen obliterating the bronchial lumen. The bronchial margin was negative for dysplasia/neoplasm. One of two intrapulmonary lymph nodes was metastatically involved. One of four inferior mediastinal(subcarinal) and two of eight superior mediastinal (right lower paratracheal) lymph nodes were metastatically involved. Multiple lymph nodes were negative for tumor. A small component of grade 3 adenocarcinoma was present in the tumor, which manifested itself most prominently in some of the metastases in the regional lymph nodes. The patient presented with a cough. Patient history included hemangioma and tobacco abuse. Previous surgeries included appendectomy. Patient medications included doxycycline. Family history included atherosclerotic coronary artery disease, benign hypertension, and congestive heart failure in the mother; atherosclerotic coronary artery disease and congestive heart failure in the father; and atherosclerotic coronary artery disease in the grandparent(s). cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

LUNGAST01 Library was constructed using 2 micrograms of polyA RNA isolated from the lung tissue of a 17-year-old Caucasian male, who died from head trauma. The patient had a history of asthma. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

LUNGFET03 Library was constructed using 1 microgram of polyA RNA isolated from lung tissue removed from a Caucasian female fetus, who died at 20 weeks of gestation from fetal demise. Serology was negative. Family history included seven days of erythromycin treatment for bronchitis in the mother during the first trimester. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte). COLNFET02 (colon), LIVRFET02 (liver), and LUNGFET05 (lung) are other libraries from the same donor.

LUNGNOT01 Library was constructed at Stratagene, using RNA isolated from the lung tissue of a 72-year-old male. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector. Following Lambda UniZAP packaging, $2 \times 10e6$ primary clones were then amplified to stabilize the library for long-term storage. Amplification may significantly skew sequence abundances. The same Stratagene library (STR937210) was used for LUNGNOM01, obtained from the WashU-Merck EST Project.

LUNGNOT02 Library was constructed using RNA isolated from the lung tissue of a 47-year-old Caucasian male, who died of a subarachnoid hemorrhage. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector.

LUNGNOT04 Library was constructed using 1.6 micrograms of polyA RNA isolated from the lung tissue of a 2-year-old Hispanic male, who died from cerebral anoxia. Past medical history and serologies were negative. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

LUNGNOT09 Library was constructed using 1 microgram of polyA RNA isolated from the lung tissue of a 23-week-old Caucasian male fetus. The pregnancy was terminated following a diagnosis by ultrasound of infantile polycystic kidney disease. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

LUNGNOT10 Library was constructed using 1 microgram of polyA RNA isolated from the lung tissue of a Caucasian male fetus, who died at 23 weeks of gestation from premature birth. Serology was negative. Family history included diabetes in the mother. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

LUNGNOT12 Library was constructed using 0.464 micrograms of polyA RNA isolated from nontumorous lung tissue removed from a 78-year-old Caucasian male during a segmental lung resection and regional lymph node resection. Surgery followed a diagnosis of a malignant neoplasm of the right upper lobe. Pathology indicated fibrosis pleura was puckered, but not invaded. Pathology for the associated tumor tissue indicated an invasive pulmonarygrade 3 adenocarcinoma, forming a peripheral mass with associated fibrosis. The patient presented with premature ventricular beats. Patient history included cerebrovascular disease, arteriosclerotic coronary artery disease, thrombophlebitis, chronic obstructive pulmonary disease, asthma, and tobacco use. Previous surgeries included a cholecystectomy, radical prostatectomy, and regional lymph node excision for malignant prostate neoplasm. Patient medications included Cipro I.V. (ciprofloxacin) for a systemic infection; Atenolol (tenormin) for arrhythmia; Darvocet-N (propoxyphene napsylate) for pain; Naprosyn (naproxen), an anti-inflammatory and analgesic; and multivitamins. Family history included intracranial hematoma with deep coma following injury in the mother, and cerebrovascular disease, arteriosclerotic coronary artery disease, and Type I diabetes in a sibling. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

LUNGNOT15 Library was constructed using 1 microgram of polyA RNA isolated from nontumorous lung tissue removed from the left lower lobe of a 69-year-old Caucasian male during a segmental lung resection. Pathology for the associated tumor tissue indicated residual grade 3 invasive squamous cell carcinoma. The upper lobe also contained residual grade 3 invasive squamous cell carcinoma. Surgical margins and lymph nodes were negative for tumor. Patient history included acute myocardial infarction, prostatic hyperplasia, benign hypertension, malignant skin neoplasm, and tobacco use. Previous surgeries included a multivessel coronary artery bypass. Patient medications included Hytrin (terazosin) for benign prostate hyperplasia; Norvasc (amiodipine besylate) for angina; Atenolol (tenormin) for arrhythmia; KCL (potassium chloride); Lasix (furosemide), a diuretic; and blood-pressure medicine. Family history included cerebrovascular disease and Type I diabetes in the mother, and acute myocardial infarction and arteriosclerotic coronary disease in the father. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

SINTBST01 Library was constructed using 1 microgram of polyA RNA isolated from the ileum tissue of an 18-year-old Caucasian female with irritable bowel syndrome (IBS). The ileum tissue, along with the cecum and appendix, were removed during bowel anastomosis. Pathology indicated Crohn's disease of t he ileum, involving 15 cm of the small bowel. The cecum and appendix were unremarkable, and the margins were uninvolved. The patient presented with abdominal pain and regional enteritis. Patient history included osteoporosis of the vertebra and abnormal blood chemistry. Patient medications included Prilosec (omeprazole), Pentasa (mesalamine), amoxicillin, and multivitamins. Family history included cerebrovascular disease in the mother and a grandparent, and atherosclerotic coronary artery disease in a grandparent. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

LUNGNOT18 Library was constructed using 1 microgram of polyA RNA isolated from nontumorous lung tissue removed from the left upper lobe of a 66-year-old Caucasian female during a segmental lung resection and regional lymph node biopsy. Pathology for the associated tumor tissue indicated a grade 2 adenocarcinoma with bronchoalveolar features and prominent inflammation, forming a well-circumscribed nodular mass. The tumor did not involve the pleura. Surgical margins and lymph nodes were negative for tumor. Patient history included cerebrovascular disease, atherosclerotic coronary artery disease, pulmonary insufficiency, and a normal delivery. Previous surgeries included an endarterectomy. Patient medications included Trental, Zocor, and aspirin. Family history included a myocardial infarction in the mother and father, and atherosclerotic coronary artery disease in a sibling. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

LUNGNOT20 Library was constructed using 1 microgram of polyA RNA isolated from lung tissue removed from the right upper lobe a 61-year-old Caucasian male during a segmental lung resection. Pathology indicated panacinal emphysema with blebs in the right anterior upper lobe and apex, as well as emphysema in the right posterior upper lobe. Panacinal emphysema was also identified in the left upper lobe lingula with one 3 mm calcified granuloma. Patient history included benign hypertension, angina pectoris, gastric ulcer, and tobacco and alcohol use. Patient medications included Azmacort, Atrovent, Ventolin, nitroglycerine, and tetracycline HCl. Family history included a subdural hemorrhage in the father; cancer of an unidentified site in the mother; benign hypertension, atherosclerotic coronary artery disease, pneumonia, and an unspecified muscle disorder in a sibling; and benign hypertension, atherosclerotic coronary artery disease, and cancer of an unidentified site in a grandparent. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

MMLR1DT01 Library was constructed using 2 micrograms of polyA RNA isolated from adherent mononuclear cells, which came from a pool of male and female donors. The cells were cultured for 24 hours following Ficoll Hypaque centrifugation. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

MMLR3DT01 Library was constructed using 2 micrograms of polyA RNA isolated from adherent mononuclear cells, which came from a pool of male and female donors. The cells were cultured for 72 hours following Ficoll Hypaque centrifugation. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

MPHGLPT02 Library was constructed using 1 microgram of polyA RNA isolated from adherent mononuclear cells, which came from a pool of male and female donors. The cells were isolated using Ficoll Hypaque centrifugation, and the predominantly macrophage-containing population was stimulated with LPS at 1 μg/ml for 2 hours before isolation of total RNA and polyA selection. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

MPHGNOT02 Library was constructed using total RNA isolated from plastic adherent mononuclear cells obtained from the peripheral blood of a healthy 24-year-old Caucasian male. After a 2-hour culture in medium containing normal human serum, the cells were harvested and lysed in a buffer containing GuSCN, then spun through CsCl to obtain RNA for library construction. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector. Because this library was made from total RNA, it has an unusually high proportion of unique singleton sequences, which may not all come from polyA RNA species.

MPHGNOT03 Library was constructed using 4 micrograms of polyA RNA isolated from plastic adherent (2 hour culture) mononuclear cells isolated from buffy coat units obtained from unrelated male and female donors. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector.

NEUTFMT01 Library was constructed using total RNA isolated from peripheral blood granulocytes collected by density gradient centrifugation through Ficoll-Hypaque. The cells were isolated from buffy coat units obtained from unrelated male and female donors. Cells were cultured in 10 nM fMLP for 30 minutes, lysed in GuSCN, and spun through CsCl to obtain RNA for library construction. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector. Because this library was made from total RNA, it has an unusually high proportion of unique singleton sequences, which may not all come from polyA RNA species.

NEUTGMT01 Library was constructed using 1 microgram of polyA RNA isolated from peripheral blood granulocytes collected by density gradient centrifugation through Ficoll-Hypaque. The cells were isolated from buffy coat units obtained from 20 unrelated male and female donors. Cells were cultured in 10 nM GM-CSF for 1 hour before washing and harvesting for total RNA preparation. cDNA synthesis was initiated using a NotI-oligo(dT)primer. Double-stranded cDNA was blunted, ligated to SalI adaptors, digested with NotI, size-selected, and cloned into the NotI and SalI sites of the pSPORT1 vector.

NEUTGMT01 Library was constructed using 1 microgram of polyA RNA isolated from peripheral blood granulocytes collected by density gradient centrifugation through Ficoll-Hypaque. The cells were isolated from buffy coat units obtained from 20 unrelated male and female donors. Cells were cultured in 10 nM GM-CSF for 1 hour before washing and harvesting for total RNA preparation. cDNA synthesis was initiated using a NotI-oligo(dT)primer. Double-stranded cDNA was blunted, ligated to SalI adaptors, digested with NotI, size-selected, and cloned into the NotI and SalI sites of the pSPORT1 vector.

NEUTLPT01 Library was constructed using 64 micrograms of total RNA isolated from peripheral blood granulocytes collected by density gradient centrifugation through Ficoll-Hypaque. The cells were isolated from buffy coat units obtained from unrelated male and female donors. Cells were cultured in 100 ng/ml *E. coli* LPS for 30 minutes, lysed in GuSCN, and spun through CsCl to obtain RNA for library construction. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector. Because this library was made from total RNA, it has an unusually high proportion of unique singleton sequences, which may not all come from polyA RNA species.

PANCDIT01 Library was constructed using polyA RNA isolated from pancreas tissue removed from a 15-year-old Caucasian male, who died from a self-inflicted gunshot wound. Patient history included Type I diabetes. Previous surgeries included an appendectomy. Patient medications included insulin. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector.

PANCNOT01 Library was constructed using RNA isolated from the pancreatic tissue of a 29-year-old Caucasian male, who died from head trauma. Serologies were positive for cytomegalovirus (CMV) but otherwise negative. Patient history included alcohol, marijuana, and tobacco use. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector.

PANCNOT04 Library was constructed using 2.5 micrograms of polyA RNA isolated from the pancreatic tissue of a 5-year-old Caucasian male, who died in a motor vehicle accident. Serology was positive for cytomegalovirus (CMV), but otherwise serologies and medical history were negative. Patient medications included Dopamine, Dobutamine, Ancef (cefazolin), DDAVP, Mannitol, and Pepcid (famotidine). cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

PANCNOT04 Library was constructed using 2.5 micrograms of polyA RNA isolated from the pancreatic tissue of a 5-year-old Caucasian male, who died in a motor vehicle accident. Serology was positive for cytomegalovirus (CMV), but otherwise serologies and medical history were negative. Patient medications included Dopamine, Dobutamine, Ancef (cefazolin), DDAVP, Mannitol, and Pepcid (famotidine). cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

PANCNOT05 Library was constructed using 1.6 micrograms of polyA RNA isolated from the pancreatic tissue of a 2-year-old Hispanic male, who died from cerebral anoxia. Past medical history and serologies were negative. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

SINTNOT13 Library was constructed using 1 microgram of polyA RNA isolated from ileum tissue removed from a 25-year-old Asian female during a partial colectomy and temporary ileostomy. Pathology indicated moderately active chronic ulcerative colitis, involving colonic mucosa from the distal margin to the ascending colon. The cecum, appendix, and attached ileal segment were uninvolved. Rectal mucosa also showed moderately active chronic ulcerative colitis. The patient presented with diarrhea, blood in the stool, and abdominal pain. Patient history included papilloma virus, deficiency anemia, migraines, backache, depressive disorder, and tobacco use. Patient medications included Rowasa (mesalamine rectal suppositories) for colitis, Nordette(levonorgestrel and ethinyl estradiol), Asacol (mesalamine), and digestive herbs. Family history included hyperlipidemia and depressive disorder in the mother; and a malignant cervical neoplasm, viral hepatitis A, depressive disorder, and alcohol and drug use in the sibling (s). cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

SPLNFET01 Library was constructed at Stratagene, using RNA isolated from a pool of fetal spleen tissue. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector. Following Lambda UniZAP packaging, 2×10e6 primary clones were then amplified to stabilize the library for long-term storage. Amplification may significantly skew sequence abundances. The same Stratagene library (STR937205) was used for SPLNFEM01, obtained from the WashU-Merck EST Project.

SPLNFET02 Library was constructed using 1 microgram of polyA RNA isolated from spleen tissue removed from a Caucasian male fetus, who died at 23 weeks of gestation from premature birth. Serology was negative. Family history included diabetes in the mother. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

SPLNNOT02 Library was constructed using RNA isolated from the spleen tissue of a 29-year-old Caucasian male, who died from head trauma. Serologies were positive for cytomegalovirus (CMV) but otherwise negative. Patient history included alcohol, marijuana, and tobacco use. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector.

SPLNNOT04 Library was constructed using 1 microgram of polyA RNA isolated from the spleen tissue of a 2-year-old Hispanic male, who died from cerebral anoxia. Past medical history and serologies were negative. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

SYNOOAT01 Library was constructed using 1 microgram of polyA RNA isolated from the knee synovial membrane tissue of an 82-year-old female with osteoarthritis. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

SYNORAB01 Library was constructed using RNA isolated from the synovial membrane tissue of a 68-year-old Caucasian female with rheumatoid arthritis. Patient medications included enteric coated ASA, fluoride 20, fiorinal, iron gluconate, Gold 1 tab, and multivitamins. cDNA synthesis was initiated using a combination of oligo(dT) and random priming. Double-stranded cDNA was blunted, ligated to EcoRI adaptors, digested with XhoI, size-selected, and cloned into the XhoI and EcoRI sites of the Lambda UniZAP vector.

SYNORAT01 Library was constructed using RNA isolated from synovial membrane tissue removed from the elbow of a 51-year-old Asian female with rheumatoid arthritis. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

SYNORAT03 Library was constructed using 1 microgram of polyA RNA isolated from the wrist synovial membrane tissue of a 56-year-old female with rheumatoid arthritis. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

SYNORAT04 Library was constructed using 1 microgram of polyA RNA isolated from the wrist synovial membrane tissue of a 62-year-old female with rheumatoid arthritis. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

SYNORAT05 Library was constructed using 1 microgram of polyA RNA isolated from the knee synovial tissue of a 62-year-old female with rheumatoid arthritis. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

TBLYNOT01 Library was constructed at Stratagene (STR937214), using RNA isolated from a hybrid of T-B lymphoblasts from a leukemic cell line. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector. Following Lambda UniZAP packaging, 2×10e6 primary clones were then amplified to stabilize the library for long-term storage. Amplification may significantly skew sequence abundances.

THP1AZT01 Library was constructed using 1 microgram of polyA RNA isolated from THP-1 promonocyte cells treated for three days with 0.8 micromolar 5-aza-2'-deoxycytidine. THP-1 (ATCC TIB 202) is a human promonocyte line derived from peripheral blood of a 1-year-old Caucasian male with acute monocytic leukemia (ref: *Int. J. Cancer* (1980) 26:171). cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

THP1AZT01 Library was constructed using 1 microgram of polyA RNA isolated from THP-1 promonocyte cells treated for three days with 0.8 micromolar 5-aza-2'-deoxycytidine. THP-1 (ATCC TIB 202) is a human promonocyte line derived from peripheral blood of a 1-year-old Caucasian male with acute monocytic leukemia (ref: *Int. J. Cancer* (1980) 26:171). cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

THP1NOB01 Library was constructed using RNA isolated from cultured, unstimulated THP-1 cells. THP-1 (ATCC TIB 202) is a human promonocyte line derived from the peripheral blood of a 1-year-old Caucasian male with acute monocytic leukemia (ref: *Int. J. Cancer* (1980) 26:171). RNA was isolated from 2×108 cells using GuSCN lysis, followed by DNAse treatment. cDNA synthesis was initiated using a combination of oligo(dT) and random priming. Double-stranded cDNA was blunted, ligated to EcoRI adaptors, digested with XhoI, size-selected, and cloned into the XhoI and EcoRI sites of the Lambda UniZAP vector.

THP1PLB01 Library was constructed using RNA isolated from THP-1 cells cultured for 48 hours with 100 ng/ml phorbol ester (PMA), followed by a 4-hour culture in media containing 1 ug/ml LPS. THP-1 (ATCC TIB 202) is a human promonocyte line derived from the peripheral blood of a 1-year-old male with acute monocytic leukemia (ref: *Int. J. Cancer* (1980) 26:171). cDNA synthesis was initiated using a combination of oligo(dT) and random priming. Double-stranded cDNA was blunted, ligated to EcoRI adaptors, digested with XhoI, size-selected, and cloned into the XhoI and EcoRI sites of the Lambda UniZAP vector.

THP1PLB02 Library was constructed by reamplification of THP1PLB01, which was made using RNA isolated from THP-1 cells cultured for 48 hours with 100 ng/ml phorbol ester (PMA), followed by a 4-hour culture in media containing 1 ug/ml LPS. THP-1 (ATCC TIB 202) is a human promonocyte line derived from the peripheral blood of a 1-year-old male with acute monocytic leukemia (ref: *Int. J. Cancer* (1980) 26:171). cDNA synthesis was initiated using a combination of oligo(dT) and random priming. Double-stranded cDNA was blunted, ligated to EcoRI adaptors, digested with XhoI, size-selected, and cloned into the-XhoI and EcoRI sites of the Lambda UniZAP vector. Following Lambda UniZAP packaging, 1×10e6 primary clones were then amplified to stabilize the library for long-term storage. Amplification may significantly skew sequence abundances.

THP1NOT01 Library was constructed using 1 microgram of polyA RNA isolated from untreated THP-1 cells. THP-1 (ATCC TIB 202) is a human promonocyte line derived from the peripheral blood of a 1-year-old Caucasian male with acute monocytic leukemia (ref: *Int. J. Cancer* (1980) 26:171).cDNA synthesis was initiated using a NotI-oligo (dT) primer. Double-stranded cDNA was blunted, ligated to EcoRI adaptors, digested with NotI, size-selected, and cloned into the NotI and EcoRI sites of the pINCY vector (Incyte).

THP1NOT03 Library was constructed using 1 microgram of polyA RNA isolated from untreated THP-1 cells. THP-1 (ATCC TIB 202) is a human promonocyte line derived from the peripheral blood of a 1-year-old Caucasian male with acute monocytic leukemia (ref: *Int. J. Cancer* (1980) 26:171). cDNA synthesis was initiated using a NotI-oligo (dT) primer. Double-stranded cDNA was blunted, ligated to EcoRI adaptors, digested with NotI, size-selected, and cloned into the NotI and EcoRI sites of the pINCY vector (Incyte).

THP1PEB01 Library was constructed using RNA isolated from THP-1 cells cultured for 48 hours with 100 ng/ml phorbol ester (PMA). Following culture in PMA, cells were lysed in GuSCN. THP-1 (ATCC TIB 202) is a human promonocyte line derived from the peripheral blood of a 1-year-old Caucasian male with acute monocytic leukemia (ref: *Int. J. Cancer* (1980) 26:171). cDNA synthesis was initiated using a combination of oligo(dT) and random priming. Double-stranded cDNA was blunted, ligated to EcoRI adaptors, digested with XhoI, size-selected, and cloned into the XhoI and EcoRI sites of the Lambda UniZAP vector.

THYMNOT02 Library was constructed using polyA RNA isolated from thymus tissue removed from a 3-year-old Caucasian male, who died from drowning. Serologies were negative. cDNA synthesis was initiated using an XhoI-oligo (dT) primer. Double-stranded cDNA was blunted, ligated to EcoRI adaptors, digested with XhoI, size-selected, and cloned into the XhoI and EcoRI sites of the Lambda UniZAP vector.

TLYMNOR01 Library was constructed using RNA isolated from non-adherent peripheral blood mononuclear cells obtained from a 24-year-old Caucasian male. (This is the same RNA source used for TLYMNOT01.) The cells were purified on Ficoll Hypaque, then harvested, lysed in GuSCN, and spun through CsCl to obtain RNA for library construction. cDNA synthesis was initiated using a random primer. Double-stranded cDNA was blunted, ligated to EcoRI adaptors, digested with XhoI, size-selected, and cloned into the XhoI and EcoRI sites of the Lambda UniZAP vector.

TLYMNOT01 Library was constructed using RNA isolated from non-adherent peripheral blood mononuclear cells obtained from a 24-year-old Caucasian male. The cells were purified on Ficoll Hypaque, then harvested, lysed in GuSCN, and spun through CsCl to obtain RNA for library construction. PolyA RNA was isolated using oligo(dT) cellulose. cDNA synthesis was initiated using an XhoI-oligo (dT) primer. Double-stranded cDNA was blunted, ligated to EcoRI adaptors, digested with XhoI, size-selected, and cloned into the XhoI and EcoRI sites of the Lambda UniZAP vector. TLYMNOR01 is a random-primed library from the same RNA source.

TMLR2DT01 Library was constructed using RNA isolated from non-adherent peripheral blood mononuclear cells. The blood was obtained from unrelated male and female donors. Cells from each donor were purified on Ficoll Hypaque, then co-cultured for 24 hours in medium containing normal human serum at a cell density of 2×106 cells/ml. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector.

TMLR3DT01 Library was constructed using RNA isolated from non-adherent and adherent peripheral blood mononuclear cells collected from two unrelated Caucasian male donors (25 and 29 years old). Cells from each donor were purified on Ficoll Hypaque, then co-cultured for 96 hours in medium containing normal human serum at a cell density of 2×106 cells/ml. The non-adherent cells were collected, then the adherent cells were collected by scraping with a rubber policeman, and the populations were pooled. The pooled cells were washed once in PBS, lysed in a buffer containing GuSCN, and spun through CsCl to obtain RNA for library construction. PolyA RNA was isolated using a Qiagen Oligotex kit. cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector.

TONSNOT01 Library was constructed using 1.2 micrograms of polyA RNA isolated from the tonsil tissue of a 6-year-old Caucasian male with lymphoid hyperplasia of the tonsils. cDNA synthesis was initiated using a NotI-oligo(dT) primer. Double-stranded cDNA was blunted, ligated to SalI adaptors, digested with NotI, size-selected, and cloned into the NotI and SalI sites of the pSPORT1 vector.

U937NOT01 Library was constructed at Stratagene (STR937207), using RNA isolated from the U937 monocyte-like cell line. This line (ATCCCRL1593) was established by C. Sundstrom and K. Nilsson in 1974 from malignant cells obtained from the pleural effusion of a 37-year-old Caucasian male with diffuse histiocytic lymphoma (ref: Int. J. Cancer (1976) 17: 565–577). cDNA synthesis was initiated using an XhoI-oligo(dT) primer. Double-stranded cDNA was blunted, ligated to EcoRI adaptors, digested with XhoI, size-selected, and cloned into the XhoI and EcoRI sites of the Lambda UniZAP vector. Following Lambda UniZAP packaging, 2×10e6 primary clones were then amplified to stabilize the library for long-term storage. Amplification may significantly skew sequence abundances.

UCMCL5T01 Library was constructed using 1 microgram of polyA RNA isolated from mononuclear cells obtained from the umbilical cord blood of 12 individuals. The cells were cultured for 12 days with IL-5 before RNA was obtained from the pooled lysates. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pBluescript vector.

UCMCNOT02 Library was constructed using 1 microgram of polyA RNA isolated from mononuclear cells obtained from the umbilical cord blood of nine individuals. cDNA synthesis was initiated using a NotI-oligo(dT) primer. Double-stranded cDNA was blunted, ligated to EcoRI adaptors, digested with NotI, size-selected, and cloned into the NotI and EcoRI sites of the pINCY vector (Incyte).

SEQUENCE LISTING

The patent contains a lengthy "Sequence Listing" section. A copy of the "Sequence Listing" is available in electronic form from the USPTO web site (http://seqdata.uspto.gov/sequence.html?DocID=6607879B1). An electronic copy of the "Sequence Listing" will also be available from the USPTO upon request and payment of the fee set forth in 37 CFR 1.19(b)(3).

What is claimed is:

1. A composition comprising a plurality of cDNAs for use in detecting the altered expression of genes in an immunological response, wherein said plurality of cDNAs comprises SEQ ID NOs:1–1508 or the complete complements thereof.

2. The composition of claim 1, wherein said cDNAs are immobilized on a substrate.

3. The composition of claim 1, wherein said cDNAs are hybridizable elements on a microarray.

4. A method for diagnosing or monitoring the treatment of an immunopathological condition in a sample, said method comprising:
   a) obtaining nucleic acids from a sample;
   b) contacting the nucleic acids of the sample with an array comprising the plurality of cDNAs of claim 1 under conditions to form one or more hybridization complexes;
   c) detecting said hybridization complexes; and
   d) comparing the levels of the hybridization complexes detected in step (c) with the level of hybridization complexes detected in a non-diseased sample, wherein the altered level of hybridization complexes detected in step (c) compared with the level of hybridization complexes of a non-diseased sample correlates with the presence of an immunopathological condition.

5. The method of claim 4, wherein the immunopathological condition is selected from Crohn's disease, asthma, ulcerative colitis, hypereosinophlia, irritable bowel syndrome, osteoarthritis, rheumatoid arthritis, and acute monocytic leukemia.

6. The method of claim 4, wherein said cDNAs are immobilized on a substrate.

7. The method of claim 4, wherein said cDNAs are hybridizable elements in a microarray.

* * * * *